(12) United States Patent
Yoneda et al.

(10) Patent No.: US 8,921,584 B2
(45) Date of Patent: Dec. 30, 2014

(54) COMPOSITION CONTAINING INTERMEDIATE FOR WATER-SOLUBLE MONOMER AND PROCESS FOR PRODUCTION THEREOF, COMPOSITION CONTAINING WATER-SOLUBLE MONOMER, INTERMEDIATE FOR WATER-SOLUBLE MONOMER, AND WATER-SOLUBLE MONOMER AND PROCESS FOR PRODUCTION THEREOF

(75) Inventors: Atsuro Yoneda, Suita (JP); Makoto Saito, Suita (JP); Aki Tsukajima, Suita (JP); Daisuke Michitaka, Suita (JP); Mitsuaki Makino, Suita (JP)

(73) Assignee: Nippon Shokubai Co, Ltd, Osaka (JP)

( * ) Notice: Subject to any disclaimer, the term of this patent is extended or adjusted under 35 U.S.C. 154(b) by 19 days.

(21) Appl. No.: 13/512,845

(22) PCT Filed: Dec. 3, 2010

(86) PCT No.: PCT/JP2010/071703
§ 371 (c)(1),
(2), (4) Date: May 30, 2012

(87) PCT Pub. No.: WO2011/068209
PCT Pub. Date: Jun. 9, 2011

(65) Prior Publication Data
US 2012/0238717 A1    Sep. 20, 2012

(30) Foreign Application Priority Data

| Dec. 3, 2009 | (JP) | ................................ 2009-275841 |
| Sep. 10, 2010 | (JP) | ................................ 2010-203743 |
| Sep. 10, 2010 | (JP) | ................................ 2010-203745 |
| Sep. 10, 2010 | (JP) | ................................ 2010-203746 |
| Sep. 10, 2010 | (JP) | ................................ 2010-203769 |

(51) Int. Cl.
| C07C 43/188 | (2006.01) |
| C07C 43/178 | (2006.01) |
| C11D 3/37 | (2006.01) |
| C08F 216/14 | (2006.01) |
| C07C 217/28 | (2006.01) |
| C08F 216/12 | (2006.01) |
| C08F 290/06 | (2006.01) |
| C07D 303/24 | (2006.01) |
| C07D 303/22 | (2006.01) |
| C07D 303/20 | (2006.01) |
| C02F 1/28 | (2006.01) |

(52) U.S. Cl.
CPC ............ C07C 43/178 (2013.01); C11D 3/3746 (2013.01); C07D 303/22 (2013.01); C08F 216/1416 (2013.01); C07C 43/188 (2013.01); C07D 303/20 (2013.01); C07C 217/28 (2013.01); C08F 216/125 (2013.01); C11D 3/3757 (2013.01); C08F 290/062 (2013.01); C07D 303/24 (2013.01); C02F 1/285 (2013.01)
USPC ........... 549/518; 549/520; 549/522; 568/616; 526/273; 526/333

(58) Field of Classification Search
CPC .... C07C 43/188; C07C 217/28; C07C 69/54; C07D 303/24; C07D 303/20; C07D 303/22; C08F 216/1416; C08F 216/215; C08F 216/125; C08F 290/062
USPC .................. 526/273, 333; 549/518, 520, 522; 568/616
See application file for complete search history.

(56) References Cited

U.S. PATENT DOCUMENTS

| 2,949,474 | A | 8/1960 | Murdoch et al. |
| 6,162,563 | A | 12/2000 | Miura et al. |
| 6,239,204 | B1 | 5/2001 | Miura et al. |
| 6,403,714 | B1 * | 6/2002 | Wang et al. .................. 525/143 |
| 2002/0012849 | A1 | 1/2002 | Miura et al. |

FOREIGN PATENT DOCUMENTS

| | | |
|---|---|---|
| EP | 0838487 A2 | 4/1998 |
| EP | 0838487 A2 * | 4/1998 |
| JP | 63241026 A | 10/1988 |
| JP | 03179024 A | 8/1991 |
| JP | 2001-513750 A | 9/2001 |
| JP | 2005-170977 A | 6/2005 |
| JP | 2008-001770 A | 1/2008 |
| JP | 2008-303347 A | 12/2008 |
| JP | 2009-510175 A | 3/2009 |
| JP | 2009-208982 A | 9/2009 |
| JP | 2010-132814 A | 6/2010 |
| JP | 2010-209133 A | 9/2010 |
| SU | 1129208 A1 | 12/1984 |
| WO | WO-97/32475 A1 | 9/1997 |
| WO | WO-97/42251 A1 | 11/1997 |
| WO | WO-98/07772 A1 | 2/1998 |
| WO | WO-2004/056888 A2 | 7/2004 |
| WO | WO-2007/037469 A1 | 4/2007 |

OTHER PUBLICATIONS

English Translation of the PCT Written Opinion dated Feb. 1, 2011 issued in corresponding Appln No. PCT/JP2011/071730.
Raskulova et al., "Formation of Diol Divinyl; Diethers in the Synthesis of 1,2-Epoxy-3-(vinyloxyalkoxy)propanes", Russian Journal of Organic Chemistry, 2002, vol. 38, No. 5, pp. 754-755.
Kukharev et al., "Reaction of Glycidyl Vinyloxyalkyl Ethers with Primary Amines", Russian Journal of Organic Chemistry, 200, vol. 36, No. 4, pp. 560-564.
Zhurnal Organicheskoi Khimii, 1989, vol. 25, No. 10, pp. 2083-2089.
Kukharev et al., "Condensation of 1-Alkylamino-3-(2-Vinyloxyethoxy)propan-2-ols with Carbonyl Compounds" Russian Journal of Organic Chemistry, 2003, vol. 39, No. 11, pp. 1557-1560.
CAPLUS (STN) [online], AN 1969: 114527; CAPLUS, DN 70 I 114527.
English Translation of the PCT Written Opinion dated Feb. 1, 2011 issued in corresponding Appln No. PCT/JP2010/071703.
Raskulova et al., "Formation of Diol Divinyl; Diethers in the Synthesis of 1,2-Epoxy-3(vinyloxyalkoxy)propanes", Russian Journal of Organic Chemistry, 2002, vol. 38, No. 5, pp. 754-755.
Kukharev et al., "Reaction of Glycidyl Vinyloxyalkyl Ethers with Primary Amines", Russian Journal of Organic Chemistry, 2000, vol. 36, No. 4, pp. 560-564.
Office Action for priority JP Appln. No. 2010-203769 issued Sep. 24, 2014, with its partial English Translation.

* cited by examiner

*Primary Examiner* — Ling Choi
*Assistant Examiner* — David L Miller
(74) *Attorney, Agent, or Firm* — Novak Druce Connolly Bove + Quigg LLP

(57) ABSTRACT

A composition is provided that contains an intermediate for a water-soluble monomer, wherein this intermediate is suitable for producing a water-soluble polyalkylene glycol-type monomer that has a polymerizable terminal double bond, and suitable for the production of water-soluble polymer, and moreover allows the high-yield production of water-soluble polymer. A process of producing this composition and a water-soluble monomer-containing composition obtained therefrom are also provided. A water-soluble monomer is also provided that can be used as a starting material for a water-soluble polymer that even at high hardnesses exhibits an excellent capacity to capture metal ions such as the calcium ion and magnesium ion, an excellent anti-gelation performance, an excellent anti-soil redeposition performance, a better anti-dye transfer performance than in the past, and also an excellent compatibility with surfactants. A production process is also provided that can produce such a water-soluble monomer at higher yields and higher selectivities (higher purities) than in the past. A composition containing an intermediate for a water-soluble monomer, that contains a compound (A) having a specified structure and that contains a specified amount of a compound (B) having a specified structure. Also, a water-soluble monomer having a specified structure is provided.

9 Claims, 5 Drawing Sheets

COMPOSITION CONTAINING INTERMEDIATE FOR WATER-SOLUBLE MONOMER AND PROCESS FOR PRODUCTION THEREOF, COMPOSITION CONTAINING WATER-SOLUBLE MONOMER, INTERMEDIATE FOR WATER-SOLUBLE MONOMER, AND WATER-SOLUBLE MONOMER AND PROCESS FOR PRODUCTION THEREOF

CROSS REFERENCE TO RELATED APPLICATIONS

This application is a National Phase filing under 35 U.S.C. §371 of PCT/JP2010/071703 filed on Dec. 3, 2010; and this application claims priority to Application No. 2009-275841 filed in Japan on Dec. 3, 2009, Application No. 2010-203743 filed in Japan on Sep. 10, 2010, Application No. 2010-203745 filed in Japan on Sep. 10, 2010, Application No. 2010-203746 filed in Japan on Sep. 10, 2010, Application No. 2010-203769 filed in Japan on Sep. 10, 2010, under 35 U.S.C. §119; the entire contents of all are hereby incorporated by reference.

TECHNICAL FIELD

The present invention relates to a composition containing an intermediate for a water-soluble monomer and to a process for producing this composition, to a water-soluble monomer-containing composition obtained from the preceding, and to an intermediate for a water-soluble monomer. More particularly, the present invention relates to a composition that contains an intermediate for a water-soluble monomer, with this intermediate being suitable for use as an intermediate for producing a compound that can be a starting monomer for a water-soluble polymer; to a process for producing this composition; to a water-soluble monomer-containing composition obtained from the preceding; and to an intermediate for a water-soluble monomer. The present invention additionally relates to a water-soluble monomer and a process for the production thereof.

BACKGROUND ART

Water-soluble monomers are ordinarily used as starting materials for polymers in order to impart water solubility or water dispersibility to a polymer. Among water-soluble monomers, polyalkylene glycol-type monomers are useful industrial starting materials generally employed in industry as water-soluble monomers and, for example, when copolymerized with a carboxylic acid (salt)-type monomer, yield polymers that can be used in a wide variety of applications. Such water-soluble polymers are well suited for use as starting materials, for example, for dispersing agents, detergent compositions, scale removers, cement additives, thickeners, and so forth. Among such water-soluble monomers, polyalkylene glycol-type monomers that have a particular functional group in combination with a polymerizable double bond are receiving attention and are under development. Active investigations are underway into the functionalities that are conferred by the introduction of functional groups into the polymers obtained from such monomers.

With regard to the production of water-soluble monomer having a particular functional group, a synthetic scheme must be devised here for introducing the particular functional group in combination with the polyalkylene glycol chain, which exhibits properties such as water solubility, and several synthetic procedures have been disclosed.

For example, within the sphere of conventional processes for the synthesis of polyalkylene glycol-type monomers that have a particular functional group, and more specifically as a process for producing a polyalkylene glycol-type compound that has a specific structure and contains the carboxyl group and/or a carboxyl group salt, a process has been disclosed in which a compound provided by the addition of an alkylene oxide on an unsaturated alcohol is reacted with epichlorohydrin and the resulting reaction product is reacted with a compound that contains a particular reactive group and the carboxyl group (refer, for example, to Patent Document 1).

In addition, monomers with particular structures (refer, for example, to Patent Documents 2, 3, and 4) have been disclosed as compounds that have the same structure as the aforementioned reaction product obtained by the reaction of epichlorohydrin and a compound provided by the addition of an alkylene oxide on an unsaturated alcohol; these monomers are disclosed, for example, as a monomer component of polyether copolymers. Moreover, a monomer having a particular structure (refer, for example, to Patent Document 5) has been disclosed as a monomer component for synthesizing a specific polyether polymer having an oligooxyethylene side chain.

On the other hand, amino group-containing polymers obtained by the polymerization of amino group-containing monomer and cationic polymers obtained by the polymerization of cationic group-containing monomer, which is a type of water-soluble monomer that has a particular functional group, have heretofore been used in a broad range of fields, e.g., coagulants, flocculants, printing inks, adhesives, detergent and cleanser additives, soil conditioners (improvers), flame retardants, shampoos and hair sprays, additives for soaps and cosmetics, anion-exchange resins, dye mordants and auxiliaries for fibers and photographic films, pigment spreading agents in paper manufacturing, paper-reinforcing agents, emulsifying agents, anticorrosion agents, softeners for textiles and paper, and additives for lubricating oils.

For example, polymers having a main chain derived from a particular monomer component have been disclosed, and it has been disclosed that a copolymer from a hydrophobic comonomer and diallyldimethylammonium chloride, which is a typical cationic monomer, can be used as a laundry additive for preventing dye migration and/or dye bleeding from fibers (refer, for example, to Patent Document 6). In addition, specific modified alkyleneimine-type polymers having an alkyleneimine structural unit have been disclosed, and it has been disclosed that such polymers exhibit an excellent performance in applications such as detergents and cleansing agents (refer, for example, to Patent Document 7). It has been disclosed that a high detergency is shown by a detergent composition that contains an alkanolamine, a polymer compound containing a structural unit derived from a monomer having a vinylpyridine moiety, and prescribed amounts of a nonionic surfactant and a non-soap anionic surfactant (refer, for example, to Patent Document 8). In addition, an amino group-containing monomer has been disclosed as a special siloxane present in a composition (refer, for example, to Patent Document 9).

Sulfonic acid group-containing polymers yielded by the polymerization of a sulfonic acid group-containing monomer, which is one type of water-soluble monomer having a particular functional group, have also been used in a broad range of fields, e.g., water-treatment agents, detergent builders, detergent compositions, dispersing agents, and cleansers.

For example, polyalkylene glycol-type compounds have been disclosed that have in the molecule a terminal double bond and a particular structural moiety that contains a sulfonic acid group, and it has been disclosed that such polymers exhibit elevated properties in water-based applications such as dispersing agents and detergent builders (refer, for example to Patent Document 10).

In addition, polyalkylene glycol-type polymers produced from a polyalkylene glycol-type monomer that contains a hydrophobic moiety, which is one type of water-soluble monomer having a particular functional group, are known to exhibit—due to their ability to adsorb hydrophobic substances through hydrophobic interactions coupled with the dispersing capacity of the polyalkylene glycol chain—properties such as an excellent ability to disperse hydrophobic particles, an excellent anti-soil redeposition performance for hydrophobic soils, and an excellent detergency, and thus are known to be very suitable for use in various applications, e.g., detergent compositions, fiber-treatment agents, water-treatment agents, and various dispersing agents for, e.g., pigments. The following, for example, have been disclosed as such monomers: polyalkylene glycol-type monomer that has a polyalkylene glycol chain and a polymerizable double bond originating from allyl glycidyl ether and that has a hydrophobic moiety in the polyalkylene glycol chain and/or at a terminal of the chain, and polyalkylene glycol-type monomer that has a polyalkylene glycol chain and a polymerizable double bond originating from isoprenol, allyl alcohol, or methallyl alcohol and that has a hydrophobic moiety originating from $C_{1-20}$ glycidyl ether in the polyalkylene glycol chain and/or at a terminal of the chain. A process has been disclosed for producing these polyalkylene glycol-type monomers in which a $C_{1-20}$ glycidyl ether is reacted with an adduct provided by the addition of a polyalkylene glycol chain to isoprenol, allyl alcohol, or methallyl alcohol (refer, for example, to Patent Document 11).

The properties required of a laundry additive (detergent additive) have been changing over the last few years due to rising consumer awareness with regard to environmental issues. Thus, the use of residual bath water for doing laundry has become an established laundry practice with the goal of water conservation. This results in problems such as the attachment of soil components present in the residual bath water to fabric during laundering and the concentration of hard water components due to reheating of the bath, and as a consequence there are now even more demanding requirements on the anti-gelation performance and the capacity to capture the metal ions, e.g., the calcium ion, magnesium ion, and so forth, present in the water that cause a deterioration in the detergency, and on the capacity to inhibit the re-attachment of soil components to fabric during the laundry process ("anti-soil redeposition performance"), even in the presence of higher hardnesses. Moreover, the number of households that use a drum washing machine is increasing as consumers seek to conserve water and reduce the amount of waste water. A better capacity to inhibit dye transfer (anti-dye transfer performance) is then required since doing laundry under water-conserving conditions makes fabric-to-fabric dye migration during the laundry process an even bigger problem than before.

Furthermore, the detergents that are undergoing an increase in current demand due most importantly to their suitability for use in drum washing machines are liquid detergent concentrates in which the content of liquid detergent, and particularly surfactant, is 50% or more. As a consequence, a detergent additive must be well adapted for incorporation in such a liquid detergent concentrate and detergent additives must therefore exhibit a better compatibility with surfactants than in the past.

[Patent Document 1] Japanese Patent Application Laid-open No. 2010-132814 (pages 1-2, 15-17)
[Patent Document 2] European Patent Application No. 838,487 (pages 1-2)
[Patent Document 3] Domestic Republication of PCT International Application WO 98/007772 (page 47)
[Patent Document 4] Domestic Republication of PCT International Application WO 97/042251 (page 50)
[Patent Document 5] Japanese Patent Application Laid-open No. S63-241026 (pages 1-2)
[Patent Document 6] WO 04/056888 (pages 6-7, 37)
[Patent Document 7] Japanese Patent Application Laid-open No. 2005-170977 (pages 2-3)
[Patent Document 8] Japanese Patent Application Laid-open No. 2008-1770 (pages 2-3)
[Patent Document 9] WO 97/32475 (page 19)
[Patent Document 10] Japanese Patent Application Laid-open No. 2008-303347 (pages 2, 8)
[Patent Document 11] Published Japanese Translation of PCT Application No. 2009-510175 (pages 2, 11)

Based on the current circumstances as described above, various investigations have been carried out into polymers that can also be used in the previously described detergent compositions and into water-soluble monomers that are starting materials for such polymers. For example, investigations have been carried out, as in the previously indicated Patent Document 1, into processes for producing water-soluble polyalkylene glycol-type monomers, but there was still room for additional improvements in order to achieve even better use as a polymerization starting material for various polymers.

Thus, a water-soluble monomer preferably has a polymerizable double bond at a terminal and suitably also has a particular functional group at another terminal. This serves to secure polymerizability for the monomer while positioning the particular functional group, once the polymer has been formed, at a terminal of the polymer side chain and thus has the advantage of a facile manifestation of properties deriving from the particular functional group.

Investigations have thus been carried out into the production of water-soluble monomers that have such a structure. However, when a water-soluble polymer was produced by polymerizing a water-soluble monomer in the form of a polyalkylene glycol-type monomer that had a polymerizable terminal double bond and a functional group at another terminal and that exhibited water solubility due to the polyalkylene glycol chain, it was found that gelation ended up occurring and the yield of the water-soluble polymer was lowered.

The production of such a polyalkylene glycol-type monomer requires an intermediate that is a precursor for the monomer, and it was discovered that this intermediate influences the polymerization properties of the obtained water-soluble monomer and that problems that produce defects during production of the water-soluble polymer reside here.

In addition, as noted above, despite the various water-soluble polymers that have heretofore been reported, these have been concerned with the properties for the water-based applications described above, and it cannot be said, for example, that they can necessarily fully satisfy the most recent demanding requirements, e.g., the needs of users for polymers that demonstrate a high anti-dye transfer performance when used as a detergent additive, and there has been room for additional improvements with regard to polymers that can respond to these new needs and exhibit higher property levels and are well-adapted for applications such as detergent additive applications.

Otherwise, investigations as in the previously indicated Patent Document 11 have been carried out on processes for producing a polyalkylene glycol-type monomer that contains a hydrophobic moiety. However, when the production process disclosed in Patent Document 11 is used, secondary products are produced when two or more molecules of the $C_{1-20}$ glycidyl ether react with the monomer having a polyalkylene glycol chain and a polymerizable double bond, which results in the problems of a diminished reaction selectivity and a reduction in the purity of the obtained polyalkylene glycol-type monomer. And as a result, the properties of the polyalkylene glycol-type polymer yielded by the polymerization of the thusly obtained polyalkylene glycol-type monomer may not be satisfactorily manifested.

DISCLOSURE OF THE INVENTION

The present invention was achieved in view of the current conditions described above and takes as an object the introduction of a composition containing an intermediate for a water-soluble monomer, wherein this intermediate is well adapted for producing a water-soluble polyalkylene glycol-type monomer that has a polymerizable terminal double bond, is well adapted for the production of water-soluble polymer, and makes possible the high-yield production of water-soluble polymer. Further objects of the present invention are the introduction of a process of producing this composition and the introduction of a water-soluble monomer-containing composition obtained from the preceding. An additional object of the present invention is the introduction of a water-soluble monomer that can be used as a starting material for a water-soluble polymer that exhibits excellent properties, even at high hardnesses, such as an excellent capacity to capture metal ions such as the calcium ion and magnesium ion, an excellent anti-gelation performance, an excellent anti-soil redeposition performance, a better anti-dye transfer performance than in the past, and also an excellent compatibility with surfactants. Yet a further object of the present invention is a production process that can produce such a water-soluble monomer at higher yields and higher selectivities (higher purities) than in the past.

The inventor first ascertained that—when a water-soluble polymer is produced by the polymerization of a polyalkylene glycol-type monomer as a water-soluble monomer that has a polymerizable terminal double bond and a particular functional group and that exhibits water solubility due to a polyalkylene glycol chain—the yield of the water-soluble polymer declines due to the occurrence of the gelation cited above. The inventor also considered the intermediate used to synthesize the polyalkylene glycol-type monomer and discovered that when this intermediate is produced a secondary product having a particular structure that has two unsaturated bonds in the structure is produced at the same time, and also discovered that this secondary product acts as a crosslinking component during production of the water-soluble polymer and is a major cause of gelation. The inventor carried out various investigations into the content of this particular secondary product and discovered that the gelation reaction during the polymerization reaction can be thoroughly inhibited and a water-soluble polymer can be produced in good yields when the water-soluble polymer is produced by bringing the content of the compound having this particular structure in the intermediate-containing composition into a specific range and deriving the monomer from this intermediate-containing composition. Moreover, it was also discovered that when the content of the compound having this particular structure is brought into a specific range, not only can the water-soluble polymer be produced in good yields, but an additional capacity to adsorb to soil or fabric can be imparted to the produced water-soluble polymer and novel functionalities can be provided, e.g., a polymer can be made that has a low viscosity even when the polymer has a high molecular weight.

Thus, with regard to a composition containing an intermediate for a water-soluble monomer, the inventor came to the idea that, by bringing the content of a specific component into a specific range and by having a specific content of the intermediate, the previously described problems can be thoroughly solved and novel functionalities can also be imparted to the water-soluble polymer obtained from such an intermediate-containing composition.

In order to achieve the objects indicated above, the inventor carried out additional investigations into water-soluble monomers that were starting materials for various water-soluble polymers/copolymers. It was discovered as a result that a polymer prepared from a water-soluble monomer having a particular structure, when used, for example, as a detergent additive, exhibits excellent properties even at high hardnesses, i.e., an excellent anti-gelation capacity and an excellent capacity to capture metal ions, e.g., the calcium ion, magnesium ion, and so forth, an excellent anti-soil redeposition performance, a better anti-dye transfer performance than in the past, and also an excellent compatibility with surfactants, and exhibits the properties required for application as a detergent additive to an excellent degree. This was considered to completely solve the previously indicated problems and the present invention was achieved as a result.

In addition, upon the occasion of carrying out investigations into a process for producing various water-soluble monomers in order to solve the problems described above, the inventor discovered that a water-soluble monomer can be produced at high yields and high selectivities (high purities) without producing secondary products, by reacting a glycidyl group-containing polyalkylene glycol-type compound with a functional group-containing compound. This was considered to completely solve the previously indicated problems and the present invention was achieved as a result.

Thus, the present invention is a composition containing an intermediate for a water-soluble monomer, that contains a compound (A) represented by the following general formula (1)

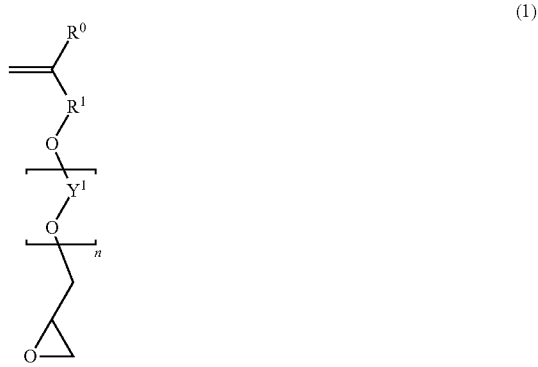

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$)

and represents a number from 1 to 300), wherein the composition further contains a compound (B) represented by the following general formula (2)

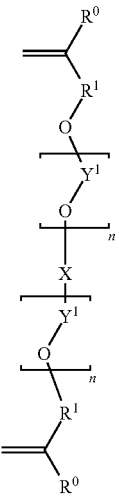
(2)

(where, each $R^0$ is the same or different from one another and represents the hydrogen atom or a methyl group; each $R^1$ is the same or different from one another and represents a methylene group, an ethylene group, or a direct bond; X represents —$CH_2$—CH(OR')—$CH_2$—O— or a direct bond; R' represents a hydrogen atom or a glycidyl group; each $Y^1$ is the same or different from one another and represents a $C_{2-20}$ alkylene group; and n is the average number of moles of addition of the oxyalkylene group (—$Y^1$—O—) and each n is the same or different from one another and represents a number from 1 to 300), the compound (B) content is 0.1 to 6.0 mol % with reference to the compound (A) content, and the compound (A) content is 50 to 100 mass % on the basis of 100 mass % of the nonvolatile fraction of the composition containing an intermediate for a water-soluble monomer.

The present invention is also a water-soluble monomer represented by the following general formula (11)

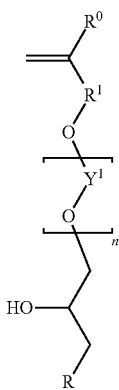
(11)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group (—$Y^1$—O—) and represents a number from 1 to 300; and R represents any of the following structures with general formulas (7) to (9))

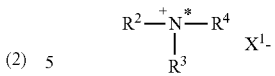
(7)

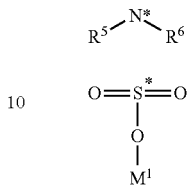
(8)

(9)

wheres, the * indicates that the atom bearing the * is bonded to the carbon atom that is bonded to R in general formula (11); $R^2$, $R^3$, $R^4$, $R^5$, and $R^6$ are the same or different from one another and represent a hydrogen atom or a $C_{1-20}$ organic group; $R^2$ and $R^3$ may be bonded to each other to form a ring structure; $R^5$ and $R^6$ may be bonded to each other to form a ring structure; $X^1$— represents a counteranion; and $M^1$ represents a hydrogen atom or a monovalent cation.

The present invention is also a process of producing a water-soluble monomer represented by the following general formula (6)

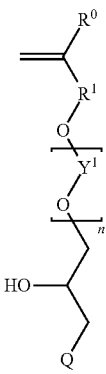
(6)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group (—$Y^1$—O—) and represents a number from 1 to 300; and Q represents any of the structures with the general formulas (7) to (10) given below), the production process comprising:
(i) one of a step of reacting a compound (I) represented by the following general formula (I)

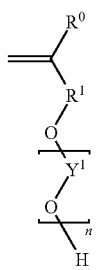
(I)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300) and an epihalohydrin and an alkali compound and a step of reacting a compound (I) represented by the preceding general formula (I) and an epihalohydrin in the presence of a catalyst; and (ii) a step of reacting the product obtained in step (i) with a tertiary amine salt, secondary amine, sulfurous acid compound, or hydroxyl group-containing compound or a step of reacting the product obtained in step (i) with a secondary amine and reacting the product obtained by this reaction with a quaternizing agent;

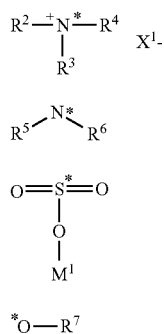

(7)

(8)

(9)

(10)

where, the * indicates that the atom bearing the * is bonded to the carbon atom that is bonded to Q in general formula (6); $R^2$, $R^3$, $R^4$, $R^5$, and $R^6$ are the same or different from one another and represent a hydrogen atom or a $C_{1-20}$ organic group; $R^2$ and $R^3$ may be bonded to each other to form a ring structure; $R^5$ and $R^6$ may be bonded to each other to form a ring structure; $X^1-$ represents a counteranion; $M^1$ represents a hydrogen atom or a monovalent cation; and $R^7$ represents a $C_{1-20}$ organic group.

The present invention is explained in detail in the following.

The composition according to the present invention containing an intermediate for a water-soluble monomer contains a compound (A) represented by the following general formula (1)

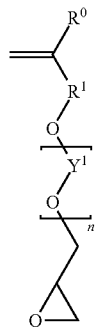

(1)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300) and also contains a compound (B) represented by the following general formula (2)

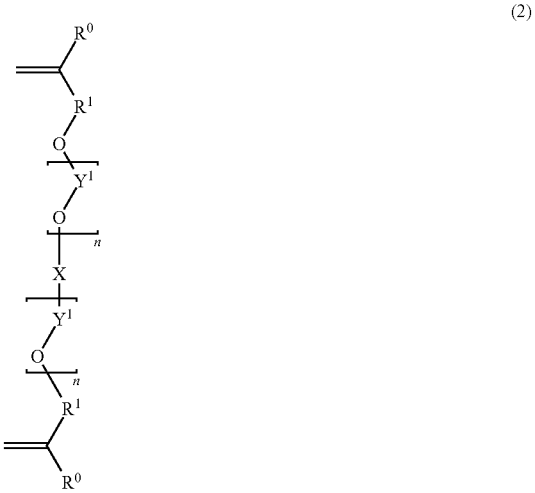

(2)

(where, each $R^0$ is the same or different from one another and represents the hydrogen atom or a methyl group; each $R^1$ is the same or different from one another and represents a methylene group, an ethylene group, or a direct bond; X represents $-CH_2-CH(OR')-CH_2-O-$ or a direct bond; $R^1$ represents a hydrogen atom or a glycidyl group; each $Y^1$ is the same or different from one another and represents a $C_{2-20}$ alkylene group; and n is the average number of moles of addition of the oxyalkylene group ($-Y^1-O-$) and each n is the same or different from one another and represents a number from 1 to 300). A single species or two or more species of each of these may be present. This intermediate-containing composition must contain compounds (A) and (B), but may contain other components.

Compound (A) is a glycidyl group-containing polyalkylene glycol-type compound represented by the following general formula (1)

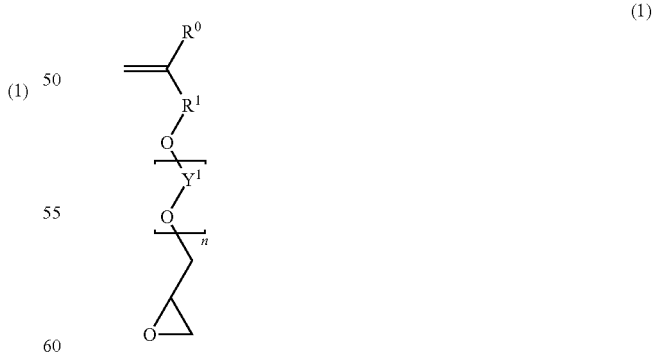

(1)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300), and this compound can be converted by suitable modification of the terminal glycidyl group into a compound having any of various functional groups. In addition, such a compound having any of various functional groups can be polymerized via the polymerizable carbon-carbon double bond to provide a polymer that has the functional group in terminal position on the side chain and that exhibits water solubility due to the side chain oxyalkylene group. Moreover, when, for example, this functional group-containing compound is copolymerized with an acrylic ester, the functional group originating from the acrylic ester and the functional group at the side chain terminal originating from the functional group-containing compound will be present in the resulting copolymer at positions separated in the copolymer structure by the side chain oxyalkylene group, and it can be anticipated that novel properties may be imparted to the resulting copolymer arising from the positional relationship between these functional groups. Thus, compound (A) is a compound useful as an intermediate for water-soluble monomers, that forms the foundation for the synthesis of monomers that can be used to synthesize water-soluble polymers having various functional groups in pendant terminal position.

Thus, an intermediate for a water-soluble monomer, the intermediate being represented by the following general formula (1)

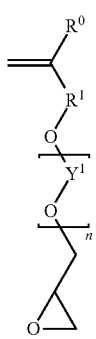

(1)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300), is also one of the inventions disclosed herein.

With regard to the synthesis of monomer that can be used to synthesize water-soluble polymer having any of various functional groups in pendant terminal position, the aforementioned intermediate for a water-soluble monomer can be used as an intermediate for the synthesis of this monomer, but the polymer may also be synthesized by the polymerization of this intermediate itself. That is, this intermediate for a water-soluble monomer can also be used as a monomer for polymer synthesis. Accordingly, a polymer can also be synthesized using the composition of the present invention containing an intermediate for a water-soluble monomer, that contains the aforementioned intermediate for a water-soluble monomer, and this composition can thus also be used as a monomer-containing composition.

$R^0$ in general formula (1) represents a hydrogen atom or a methyl group, while $R^1$ represents a methylene group, ethylene group, or direct bond.

When in the present Specification this $R^1$ represents a direct bond, the $H_2C=C(R^0)-R^1-O-$ structure in general formula (1) then represents a structure given by $H_2C=C(R^0)-O-$. Thus, $H_2C=C(R^0)-R^1-$ denotes the methallyl group when $R^0$ is a methyl group and $R^1$ is a methylene group; the isoprenyl group when $R^0$ is a methyl group and $R^1$ is an ethylene group; the isopropenyl group when $R^0$ is a methyl group and $R^1$ is a direct bond; the allyl group when $R^0$ is a hydrogen atom and $R^1$ is methylene; the butenyl group when $R^0$ is a hydrogen atom and $R^1$ is an ethylene group; and the vinyl group when $R^0$ is a hydrogen atom and $R^1$ is a direct bond.

Viewed in terms of polymerizability, isoprenyl, methallyl, allyl, and vinyl groups are preferred for $H_2C=C(R^0)-R^1-$ in general formula (1), i.e., the group bearing the carbon-carbon double bond that undergoes polymerization when the monomer derived from compound (A) is polymerized. The isoprenyl group, methallyl group, and allyl group are more preferred. Because the risk of gelation increases as the polymerizability increases, the isoprenyl group and methallyl group are particularly preferred since they have the greatest ability to inhibit gelation in the present invention.

Each $Y^1$ in general formula (1) is the same or different from one another and represents a $C_{2-20}$ alkylene group, and $Y^1$ is preferably an ethylene, propylene, or butylene group because this improves the water solubility of the monomer derived from compound (A), while ethylene and propylene are particularly preferred.

This alkylene group may be a single species or may be two or more species. When two or more species are present, the oxyalkylene structure of ($-Y^1-O-$) may be a random sequence, an alternating sequence, or a block sequence.

n in general formula (1) is the average number of moles of addition of the oxyalkylene group ($-Y^1-O-$) and represents a number from 1 to 300, wherein n is preferably at least 2. When the average number of moles of addition of the oxyalkylene group ($-Y^1-O-$) in compound (A) is in the indicated range, compound (A), and also the monomer derived from compound (A), ends up having a high boiling point, and as a result compound (A), or the monomer derived from compound (A), cannot be purified by, for example, distillation, and it is thus quite difficult to carry out separation from the secondary products that are simultaneously produced during the synthesis of compound (A). As a consequence, the effects of the present invention—i.e., enabling the high-yield production of water-soluble polymer obtained by using the composition according to the present invention containing an intermediate for a water-soluble monomer wherein this composition has a particular value for the content of a particular component among the produced secondary products—are more substantially manifested when n in general formula (1) has a large value and purification of the compound (A) is thus problematic. This n more preferably is at least 5. Moreover, n is preferably at least 2 also from the perspective of the ease of handling deriving from the water solubility and fluidity of the monomer derived from compound (A). At least 5 is more preferred and at least 10 is even more preferred. At least 20 is particularly preferred. In addition, n is preferably not more than 200, more preferably not more than 150, even more preferably not more than 120, and particularly preferably not more than 100, because this provides an excellent polymerizability for the monomer derived from compound (A). Not more than 50 is most preferred.

The compound (A) used in the present invention can be synthesized, as described below, using an epihalohydrin and a compound represented by the following general formula (1)

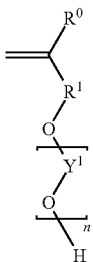

(I)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300) as reactants; however, the compound (B) represented by the following general formula (2)

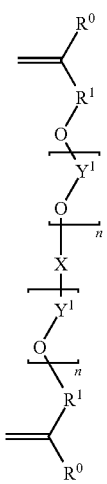

(2)

(where, each $R^0$ is the same or different from one another and represents the hydrogen atom or a methyl group; each $R^1$ is the same or different from one another and represents a methylene group, an ethylene group, or a direct bond; X represents $-CH_2-CH(OR')-CH_2-O-$ or a direct bond; R' represents a hydrogen atom or a glycidyl group; each $Y^1$ is the same or different from one another and represents a $C_{2-20}$ alkylene group; and n is the average number of moles of addition of the oxyalkylene group ($-Y^1-O-$) and each n is the same or different from one another and represents a number from 1 to 300) is produced as one type of secondary product during this reaction. This compound (B) has a structure provided by the dimerization of the compound (I) reactant across the group represented by X in general formula (2), and the $R^0$, $R^1$, $Y^1$, and n in general formula (2) are thus the same as the $R^0$, $R^1$, $Y^1$, and n in general formula (1).

X in general formula (2) represents $-CH_2-CH(OR')-CH_2-O-$ or a direct bond wherein R' represents the hydrogen atom or the glycidyl group. The secondary products encompassed by compound (B) can be exemplified by the compound (B-1) represented by the following general formula (3) wherein X is $-CH_2-CH(OH)-CH_2-O-$

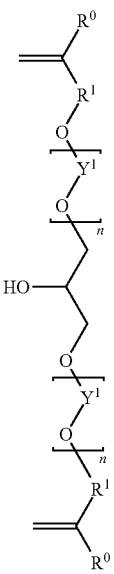

(3)

($R^0$, $R^1$, $Y^1$, and n in the formula are the same as in general formula (2)), the compound (B-2) represented by the following general formula (4) wherein X is $-CH_2-CH(OR'')-CH_2-O-$ (R'' here is the glycidyl group)

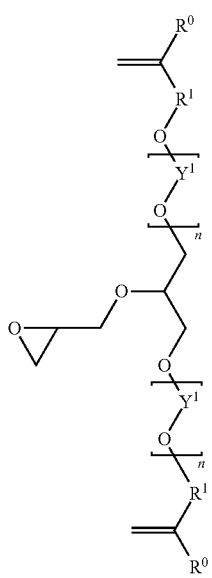

(4)

($R^0$, $R^1$, $Y^1$, and n in the formula are the same as in general formula (2)), and the compound (B-3) represented by the following general formula (5) wherein X is a direct bond

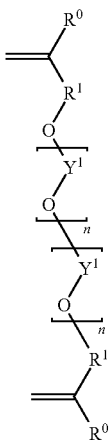

(5)

($R^0$, $R^1$, $Y^1$, and n in the formula are the same as in general formula (2)). Compound (B-1) is a compound produced during the synthesis of compound (A) from compound (I) and an epihalohydrin and is produced by the reaction of the compound (I) reactant and the compound (A) reaction product; compound (B-2) is a compound produced by the reaction of epihalohydrin with the compound (B-1) produced as a secondary product; and compound (B-3) is a compound produced by the dimerization of the compound (I) reactant.

The compound (B) content in the composition according to the present invention containing an intermediate for a water-soluble monomer is 0.1 to 6.0 mol % with reference to the compound (A) content, and the compound (A) content in the composition is 50 to 100 mass % on the basis of 100 mass % of the nonvolatile fraction of the composition containing an intermediate for a water-soluble monomer. This nonvolatile fraction in the composition containing an intermediate for a water-soluble monomer denotes the component that does not evaporate under conditions of 1 hour at 1 atmosphere and 130° C. Thus, in an embodiment in which a solvent is present in the composition, the solvent, e.g., water, that evaporates under the indicated conditions is not included. This indicates, among compositions in which compound (A) is substantially present, a composition in which the content of compound (B), which is one of the secondary products simultaneously produced during compound (A) synthesis, has been brought to a prescribed value. When a polymer is obtained by deriving a water-soluble monomer using the composition according to the present invention containing an intermediate for a water-soluble polymer and polymerizing this water-soluble monomer, the gelation of the water-soluble polymer during the polymerization reaction can be substantially inhibited by controlling the compound (B) content in the composition to the indicated level. Novel functionalities can also be imparted to the water-soluble polymer, such as providing the produced water-soluble polymer with the ability to adsorb to dirt or fabric and enabling the preparation of a low-viscosity polymer even when the polymer has a high molecular weight. This is hypothesized to occur for the following reason: by having the composition contain the optimal amount of compound (B), which can act as a crosslinking component during production of the water-soluble polymer because it has two unsaturated bonds in its structure, the produced water-soluble polymer becomes a partially crosslinked graft polymer. For example, by providing the thusly produced water-soluble polymer with the capacity to adsorb to dirt, when this water-soluble polymer is incorporated in, for example, a detergent composition, a detergent composition can be provided that effectively prevents the re-attachment of dirt to clothing because the polymer component adsorbs to dispersed dirt. Thus, a high performance water-soluble polymer can be produced in high yields by having the compound (B) content in the composition containing an intermediate for a water-soluble monomer be in a prescribed range. Expressed with reference to the compound (A) content, the compound (B) content is preferably 0.3 to 4.5 mol % and more preferably is 0.5 to 3.0 mol % and particularly preferably is 0.7 to 2.5 mol % because this provides the greatest ability to impart functionality to the produced water-soluble polymer.

When the compound (A) content is 50 to 100 mass % on the basis of 100 mass % of the nonvolatile fraction of the composition containing an intermediate for a water-soluble monomer, sufficient compound (A) is then present in terms of providing a composition containing an intermediate for a water-soluble monomer and the compound (A) content is satisfactory for the purpose of deriving a water-soluble monomer using the composition of the present invention containing an intermediate for a water-soluble monomer. The compound (A) content is preferably 55 to 95 mass % and more preferably is 60 to 90 mass %.

It is also a preferred embodiment of the present invention that the compound (B) content in the composition of the present invention containing an intermediate for a water-soluble monomer is 0.1 to 5.0 mol % with reference to the sum of compound (A) and compound (I), the latter being a reactant for the synthesis of compound (A). That is, with compound (A) being obtained by reacting an epihalohydrin and a compound (I) represented by the following general formula (I)

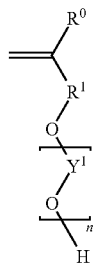

(I)

(where, $R^0$ represents a hydrogen atom or a methyl group; $R^1$ represents a methylene group, an ethylene group, or a direct bond; each $Y^1$ is the same or different from one another and represents a $C_{2\text{-}20}$ alkylene group; and n is the average number of moles of addition of the oxyalkylene group (—$Y^1$—O—) and represents a number from 1 to 300), it is also a preferred embodiment of the present invention that the composition containing an intermediate for a water-soluble monomer have a compound (B) content of 0.1 to 5.0 mol % with reference to the total content of compound (A) and compound (I) and have a total content of compound (A) and compound (I) of 50 to 100 mass % on the basis of 100 mass % of the nonvolatile fraction in the composition containing an intermediate for a water-soluble monomer. In addition, the compound (B) content, expressed with reference to the total content of compound (A) and compound (I), is preferably 0.25 to 4.0 mol % and more preferably is 0.35 to 3.0 mol % and particularly preferably is 0.5 to 2.0 mol % because this provides the greatest ability to impart functionality to the produced water-soluble polymer.

When the total content of compound (A) and compound (I) is 50 to 100 mass % on the basis of 100 mass % of the nonvolatile fraction of the composition containing an intermediate for a water-soluble monomer, compound (A) and compound (I) are then present in appropriate amounts in terms of providing a composition containing an intermediate for a water-soluble monomer and in appropriate amounts for the purpose of deriving a water-soluble monomer using the composition of the present invention containing an intermediate for a water-soluble monomer. The total content of compound (A) and compound (I) is preferably 60 to 98 mass % and more preferably is 70 to 96 mass %.

The process of producing the compound (A)-containing composition containing an intermediate for a water-soluble monomer will now be described in detail.

The compound (A)-containing composition containing an intermediate for a water-soluble monomer can be obtained by reacting compound (I) and an epihalohydrin at a molar ratio of 1/2 to 1/15 (hydroxyl group (as the hydroxyl value) present in compound (I)/epihalohydrin). Thus, one of the inventions disclosed herein is a process of producing a composition containing an intermediate for a water-soluble monomer, wherein the composition contains a compound (A) represented by the following general formula (1)

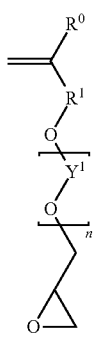

(1)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300), the production process comprising:

a step of reacting a compound (I) represented by the following general formula (I)

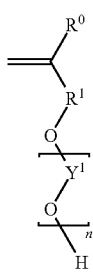

(I)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group ($-Y^1-O-$) and represents a number from 1 to 300) and an epihalohydrin at a molar ratio of 1/2 to 1/15 (hydroxyl group present in compound (I)/epihalohydrin).

The process of the present invention for producing a composition containing an intermediate for a water-soluble monomer must contain the reaction step described above, but may also contain other steps.

The aforementioned reaction step can be carried out by a reaction process as ordinarily used for the reaction of a compound (I) and an epihalohydrin, but is preferably carried out using the following reaction step (i-a) or (i-b): (i-a) a step of reacting the compound (I) and the epihalohydrin in the presence of an alkali compound; (i-b) a step of adding an epihalohydrin and a Lewis acid catalyst to a compound (I), reacting, and then adding an alkali compound and reacting. Thus, it is also a preferred embodiment of the present invention that the aforementioned reaction step includes a step of reacting the compound (I) and epihalohydrin in the presence of an alkali compound. It is also a preferred embodiment of the present invention that the aforementioned reaction step include a step of adding an epihalohydrin and a Lewis acid catalyst to a compound (I), reacting, and then adding an alkali compound and reacting. Of these reaction steps, the compound (A)-containing composition containing an intermediate for a water-soluble monomer is preferably produced by the process of reaction step (i-a) from the standpoint of inhibiting secondary reactions, such as the decomposition during the reaction step of compound (I) due to the effect of, e.g., the catalyst.

The $R^0$, $R^1$, $Y^1$, and n in the compound (I) represented by general formula (I) are the same as the $R^0$, $R^1$, $Y^1$, and n in the synthesized compound (A). A single species of compound (I) can be used by itself or two or more species of compound (I) can be used in combination.

Compound (I) can be produced by the addition, by a typically used process, of an alkylene oxide on an alkylene glycol monovinyl ether, (meth)allyl alcohol, isoprenol, or these alcohols having an alkylene oxide adduct structure. The produced compound (I) may be subjected to a step, such as a pretreatment, prior to the aforementioned reaction step, in order to remove, e.g., the acid or alkali present and the catalyst used during compound (I) production, or this step may be omitted.

There are no particular limitations on the procedure for adding compound (I) to the reaction system, and compound (I) may be added at one time prior to the reaction or during the reaction or may be added intermittently over a plurality of times prior to the reaction and/or during the reaction.

The epihalohydrin is preferably represented by the following general formula (II)

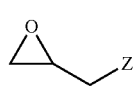

(II)

(Z in the formula represents a halogen atom) and can be exemplified by epichlorohydrin, epibromohydrin, and epiiodohydrin. Epichlorohydrin is particularly preferred among the preceding for its low cost on an industrial basis.

A single one of these epihalohydrins may be used by itself or two or more may be used in combination.

Compound (I) and the epihalohydrin are used in amounts that provide a molar ratio therebetween of 1/2 to 1/15 (hydroxyl group (as the hydroxyl value) in compound (I)/epihalohydrin), and the production of secondary products, such as the aforementioned compound (B-1) and compound (B-2), can be inhibited by reacting compound (I) and the epihalohydrin at such a molar ratio. Compound (I) and the epihalohydrin are used in amounts whereby their molar ratio is preferably 1/2.5 to 1/12 (hydroxyl group in compound (I)/epihalohydrin), more preferably 1/3 to 1/10, and even more preferably 1/4 to 1/7.

There are no particular limitations on the procedure for adding the epihalohydrin to the reaction system, and the epihalohydrin may be added at one time prior to the reaction or during the reaction or may be added intermittently over a plurality of times prior to the reaction and/or during the reaction.

The aforementioned reaction step (i-a) includes a step of reacting compound (I) and the epihalohydrin in the presence of an alkali compound. The reaction formula for the reaction in reaction step (i-a) is shown in FIG. 1. It may be understood from FIG. 1 that reaction step (i-a) produces compound (A) as product and the aforementioned compounds (B-1) and (B-2) as secondary products.

There are no particular limitations on the alkali compound, but alkali metal hydroxides such as sodium hydroxide and potassium hydroxide are preferred. A single one of these alkali compounds may be used by itself or two or more may be used in combination.

With regard to the amount of use of this alkali compound, because the presence in the reaction system of too much alkali compound causes the reaction to proceed rapidly, which may result in the production of large amounts of the compound (B) secondary product along with the production of compound (A), and because the presence of too little alkali compound in the reaction system may result in an inadequate manifestation of the effect from the addition of the alkali compound, the molar ratio between the hydroxyl group (as the hydroxyl value) in compound (I) and the alkali compound is preferably 15/1 to 1/15 (hydroxyl group in compound (I)/alkali compound). 5/1 to 1/5 is more preferred and 3/1 to 1/3 is even more preferred.

There are no particular limitations on the procedure for adding the alkali compound to the reaction system, and the alkali compound may be added at one time prior to the reaction or during the reaction or may be added intermittently over a plurality of times prior to the reaction and/or during the reaction. The form at the time of addition may be that of an aqueous solution or may be a flake shape without dissolution in a solvent. However, because the compound (A) synthesis reaction can be made to proceed gradually and the amount of secondarily produced crosslinking component can be controlled into the prescribed range by having an alkali compound concentration be present in the reaction system over the entire reaction while avoiding a transiently overly high concentration, the procedure of adding over a plurality of times is preferred among the addition procedures cited above. The dropwise addition of the aqueous solution is more preferred.

When addition in the form of the aqueous solution is carried out, the reaction may be run while removing the water (including the water secondarily produced accompanying the progress of the reaction) by an ordinarily used method.

With regard to the amount of use of the epihalohydrin in the reaction step (i-a), the molar ratio between the hydroxyl group (as the hydroxyl value) in compound (I) and the epihalohydrin is, within the previously cited ratio, preferably 1/2.5 to 1/12 (hydroxyl group in compound (I)/epihalohydrin). 1/3 to 1/10 is more preferred and 1/4 to 1/7 is even more preferred.

This reaction step (i-a) is preferably carried out as necessary using a phase-transfer catalyst. There are no particular limitations on this phase-transfer catalyst, and it can be exemplified by quaternary ammonium chloride salts such as tetramethylammonium chloride, tetraethylammonium chloride, tetrapropylammonium chloride, tetrabutylammonium chloride, tetraoctylammonium chloride, benzyltrimethylammonium chloride, benzyltriethylammonium chloride, octyltrimethylammonium chloride, and cetyltrimethylammonium chloride; tertiary ammonium chloride salts such as trimethylammonium chloride and triethylammonium chloride; quaternary ammonium bromide salts such as tetramethylammonium bromide, tetraethylammonium bromide, tetrapropylammonium bromide, tetrabutylammonium bromide, tetraoctylammonium bromide, benzyltrimethylammonium bromide, benzyltriethylammonium bromide, octyltrimethylammonium bromide, and cetyltrimethylammonium bromide; tertiary ammonium bromide salts such as trimethylammonium bromide and triethylammonium bromide; phosphonium salts such as tetrabutylphosphonium chloride and tetrabutylphosphonium bromide; and crown ethers such as 15-crown-5 and 18-crown-6. Among the preceding, tetramethylammonium chloride, tetraethylammonium chloride, tetrabutylammonium chloride, tetramethylammonium bromide, tetraethylammonium bromide, and tetrabutylammonium bromide are preferred; tetramethylammonium chloride, tetraethylammonium chloride, and tetrabutylammonium bromide are more preferred; and tetrabutylammonium bromide is even more preferred. A single one of these phase-transfer catalysts may be used by itself or two or more may be used in combination.

When a phase-transfer catalyst is used, a satisfactory catalytic effect may not be obtained when too little phase-transfer catalyst is used. When too much is used, an effect may not be obtained in conformity to the amount of use, making this economically disadvantageous. For these reasons, the molar ratio between the hydroxyl group (as the hydroxyl value) present in compound (I) and the phase-transfer catalyst is preferably 1/0.0001 to 1/0.3 (hydroxyl group in compound (I)/phase-transfer catalyst). 1/0.001 to 1/0.2 is more preferred and 1/0.005 to 1/0.1 is even more preferred.

Suitable combinations of the preferred procedures for addition described above for each component may be used as the procedure for adding the individual reactants in reaction step (i-a). The following is suitable among the various possibilities: a procedure in which compound (I) and the epihalohydrin are introduced all at once prior to the reaction and the alkali compound is added dropwise in the form of the aqueous solution during the reaction or is added intermittently in flake form a plurality of times during the reaction.

The reaction step (i-b) comprises a step in which an epihalohydrin and a Lewis acid catalyst are added to the compound (I) and a reaction is carried out and the alkali compound is then added and a reaction is carried out. The reaction formula for the reactions in this reaction step (i-b) is shown in FIG. 2. Z in FIG. 2 represents the halogen atom derived from the epihalohydrin. It may be understood from FIG. 2 that the compound (B-3) is produced as a secondary product in reaction step (i-b) along with the compound (A) product.

The Lewis acid used here may be the usual Lewis acids and is not otherwise particularly limited and can be exemplified by boron trifluoride, tin tetrachloride, tin dichloride, zinc chloride, ferric chloride, aluminum chloride, titanium tetrachloride, magnesium chloride, and antimony pentachloride.

Boron trifluoride, tin tetrachloride, and tin dichloride are preferred among the preceding. A single one of these Lewis acid catalysts may be used by itself or two or more may be used in combination.

With regard to the amount of use of this Lewis acid catalyst, a satisfactory catalytic effect may not be obtained when too little is used, while an effect may not be obtained in conformity to the amount of use when too much is used, making this economically disadvantageous. For these reasons, the molar ratio between the hydroxyl group (as the hydroxyl value) in compound (I) and the Lewis acid catalyst is preferably 1/0.0001 to 1/0.1 (hydroxyl group in compound (I)/Lewis acid catalyst). 1/0.0005 to 1/0.05 is more preferred and 1/0.001 to 1/0.03 is even more preferred.

The amount of use of the epihalohydrin in reaction step (i-b) is the same as the amount of use for the epihalohydrin in reaction step (i-a). Moreover, the alkali compound added in reaction step (i-b) is also the same as the alkali compound in reaction step (i-a).

With regard to the amount of use of the alkali compound in reaction step (i-b), the molar ratio between the halogen group in the reaction product obtained by adding the epihalohydrin and Lewis acid to compound (I) and reacting and the alkali compound is preferably 1/1 to 1/100 (halogen group/alkali compound). 1/1 to 1/50 is more preferred and 1/1 to 1/20 is even more preferred.

The reactions in reaction steps (i-a) and (i-b) proceed in good yields when run in the absence of solvent and as a consequence they are preferably run without using a solvent based on a consideration of the volumetric efficiency. However, they can also be run in the presence of a solvent. This solvent should not have a negative influence on the reaction but is not otherwise particularly limited and can be exemplified by hydrocarbons such as hexane, octane, decane, cyclohexane, benzene, and toluene; ethers such as diethyl ether, tetrahydrofuran, and dioxane; ketones such as acetone and methyl ethyl ketone; chlorinated hydrocarbons such as dichloromethane and dichloroethane; water; and alcohols such as methanol, ethanol, and isopropanol. A single one of these solvents may be used by itself or two or more may be used in combination.

There are no particular limitations on the amount of solvent use when a solvent is used, but the solvent is preferably used at from 0.005- to 5-times on a mass basis with reference to compound (I) and more preferably is used at from 0.01- to 3-times on a mass basis with reference to compound (I).

Reaction steps (i-a) and (i-b) may be run in an air atmosphere or may be run under an inert gas atmosphere. In addition, they may be run under reduced pressure, under atmospheric pressure, or under an overpressure. The reaction temperature is preferably 0 to 200° C., more preferably 15 to 150° C., and even more preferably 30 to 100° C. Viewed from the perspective of the fluidity of the compound (I) reactant, the reaction is preferably run at a temperature at which no problems with stirring are produced. The reaction time is preferably 0.1 to 50 hours, more preferably 0.5 to 30 hours, and even more preferably 1 to 15 hours.

The aforementioned reaction steps include a so-called slurry reaction, and the reactions can be run using a reaction apparatus that has a stirred apparatus as is normally used. For example, a stirred tank reaction apparatus can be used, and a batch, semi-batch, or continuous tank-type reaction apparatus can be used.

After the aforementioned reaction step has been carried out and, for example, desalting and removal of the excess epihalohydrin have been performed, a derivatization reaction step is preferably carried out to obtain any of various monomers from compound (A). The desalting step can be carried out using a process as normally used for desalting, e.g., separation by sedimentation, centrifugal separation, filtration, and so forth, and can be carried out using a suitable configuration that brings about a thorough elimination of the salt. The desalting step is preferably carried out at a temperature of 15 to 100° C. in order to obtain a satisfactory separation rate. There are no particular limitations on the procedure for removing the excess epihalohydrin as long as removal is obtained; for example, removal can be easily performed by distillation or evaporation.

A detailed description follows for the water-soluble monomer-containing composition derived using the composition of the present invention containing an intermediate for a water-soluble monomer.

The composition of the present invention containing an intermediate for a water-soluble monomer contains compound (A), and a suitable modification of the terminal glycidyl group of this compound (A) yields a composition that contains a compound that can have various functional groups. This compound that can have various functional groups can be polymerized via the polymerizable terminal double bond to yield a polymer that can have various functional groups in terminal position on the side chain and that exhibits water solubility due to the oxyalkylene group in side chain position. This compound is thus useful as a water-soluble monomer.

When the compound that can have various functional groups is obtained by the modification of the terminal glycidyl group in compound (A), its functional group can be suitably selected and used in conformity to the properties that are to be imparted to the water-soluble polymer that is ultimately synthesized. The composition containing such a compound that can have various functional groups can be, for example, a water-soluble monomer-containing composition obtained by reacting a functional group-containing compound with the composition of the present invention containing an intermediate for a water-soluble monomer, wherein the water-soluble monomer is a cationic group-containing monomer obtained using a tertiary amine salt as the functional group-containing compound; a water-soluble monomer-containing composition obtained by reacting a functional group-containing compound with the composition of the present invention containing an intermediate for a water-soluble monomer, wherein the water-soluble monomer is an amino group-containing monomer obtained using a secondary amine as the functional group-containing compound; a water-soluble monomer-containing composition obtained by reacting a functional group-containing compound with the composition of the present invention containing an intermediate for a water-soluble monomer, wherein the water-soluble monomer is a sulfonic acid group-containing monomer obtained using a sulfurous acid compound as the functional group-containing compound; or a water-soluble monomer-containing composition obtained by reacting a functional group-containing compound with the composition of the present invention containing an intermediate for a water-soluble monomer, wherein the water-soluble monomer is an organic ether group-containing monomer obtained using a hydroxyl group-containing compound as the functional group-containing compound. These water-soluble monomer-containing compositions are also one of the inventions disclosed herein and these water-soluble monomers are also one of the inventions disclosed herein.

Thus, a water-soluble monomer-containing composition obtained by reacting a functional group-containing compound and the composition of the present invention containing an intermediate for a water-soluble monomer, wherein this water-soluble monomer is a water-soluble monomer represented by the following general formula (6) obtained using a tertiary amine salt, a secondary amine, a sulfurous acid compound, or a hydroxyl group-containing compound as the aforementioned functional group-containing compound

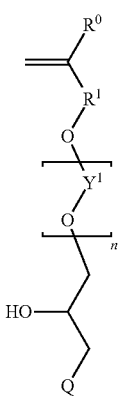

(6)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group ($-Y^1-O-$) and represents a number from 1 to 300; and Q represents any of the following structures with general formulas (7) to (10)), is also one of the inventions disclosed herein.

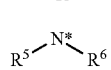

(7)

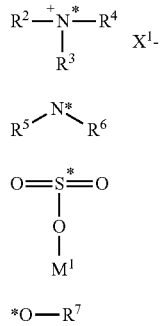

(8)

(9)

(10)

In the formulas, the * indicates that the atom bearing the * is bonded to the carbon atom that is bonded to Q in general formula (6); $R^2$, $R^3$, $R^4$, $R^5$, and $R^6$ are the same or different from one another and represent a hydrogen atom or a $C_{1-20}$ organic group; $R^2$ and $R^3$ may be bonded to each other to form a ring structure; $R^5$ and $R^6$ may be bonded to each other to form a ring structure; $X^1-$ represents a counteranion; $M^1$ represents a hydrogen atom or a monovalent cation; and $R^7$ represents a $C_{1-20}$ organic group.

When a tertiary amine salt is used as the aforementioned functional group-containing compound, a cationic group-containing monomer is obtained for the water-soluble monomer-containing composition. This synthesis reaction is a reaction in which a tertiary amine salt is reacted with the glycidyl group in compound (A) and the compound (A) terminal is converted into a quaternary ammonium salt to yield a cationic group-containing monomer, and this synthesis may be carried out making use as appropriate of a reaction procedure as is normally used for such a reaction.

When a secondary amine is used as the aforementioned functional group-containing compound, an amino group-containing monomer is obtained for the water-soluble monomer-containing composition. This synthesis reaction is a reaction in which a secondary amine is reacted with the glycidyl group in compound (A) and the compound (A) terminal is converted into a tertiary amine to yield an amino group-containing monomer, and this synthesis may be carried out making use as appropriate of a reaction procedure as is normally used for such a reaction.

This amino group-containing monomer contains an amino group at a terminal of the amino group-containing monomer, and the substituent bonded to the nitrogen atom in this amino group can be exemplified by an alkyl group and by groups that contain a functional group such as the hydroxyl group, carboxyl group, and so forth.

When a sulfurous acid compound is used as the aforementioned functional group-containing compound, a sulfonic acid group-containing monomer is obtained for the water-soluble monomer-containing composition. This synthesis reaction is a reaction in which a sulfurous acid compound is reacted with the glycidyl group in compound (A) and the compound (A) terminal is sulfonated to yield a sulfonic acid group-containing monomer, and this synthesis may be carried out making use as appropriate of a reaction procedure as is normally used for such a reaction.

When a hydroxyl group-containing compound is used as the aforementioned functional group-containing compound, an organic ether group-containing monomer is obtained for the water-soluble monomer-containing composition. This synthesis reaction is a reaction in which the hydroxyl group in the hydroxyl group-containing compound is reacted with the glycidyl group in compound (A) to synthesize an organic ether group-containing monomer that contains an organic ether group in terminal position, and this synthesis may be carried out making use as appropriate of a reaction procedure as is normally used for such a reaction.

This organic ether group-containing monomer encompasses a configuration that contains an alkyl ether group at the end of the organic ether group-containing monomer as well as a configuration in which a functional group, e.g., the carboxyl group, is bonded to a carbon atom in this alkyl ether group.

The structures of the cationic group-containing monomer, amino group-containing monomer, sulfonic acid group-containing monomer, and organic ether group-containing monomer are described in detail below.

The water-soluble monomer-containing composition may be subjected to purification as necessary after it has been obtained. This purification step may be carried out by an ordinary purification procedure, for example, extraction, washing, and so forth.

A water-soluble monomer-containing composition is derived as described above using the composition according to the present invention containing an intermediate for a water-soluble monomer, and the water-soluble monomer present in this water-soluble monomer-containing composition is also one of the inventions disclosed herein.

Thus, the water-soluble monomer represented by the following general formula (11)

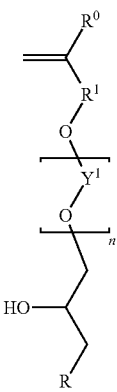

(11)

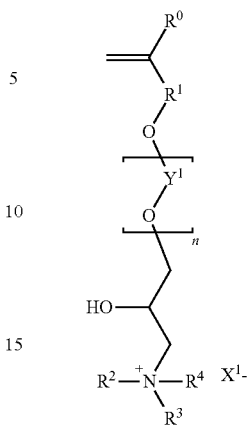

(12)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group ($-Y^1-O-$) and represents a number from 1 to 300; and R represents any of the following structures with general formulas (7) to (9)) is also one of the inventions disclosed herein.

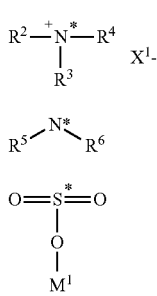

(7)

(8)

(9)

In the formulas, the * indicates that the atom bearing the * is bonded to the carbon atom that is bonded to R in general formula (11); $R^2$, $R^3$, $R^4$, $R^5$, and $R^6$ are the same or different from one another and represent a hydrogen atom or a $C_{1-20}$ organic group; $R^2$ and $R^3$ may be bonded to each other to form a ring structure; $R^5$ and $R^6$ may be bonded to each other to form a ring structure; $X^1-$ represents a counteranion; and $M^1$ represents a hydrogen atom or a monovalent cation.

When R in general formula (11) is represented by general formula (7), the water-soluble monomer is then the cationic group-containing monomer described below; when R in general formula (11) is represented by general formula (8), the water-soluble monomer is then the amino group-containing monomer described below; and when R in general formula (11) is represented by general formula (9), the water-soluble monomer is then the sulfonic acid group-containing monomer described below.

The water-soluble monomer will be described in sequence in the following for each of the functional groups bonded in terminal position.

[The Cationic Group-Containing Monomer of the Present Invention]

As previously indicated, a cationic group-containing monomer is one example of a water-soluble monomer having a particular functional group, and the cationic group-containing monomer having the structure represented by the following general formula (12)

(where, $R^0$ represents a hydrogen atom or a methyl group; $R^1$ represents a methylene group, an ethylene group, or a direct bond; $R^2$, $R^3$, and $R^4$ are the same or different from one another and represent a hydrogen atom or a $C_{1-20}$ organic group; $R^2$ and $R^3$ may be bonded to each other to form a ring structure; each $Y^1$ is the same or different from one another and represents a $C_{2-20}$ alkylene group; n is the average number of moles of addition of the oxyalkylene group ($-Y^1-O-$) and represents a number from 1 to 300; and $X^1-$ represents a counteranion) is one of the inventions disclosed herein.

When $R^1$ in general formula (12) is a direct bond, the $H_2C=C(R^0)-R^1-O-$ in general formula (12) is then represented by $H_2C=C(R^0)-O-$. Thus, $H_2C=C(R^0)-R^1-$ denotes the methallyl group when $R^0$ is a methyl group and $R^1$ is a methylene group; the isoprenyl group when $R^0$ is a methyl group and $R^1$ is an ethylene group; the isopropenyl group when $R^0$ is a methyl group and $R^1$ is a direct bond; the allyl group when $R^0$ is a hydrogen atom and $R^1$ is methylene; the butenyl group when $R^0$ is a hydrogen atom and $R^1$ is an ethylene group; and the vinyl group when $R^0$ is a hydrogen atom and $R^1$ is a direct bond.

Viewed in terms of polymerizability, isoprenyl, methallyl, allyl, and vinyl groups are preferred for) $H_2C=C(R^0)-R^1-O-$ in general formula (12), wherein isoprenyl, methallyl, and allyl groups are more preferred and isoprenyl and methallyl groups are even more preferred.

$R^2$, $R^3$, and $R^4$ in general formula (12) are the same or different from one another and represent a hydrogen atom or a $C_{1-20}$ organic group. There are no limitations on the $C_{1-20}$ organic group other than that the number of carbons is 1 to 20 for the group as a whole, but alkyl, aryl, and alkenyl groups are preferred. The alkyl, aryl, and alkenyl groups may be unsubstituted groups or 1 or 2 or more of the hydrogen atoms may be substituted by another organic group. This other organic group that is a substituent in such a case can be exemplified by alkyl groups (when the $C_{1-20}$ organic group is an alkyl group, this becomes an alkyl group on the whole and the organic group then corresponds to an unsubstituted alkyl group), aryl groups, alkenyl groups, alkoxy groups, hydroxyl group, acyl groups, ether groups, amide groups, ester groups, and ketone groups.

$R^2$, $R^3$, and $R^4$ more preferably have from 1 to 8 carbons, even more preferably from 1 to 5 carbons, and particularly preferably 1 or 2 carbons. The cationic group-containing monomer of the present invention can be produced in high yields within these ranges.

$R^2$, $R^3$, and $R^4$ can be specifically exemplified by alkyl groups such as methyl, ethyl, isopropyl, n-propyl, n-butyl, isobutyl, octyl, lauryl, stearyl, cyclohexyl, and 2-ethylhexyl; alkenyl groups such as butylene, octylene, and nonylene; aryl groups such as phenyl, benzyl, phenethyl, 2,3-xylyl, 2,4-xylyl, mesityl, and naphthyl; and groups provided by substituting a portion of the hydrogen on the aforementioned alkyl, alkenyl, and aryl by an alkoxy group, carboxy ester group, amino group, amide group, hydroxyl group, and so forth, e.g., hydroxyethyl and hydroxypropyl. Methyl and ethyl are preferred among the preceding because they make possible the high-yield production of the cationic group-containing monomer of the present invention.

$R^2$ and $R^3$ in general formula (12) may be bonded to each other to form a ring structure, in which case the ring structure formed by the nitrogen atom and $R^2$ and $R^3$ is preferably a 3- to 7-membered ring from the standpoint of the stability of the ring structure, i.e., the total number of carbons in $R^2$ and $R^3$ is preferably 2 to 6.

Each $Y^1$ in general formula (12) is independently a $C_{2-20}$ alkylene group, but $Y^1$ is preferably a $C_{2-4}$ alkylene group and particularly preferably is a $C_{2-3}$ alkylene group, because these provide a good polymerizability for the cationic group-containing monomer of the present invention. Specifically, $C_{2-4}$ alkylene groups such as ethylene, propylene, and butylene are preferred and $C_{2-3}$ alkylene groups such as ethylene and propylene are particularly preferred. The alkylene group may be a single species or may be two or more species, and when two or more species are present the —$Y^1$—O— structures may have a random sequence, an alternating sequence, or a block sequence.

The n in general formula (12) is the average number of moles of addition of the oxyalkylene group (—$Y^1$—O—) and represents a number from 1 to 300. Viewed from the perspective of making possible the introduction of a large amount of polyalkylene glycol chain into the polymer, n is preferably at least 2, more preferably at least 5, and even more preferably at least 10. At least 20 is particularly preferred. Viewed from the perspective of providing a good polymerizability for the cationic group-containing monomer of the present invention, n is preferably no greater than 200, more preferably no greater than 150, and even more preferably no greater than 120. No greater than 100 is particularly preferred and no greater than 50 is most preferred.

A counteranion $X^1$— is present in cationic group-containing monomer of the present invention in the neighborhood of the quaternized nitrogen atom. While there are no particular limitations on the type of counteranion $X^1$—, halide ions and alkyl sulfate ions are preferred. The halide ion can be specifically exemplified by the ions of the chlorine atom, bromide atom, iodine atom, and fluorine atom, among which the ions of the chlorine atom, bromine atom, and iodine atom are preferred and the ion of the chlorine atom is particularly preferred. The alkyl sulfate ion can be specifically exemplified by the methyl sulfate ion and the ethyl sulfate ion, wherebetween the methyl sulfate ion is preferred.

A polymer obtained by the polymerization of the cationic group-containing monomer of the present invention has a structure that derives from the cationic group-containing monomer of the present invention. This structure derived from the cationic group-containing monomer is a structure in which the carbon-carbon double bond in the cationic group-containing monomer of the present invention has been converted into a single bond, and can be represented by the following general formula (13)

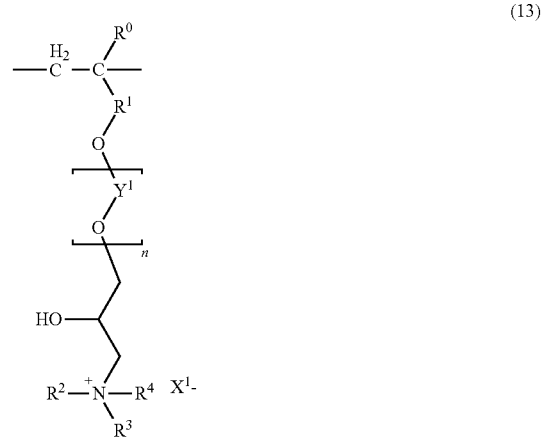

(13)

(where, $R^0$ represents a hydrogen atom or a methyl group; $R^1$ represents a methylene group, an ethylene group, or a direct bond; $R^2$, $R^3$, and $R^4$ are the same or different from one another and represent a hydrogen atom or a $C_{1-20}$ organic group; $R^2$ and $R^3$ may be bonded to each other to form a ring structure; each $Y^1$ is the same or different from one another and represents a $C_{2-20}$ alkylene group; n is the average number of moles of addition of the oxyalkylene group (—$Y^1$—O—) and represents a number from 1 to 300; and $X^1$— represents a counteranion).

[The Amino Group-Containing Monomer of the Present Invention]

As previously indicated, an amino group-containing monomer is one example of a water-soluble monomer having a particular functional group, and the amino group-containing monomer having the structure represented by the following general formula (14)

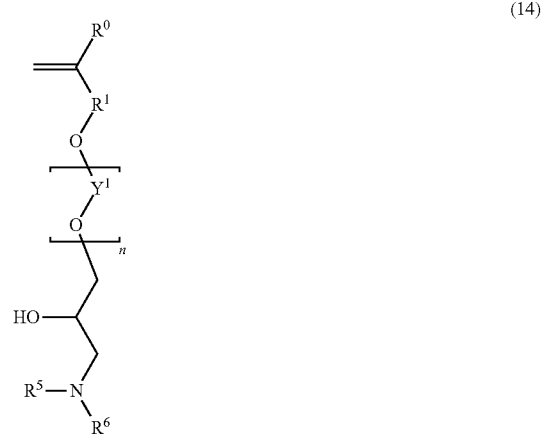

(14)

(where, $R^0$ represents a hydrogen atom or a methyl group; $R^1$ represents a methylene group, an ethylene group, or a direct bond; $R^5$ and $R^6$ are the same or different from one another and represent a hydrogen atom or a $C_{1-20}$ organic group; $R^5$ and $R^6$ may be bonded to each other to form a ring structure; each $Y^1$ is the same or different from one another and represents a $C_{2-20}$ alkylene group; and n is the average number of moles of addition of the oxyalkylene group (—$Y^1$—O—) and represents a number from 1 to 300) is also one of the inventions disclosed herein.

$R^5$ and $R^6$ in general formula (14) are the same or different from one another and represent a hydrogen atom or a $C_{1-20}$ organic group. This $C_{1-20}$ organic group can be exemplified by the same $C_{1-20}$ organic groups as provided above for $R^2$, $R^3$, and $R^4$ in general formula (12), among which $C_{1-8}$ is more preferred and $C_{1-5}$ is even more preferred. The amino group-containing monomer of the present invention can be produced in high yields in these ranges. Methyl, ethyl, n-butyl, and hydroxyethyl groups are specifically preferred.

$R^5$ and $R^6$ in general formula (14) may be bonded to each other to form a ring structure, in which case the ring structure formed by the nitrogen atom and $R^5$ and $R^6$ is preferably a 3- to 7-membered ring from the standpoint of the stability of the ring structure, i.e., the total number of carbons in $R^5$ and $R^6$ is preferably 2 to 6.

$R^0, R^1, Y^1$, and n in general formula (14) are the same as for general formula (12).

Preferred embodiments of the amino group-containing monomer of the present invention are as described above, but in the particular case in which $R^0$ in general formula (14) represents a hydrogen atom and $R^1$ represents a methylene group, i.e., when this monomer is an allyl-type amino group-containing monomer, then preferably each $Y^1$ is the same or different from one another and represents a $C_{2-20}$ alkylene group, n is a number from 20 to 300, and $R^5$ and $R^6$ are the same or different from one another and represent the hydrogen atom or a possibly substituted $C_{1-20}$ alkyl group, aryl group, or alkenyl group. On the other hand, when the combination of $R^0$ and $R^1$ in general formula (14) is a combination other than $R^0$=hydrogen atom and $R^1$=a methylene group, i.e., in the case of an amino group-containing monomer of the present invention other than an allyl-type amino group-containing monomer, then preferably each $Y^1$ is the same or different from one another and represents a $C_{2-20}$ alkylene group, n is a number from 1 to 300, and $R^5$ and $R^6$ are the same or different from one another and represent the hydrogen atom or a possibly substituted $C_{1-20}$ alkyl group, aryl group, or alkenyl group.

The amino group-containing polymer obtained by the polymerization of the amino group-containing monomer of the present invention has a structure that derives from the amino group-containing monomer of the present invention. This structure derived from the amino group-containing monomer is a structure in which the carbon-carbon double bond in the amino group-containing monomer of the present invention has been converted into a single bond, and can be represented by the following general formula (15)

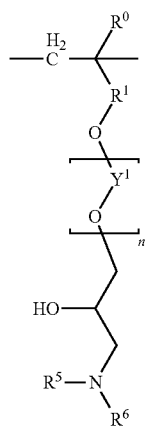

(15)

(where, $R^0$ represents a hydrogen atom or a methyl group; $R^1$ represents a methylene group, an ethylene group, or a direct bond; $R^5$ and $R^6$ are the same or different from one another and represent a hydrogen atom or a $C_{1-20}$ organic group; $R^5$ and $R^6$ may be bonded to each other to form a ring structure; each $Y^1$ is the same or different from one another and represents a $C_{2-20}$ alkylene group; and n is the average number of moles of addition of the oxyalkylene group ($-Y^1-O-$) and represents a number from 1 to 300).

The group bearing the carbon-carbon double bond that undergoes polymerization in the amino group-containing monomer of the present invention, i.e., $H_2C=C(R^0)-R^1-$, is preferably the isoprenyl group, methallyl group, allyl group, or vinyl group. The isoprenyl group and methallyl group are particularly preferred from the standpoint of polymerizability.

[The Sulfonic Acid Group-Containing Monomer of the Present Invention]

As previously indicated, a sulfonic acid group-containing monomer is one example of a water-soluble monomer having a particular functional group, and the sulfonic acid group-containing monomer having the structure represented by the following general formula (16)

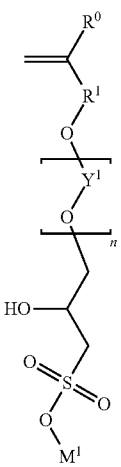

(16)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group ($-Y^1-O-$) and represents a number from 1 to 300; and $M^1$ represents a hydrogen atom or a monovalent cation) is also one of the inventions disclosed herein.

$M^1$ general formula (16) represents a hydrogen atom or a monovalent cation. This monovalent cation can be exemplified by alkali metal ions such as sodium, potassium, and lithium; an ammonium ion; and quaternary ammonium salts such as the tetramethylammonium salt, tetraethylammonium salt, and tetrabutylammonium salt, wherein an alkali metal ion such as sodium, potassium, and lithium is preferred and the sodium ion is particularly preferred.

$R^0, R^1, Y^1$, and n in general formula (16) are the same as for general formula (12).

The sulfonic acid group-containing polymer obtained by the polymerization of the sulfonic acid group-containing monomer of the present invention has a structure that derives from the sulfonic acid group-containing monomer of the present invention. This structure derived from the sulfonic acid group-containing monomer is a structure in which the carbon-carbon double bond in the sulfonic acid group-containing monomer of the present invention has been converted into a single bond, and can be represented by the following general formula (17)

(17)

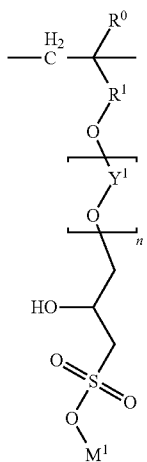

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group ($-Y^1-O-$) and represents a number from 1 to 300; and $M^1$ represents a hydrogen atom or a monovalent cation).

The group bearing the carbon-carbon double bond that undergoes polymerization in the sulfonic acid group-containing monomer of the present invention, i.e., $H_2C=C(R^0)-R^1-$, is preferably the isoprenyl group, methallyl group, allyl group, or vinyl group. The isoprenyl group and methallyl group are particularly preferred from the standpoint of polymerizability.

[The Organic Ether Group-Containing Monomer of the Present Invention]

An organic ether group-containing monomer is one example of a water-soluble monomer having a particular functional group as indicated above and can be, for example, the organic ether group-containing monomer having the structure represented by the following general formula (18)

(18)

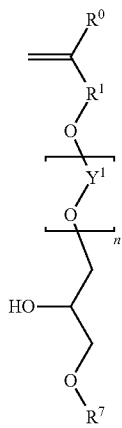

(where, $R^0$ represents a hydrogen atom or a methyl group; $R^1$ represents a methylene group, an ethylene group, or a direct bond; $R^7$ represents a $C_{1-20}$ organic group; each $Y^1$ is the same or different from one another and represents a $C_{2-20}$ alkylene group; and n is the average number of moles of addition of the oxyalkylene group ($-Y^1-O-$) and represents a number from 1 to 300).

$R^7$ in general formula (18) represents a $C_{1-20}$ organic group. This organic group may have a substituent, and there are no particular limitations on this organic group other than that it has from 1 to 20 carbons as a whole. This organic group can be exemplified by alkyl, cycloalkyl, alkenyl, alkynyl, aryl, amino, alkoxyl, and groups provided by combining these groups. Preferred among the preceding are alkyl, cycloalkyl, alkenyl, alkynyl, aryl, alkoxyl, and groups provided by combining these groups, while alkyl, aryl, alkoxyl, and groups provided by combining these groups are more preferred. The substituent on this $C_{1-20}$ organic group can be exemplified by halogen atoms, dialkyl groups, the amino group, the nitro group, the carbonyl group, the carboxyl group, the alkoxy groups, the acetoxy group, the hydroxyl group, the mercapto group, the sulfonic group, and the methylenebiscarbonyl group. The organic group preferably has from 1 to 18 carbons, more preferably from 1 to 16 carbons, and even more preferably from 1 to 14 carbons.

The organic group can be specifically exemplified by alkyl groups such as methyl, ethyl, isopropyl, n-propyl, n-butyl, isobutyl, t-butyl, octyl, lauryl, stearyl, cyclopentyl, cyclohexyl, and 2-ethylhexyl; alkenyl groups such as allyl and isoprenyl; aryl groups such as phenyl, benzyl, and naphthyl; and groups provided by replacing a portion of the hydrogen atoms in the preceding with, e.g., an alkoxy group, carboxy ester group, amino group, amide group, hydroxyl group, and so forth, for example, the 2-methoxyethyl group, 2-ethoxyethyl group, and p-methoxyphenyl group. Preferred among the preceding are methyl, ethyl, n-butyl, octyl, lauryl, and 2-ethylhexyl because these make possible the high-yield production of the organic ether group-containing monomer (also referred to below as an organic ether group-containing polyalkylene glycol-type monomer).

$R^0$, $R^1$, $Y^1$, and n in general formula (18) are the same as for general formula (12).

The polymer obtained by the polymerization of the organic ether group-containing monomer has a structure that derives from the aforementioned organic ether group-containing monomer. This structure derived from the organic ether group-containing monomer is a structure in which the carbon-carbon double bond in the organic ether group-containing monomer has been converted into a single bond, and can be represented by the following general formula (19)

(19)

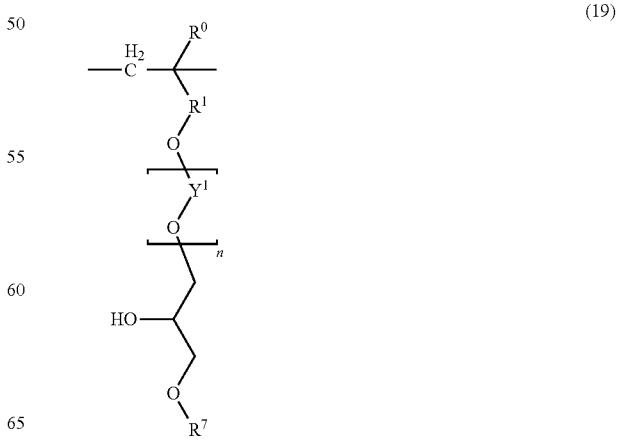

(where, $R^0$ represents a hydrogen atom or a methyl group; $R^1$ represents a methylene group, an ethylene group, or a direct bond; $R^7$ represents a $C_{1-20}$ organic group; each $Y^1$ is the same or different from one another and represents a $C_{2-20}$ alkylene group; and n is the average number of moles of addition of the oxyalkylene group (—$Y^1$—O—) and represents a number from 1 to 300).

A suitable process for producing the water-soluble monomer of the present invention will now be described.

An applicable production process as normally used can be used for the water-soluble monomer of the present invention and there are no particular limitations thereon; however, the water-soluble monomer of the present invention is preferably produced by the following production process. This process can produce the water-soluble monomer of the present invention in high yields.

Thus, a process of producing a water-soluble monomer represented by the following general formula (6)

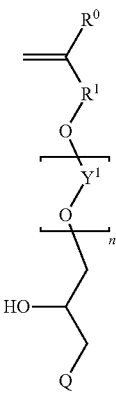

(6)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; n is the average number of moles of addition of the oxyalkylene group (—$Y^1$—O—) and represents a number from 1 to 300; and Q represents any of the structures with the general formulas (7) to (10) given below), wherein the production process comprises:

a step (i) of reacting a compound (I) represented by the following general formula (I) and an epihalohydrin and an alkali compound

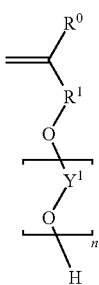

(I)

(where, $R^0$ represents a hydrogen atom or a methyl group; $R^1$ represents a methylene group, an ethylene group, or a direct bond; each $Y^1$ is the same or different from one another and represents a $C_{2-20}$ alkylene group; and n is the average number of moles of addition of the oxyalkylene group (—$Y^1$—O—) and represents a number from 1 to 300) or reacting a compound (I) with the preceding general formula (I) and an epihalohydrin in the presence of a catalyst; and a step (ii) of reacting the reaction product obtained in step (i) with a tertiary amine salt, secondary amine, sulfurous acid compound, or hydroxyl group-containing compound or a step of reacting the reaction product obtained in step (i) with a secondary amine and reacting the reaction product obtained by this reaction with a quaternizing agent, is also one of the inventions disclosed herein.

The water-soluble monomer production process of the present invention must contain this step (i) and step (ii), but may contain other steps.

(7)

(8)

(9)

(10)

In the formulas, the * indicates that the atom bearing the * is bonded to the carbon atom that is bonded to Q in general formula (6); $R^2$, $R^3$, $R^4$, $R^5$, and $R^6$ are the same or different from one another and represent a hydrogen atom or a $C_{1-20}$ organic group; $R^2$ and $R^3$ may be bonded to each other to form a ring structure; $R^5$ and $R^6$ may be bonded to each other to form a ring structure; $X^1$— represents a counteranion; $M^1$ represents a hydrogen atom or a monovalent cation; and $R^7$ represents a $C_{1-20}$ organic group.

The water-soluble monomer represented by general formula (6) and produced by the aforementioned production process is the previously described cationic group-containing monomer when Q in general formula (6) is represented by general formula (7); is the previously described amino group-containing monomer when Q in general formula (6) is represented by general formula (8); is the previously described sulfonic acid group-containing monomer when Q in general formula (6) is represented by general formula (9); and is the previously described organic ether group-containing monomer when Q in general formula (6) is represented by general formula (10). The water-soluble monomer produced by the aforementioned production process is preferably the preferred form of each of the water-soluble monomers described above.

The aforementioned water-soluble monomer production process is described below in sequence for each individual water-soluble monomer.

[Processes for Producing the Cationic Group-Containing Monomer of the Present Invention]

The cationic group-containing monomer of the present invention can be produced by the process described above or by a generally known production process, but is preferably produced by a process according to the following production processes (1-1) to (1-6). These processes can produce the cationic group-containing monomer of the present invention in high yields.

Thus, a preferred process (1-1) for producing the cationic group-containing monomer of the present invention is a process for producing the cationic group-containing monomer comprising (i) a step of reacting a compound (I) given by general formula (I) (also referred to below as the polyalkylene glycol chain-containing monomer) and an epihalohydrin and an alkali compound (step A) and (ii) a step of reacting the reaction product obtained in step A with a tertiary amine salt (step B).

A preferred process (1-2) for producing the cationic group-containing monomer of the present invention is a process for producing the cationic group-containing monomer comprising (i) a step of reacting a polyalkylene glycol chain-containing monomer given by general formula (I) and an epihalohydrin and an alkali compound (step A), (ii) a step of reacting the reaction product obtained in step A with a secondary amine (step C), and (iii) a step of reacting the reaction product obtained in step C with a quaternizing agent (step D).

A preferred process (1-3) for producing the cationic group-containing monomer of the present invention is a process for producing the cationic group-containing monomer comprising (i) a step of reacting a polyalkylene glycol chain-containing monomer given by general formula (I) and an epihalohydrin in the presence of a catalyst (step E) and (ii) a step of reacting the reaction product obtained in step E with a tertiary amine (step F).

A preferred process (1-4) for producing the cationic group-containing monomer of the present invention is a process for producing the cationic group-containing monomer comprising (i) a step of reacting a polyalkylene glycol chain-containing monomer given by general formula (I) and a glycidyltrialkylammonium salt (step G).

A preferred process (1-5) for producing the cationic group-containing monomer of the present invention is a process for producing the cationic group-containing monomer comprising (i) a step of reacting a polyalkylene glycol chain-containing monomer given by general formula (I) and an epihalohydrin in the presence of a catalyst (step E), (ii) a step of reacting the reaction product obtained in step E with an alkali compound (step H), and (iii) a step of reacting the reaction product obtained in step H with a tertiary amine salt (step B).

A preferred process (1-6) for producing the cationic group-containing monomer of the present invention is a process for producing the cationic group-containing monomer comprising (i) a step of reacting a polyalkylene glycol chain-containing monomer given by general formula (I) and an epihalohydrin in the presence of a catalyst (step E), (ii) a step of reacting the reaction product obtained in step E with an alkali compound (step H), (iii) a step of reacting the reaction product obtained in step H with a secondary amine (step C), and (iv) a step of reacting the reaction product obtained in step C with a quaternizing agent (step D).

Preferred embodiments of $R^0$, $R^1$, $Y^1$ and n in the polyalkylene glycol chain-containing monomer represented by general formula (I) in production processes (1-1) to (1-6) are the same as the preferred embodiments of $R^0$, $R^1$, $Y^1$, and n for general formula (12).

A monomer prepared by adding, by a normally used procedure, an alkylene oxide to an alkylene glycol monovinyl ether, (meth)allyl alcohol, isoprenol, or an alcohol having a structure provided by the addition of an alkylene oxide to the preceding, can be used as the polyalkylene glycol chain-containing monomer represented by general formula (I). This is preferred because it enables a high purity for the monomer.

The epihalohydrin in production processes (1-1), (1-2), (1-3), (1-5), and (1-6) is preferably an epihalohydrin having general formula (II).

This epihalohydrin can be specifically exemplified by epichlorohydrin, epibromohydrin, and epiiodohydrin. Among these, epichlorohydrin is preferred because it is inexpensive at an industrial level.

The tertiary amine salt in production processes (1-1) and (1-5) is preferably a tertiary amine salt as represented by the following general formula (20)

(where, $R^2$, $R^3$, and $R^4$ are the same or different from one another and represent a hydrogen atom or a $C_{1-20}$ organic group; $R^2$ and $R^3$ may be bonded to each other to form a ring structure; and $X^1-$ represents a counteranion).

The preferred embodiments of $R^2$, $R^3$, $R^4$, and $X^1-$ in general formula (20) are the same as the preferred embodiments of $R^2$, $R^3$, $R^4$, and $X^1-$ for general formula (12).

The tertiary amine salt under consideration can be specifically exemplified by the hydrochlorides, hydrobromides, hydroiodides, nitrates, acetates, perchlorates, para-toluenesulfonates, and so forth, of tertiary amines such as trimethylamine, dimethylethylamine, dimethylisopropylamine, dimethyl-n-propylamine, dimethylcyclohexylamine, triethylamine, triisopropylamine, tri-n-propylamine, tributylamine, trilaurylamine, tristearylamine, tricyclohexylamine, tri-2-ethylhexylamine, triethanolamine, tris(2-hydroxypropyl)amine, and so forth. Preferred among the preceding are trimethylamine hydrochloride, triethylamine hydrochloride, and dimethylethylamine hydrochloride because these make possible the high-yield production of the cationic group-containing monomer of the present invention.

The secondary amine in production processes (1-2) and (1-6) is preferably a secondary amine as represented by the following general formula (21)

(where, $R^2$ and $R^3$ each is the same or different from one another and represents a hydrogen atom or a $C_{1-20}$ organic group and $R^2$ and $R^3$ may be bonded to each other to form a ring structure).

The preferred embodiments of $R^2$ and $R^3$ in general formula (21) are the same as the preferred embodiments of $R^2$ and $R^3$ for general formula (12).

The secondary amine under consideration can be exemplified by dialkylamines such as dimethylamine, methylethylamine, diethylamine, diisopropylamine, di-n-propylamine, di-n-butylamine, dioctylamine, dilaurylamine, distearylamine, dicyclohexylamine, di-2-ethylhexylamine, and so forth; dialkanolamines such as diethanolamine, bis(2-hydroxypropyl)amine, and so forth; and cyclic amines such as morpholine, pyrrole, and so forth. Dimethylamine, methylethylamine, diethylamine, and diethanolamine are preferred among the preceding because they make possible the high-yield production of the cationic group-containing monomer of the present invention and because they are also inexpensive at an industrial level.

The quaternizing agent in production processes (1-2) and (1-6) can be exemplified by alkyl halides such as methyl chloride, ethyl chloride, methyl bromide, ethyl bromide, methyl iodide, and ethyl iodide; benzyl halides such as benzyl chloride, benzyl bromide, and benzyl iodide; dialkyl sulfates such as dimethyl sulfate and diethyl sulfate; and alkyl sulfonates such as methyl para-toluenesulfonate and ethyl para-toluenesulfonate. Methyl chloride, benzyl chloride, and dimethyl sulfate are preferred among the preceding for their ease of acquisition at an industrial level.

The tertiary amine in production process (1-3) is preferably a tertiary amine as represented by general formula (22)

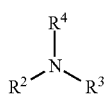

(22)

(where, $R^2$, $R^3$, and $R^4$ are the same or different from one another and represent a hydrogen atom or a $C_{1-20}$ organic group and $R^2$ and $R^3$ may be bonded to each other to form a ring structure).

The preferred embodiments of $R^2$, $R^3$, and $R^4$ in general formula (22) are the same as the preferred embodiments of $R^2$, $R^3$, and $R^4$ for general formula (12).

The tertiary amine under consideration can be specifically exemplified by trialkylamines such as trimethylamine, dimethylethylamine, dimethylisopropylamine, dimethyl-n-propylamine, dimethylcyclohexylamine, triethylamine, triisopropylamine, tri-n-propylamine, tributylamine, trilaurylamine, tristearylamine, tricyclohexylamine, tri-2-ethylhexylamine, and so forth, and by trialkanolamines such as triethanolamine, tris(2-hydroxypropyl)amine, and so forth. Trimethylamine, dimethylethylamine, triethylamine, and triethanolamine are preferred among the preceding because they make possible the high-yield production of the cationic group-containing monomer of the present invention.

The glycidyltrialkylammonium salt in production process (1-4) is preferably represented by general formula (23)

(23)

(where, $R^2$, $R^3$, and $R^4$ are the same or different from one another and represent a hydrogen atom or a $C_{1-20}$ organic group, $R^2$ and $R^3$ may be bonded to each other to form a ring structure, and $X^1-$ is a counteranion).

The preferred embodiments of $R^2$, $R^3$, $R^4$, and $X^1-$ in general formula (23) are the same as the preferred embodiments of $R^2$, $R^3$, $R^4$, and $X^1-$ for general formula (12).

This glycidyltrialkylammonium salt can be specifically exemplified by glycidyltrimethylammonium chloride, glycidyltriethylammonium chloride, glycidyltrimethylammonium bromide, and glycidyltriethylammonium bromide. Glycidyltrimethylammonium chloride is preferred among the preceding for its ease of acquisition industrially.

Production processes (1-1) to (1-6) are thus represented by the following reaction formulas.

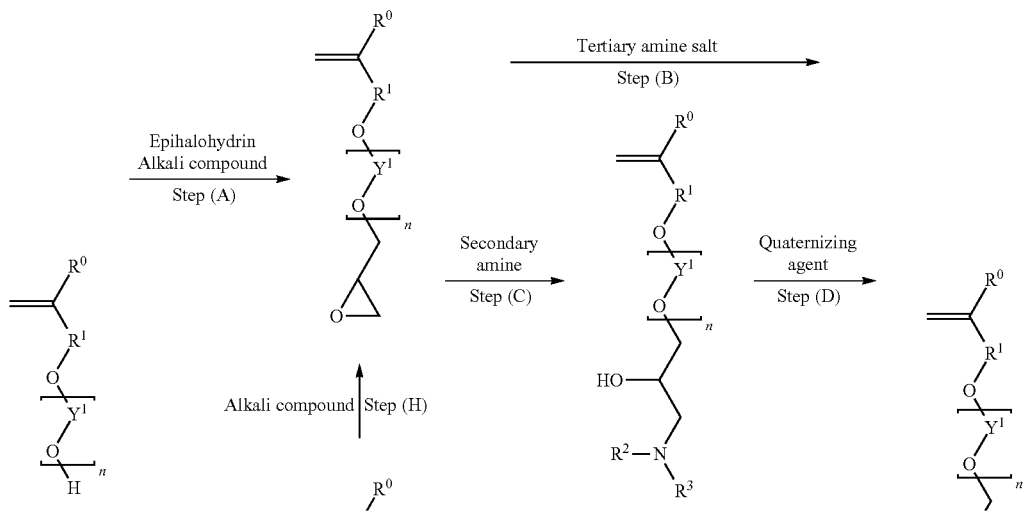

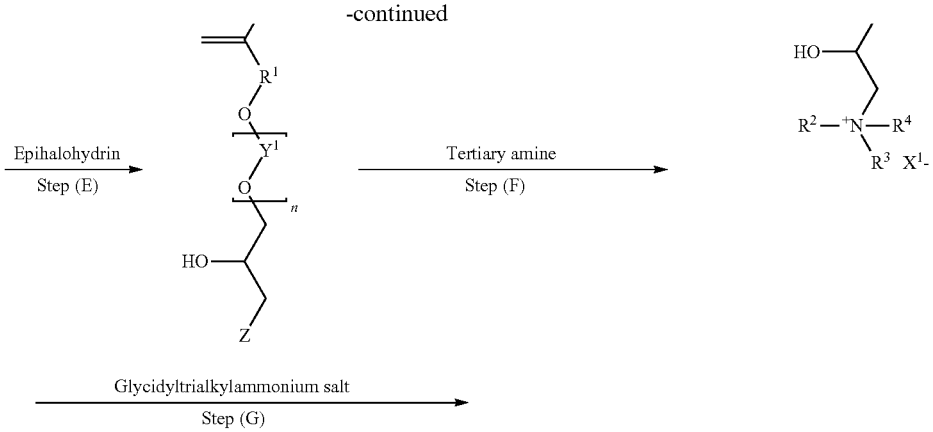

The reaction conditions and embodiments of each of the essential steps A to H in production processes (1-1) to (1-6) are described in detail in the following.

The reactions in steps A, B, C, D, E, F, G, and H proceed in good yields when run in the absence of solvent and this is more preferred from the standpoint of the volumetric efficiency; however, they can also be run in the presence of a solvent. A single solvent may be used by itself or two or more solvents may be used in combination. The amount of solvent used is not particularly limited, but is generally in the range from 0.005- to 5-fold on a mass basis and preferably 0.01- to 3-fold on a mass basis, with reference to the polyalkylene glycol chain-containing monomer with general formula (I) in the case of steps A, E, and G and with reference to the reaction product obtained in the preceding step in the case of steps B, C, D, F, and H.

Except for the requirement that the solvent should not have a negative effect on the reaction, there are no particular limitations on the solvent usable in the reactions in steps A, E, and G, and this solvent can be exemplified by hydrocarbons such as hexane, octane, decane, cyclohexane, benzene, and toluene; ethers such as diethyl ether, tetrahydrofuran, and dioxane; ketones such as acetone and methyl ethyl ketone; and chlorinated hydrocarbons such as dichloromethane and dichloroethane.

Except for the requirement that the solvent should not have a negative effect on the reaction, there are no particular limitations on the solvent usable in the reactions in steps B, C, D, F, and H, and this solvent can be exemplified by water; alcohols such as methanol, ethanol, and isopropanol; ethers such as diethyl ether, tetrahydrofuran, and dioxane; and ketones such as acetone and methyl ethyl ketone.

The reactions in steps A, B, C, D, E, F, G, and H may be run under an air atmosphere or may be run under an inert gas atmosphere. These reactions may be run under reduced pressure, at atmospheric pressure, or under an overpressure. The reaction temperature is generally 0 to 200° C., preferably 15 to 150° C., and more preferably 30 to 100° C. Viewed from the perspective of the fluidity of the reactants, i.e., the polyalkylene glycol chain-containing monomer reactant with general formula (I) and the compound obtained in the preceding step, the reactions are preferably run at a temperature that does not produce problems with stirring. The reaction time is generally from 0.1 to 50 hours, preferably from 0.5 to 30 hours, and more preferably from 1 to 15 hours.

When a catalyst is used in the preceding step, the reactions in steps B, C, D, F, and H may be directly run in the presence of the residual catalyst.

Step A is a so-called slurry reaction and can be run in a reaction apparatus that has a general stirring device. For example, step A may be run using a stirred-tank reaction apparatus in a batch, semi-batch, or continuous tank-type reactor. The reaction in step A is preferably followed by a step of, for example, desalting and removal of the excess epihalohydrin, and then by the ensuing step. The desalting step can be carried out by, e.g., separation by sedimentation, centrifugal separation, filtration, and so forth, and is not particularly limited. The conditions for running the desalting step should result in a suitable execution that thoroughly removes the salt, and execution at a temperature of 15° C. to 100° C. is preferred from the standpoint of obtaining a satisfactory separation rate. The excess epihalohydrin can be easily removed by, for example, distillation or evaporation.

The reactions in steps B, C, D, E, F, G, and H may be run using a batch or continuous regime; for example, these reactions may be run in a tank-type or pipe-type reactor apparatus.

In addition, step F or H may be run after the reaction of step E after a step such as a wash has been performed.

The reaction of step A is run in the presence of an alkali compound and optionally in the presence of a catalyst and/or a solvent. There are no particular limitations on this alkali compound, but an alkali metal hydroxide such as sodium hydroxide or potassium hydroxide is preferred. The amount of alkali compound used is generally (hydroxyl group)/(alkali compound)=15/1 to 1/15, preferably 5/1 to 1/5, and more preferably 3/1 to 1/3, as the molar ratio with the hydroxyl group (as the hydroxyl value) in the polyalkylene glycol chain-containing monomer with general formula (I). The alkali compound may be used in the form of the aqueous solution. In this case, the reaction may be run while removing water (including also the water secondarily produced accompanying the progress of the reaction).

There are no particular limitations on the type of this catalyst, and it can be exemplified by quaternary ammonium salts such as tetramethylammonium chloride, tetraethylammonium chloride, tetrapropylammonium chloride, tetrabutylammonium chloride, tetraoctylammonium chloride, benzyltrimethylammonium chloride, benzyltriethylammonium chloride, octyltrimethylammonium chloride, cetyltrimethylammonium chloride, tetramethylammonium bromide, tetraethylammonium bromide, tetrapropylammonium bromide, tetrabutylammonium bromide, tetraoctylammonium bromide, benzyltrimethylammonium bromide, benzyltriethylammonium bromide, octyltrimethylammonium bromide, cetyltrimethylammonium bromide; phosphonium salts such as tetrabutylphosphonium chloride and tetrabutylphosphonium bromide; and crown ethers such as 15-crown-5 and 18-crown-6.

When such a catalyst is used, its amount of use is generally (hydroxyl group)/(catalyst)=1/0.0001 to 1/0.3, preferably 1/0.001 to 1/0.2, and more preferably 1/0.005 to 1/0.1, as the molar ratio with the hydroxyl group (as the hydroxyl value) in the polyalkylene glycol chain-containing monomer with general formula (I). A satisfactory catalytic effect is not obtained when too little catalyst is present, while a greater effect is not obtained when the amount of catalyst is overly large, which is thus uneconomical.

The amount of use for the epihalohydrin used in the reactions in steps A and E is generally (hydroxyl group)/(epihalohydrin)=1/1 to 1/15, preferably 1/1 to 1/10, and more preferably 1/1 to 1/5, as the molar ratio with the hydroxyl group (as the hydroxyl value) in the polyalkylene glycol chain-containing monomer with general formula (I). Outside this range, a crosslinking component may be produced and gelation may occur during polymerization.

The amount of use for the tertiary amine salt used in the reaction in step B is generally (glycidyl group)/(tertiary amine salt)=2/1 to 1/2, preferably 1.5/1 to 1/1.5, and more preferably 1.3/1 to 1/1.3, as the molar ratio with the number of moles of the glycidyl group in the reaction product obtained in the preceding step. The tertiary amine salt may be used in the form of its aqueous solution, in which case this is generally an aqueous solution containing at least 30 mass % tertiary amine salt, preferably is an aqueous solution containing at least 40 mass %, and more preferably is an aqueous solution containing at least 50 mass %. The selectivity for the cationic group-containing monomer yielded by the reaction may be reduced at less than 30 mass %.

The amount of use for the secondary amine used in the reaction in step C is generally (glycidyl group)/(secondary amine)=2/1 to 1/2, preferably 1.5/1 to 1/1.5, and more preferably 1.3/1 to 1/1.3, as the molar ratio with the number of moles of the glycidyl group in the reaction product obtained in the preceding step.

The amount of use for the quaternizing agent used in the reaction in step D is generally (amino group)/(quaternizing agent)=2/1 to 1/2, preferably 1.5/1 to 1/1.5, and more preferably 1.3/1 to 1/1.3, as the molar ratio with the number of moles of the amino group in the reaction product obtained in the preceding step.

The catalyst in the reaction in step E may be an acid or a base, wherein an acid is preferred. This acid may be a Lewis acid or a Brønsted acid wherein a Lewis acid is preferred. The species generally known as Lewis acids can be used as this Lewis acid, for example, boron trifluoride, tin tetrachloride, tin dichloride, zinc chloride, ferric chloride, aluminum chloride, titanium tetrachloride, magnesium chloride, and antimony pentachloride. Its use amount is generally (hydroxyl group)/(catalyst)=1/0.0001 to 1/0.1, preferably 1/0.0005 to 1/0.05, and more preferably 1/0.001 to 1/0.03, as the molar ratio with the hydroxyl group (as the hydroxyl value) of the polyalkylene glycol chain-containing monomer with general formula (I). A satisfactory catalytic effect is not obtained when too little catalyst is present, while a greater effect is not obtained when the amount of catalyst is overly large, which is thus uneconomical.

The amount of use for the tertiary amine used in the reaction in step F is generally (halogen group)/(tertiary amine)=2/1 to 1/2, preferably 1.5/1 to 1/1.5, and more preferably 1.3/1 to 1/1.3, as the molar ratio with the number of moles of the halogen group in the reaction product obtained in the preceding step.

The reaction in step G is carried out optionally in the presence of a catalyst. The catalyst used in the reaction can be exemplified by sodium hydroxide and potassium hydroxide, by alkali metal salts such as potassium carbonate and sodium carbonate, and by quaternary ammonium salts such as tetramethylammonium chloride and tetrabutylammonium bromide. Its amount of use is generally (hydroxyl group)/(catalyst)=1/0.0001 to 1/0.3, preferably 1/0.001 to 1/0.2, and more preferably 1/0.005 to 1/0.1, as the molar ratio with the hydroxyl group (as the hydroxyl value) in the polyalkylene glycol chain-containing monomer with general formula (I). A satisfactory catalytic effect is not obtained when too little catalyst is present, while a greater effect is not obtained when the amount of catalyst is overly large, which is thus uneconomical.

The amount of use for the glycidyltrialkylammonium salt used in the reaction in step G is generally (hydroxyl group)/(glycidyltrialkylammonium salt)=5/1 to 1/5, preferably 3/1 to 1/3, and more preferably 1.5/1 to 1/1.5, as the molar ratio with the hydroxyl group (as the hydroxyl value) in the polyalkylene glycol chain-containing monomer with general formula (I).

The same alkali compound as used in step A can be used for the alkali compound used in the reaction in step H.

With regard to the amount of use for the alkali compound in step H, the molar ratio between the halogen group in the reaction product obtained in step E and the alkali compound is preferably (halogen group)/(alkali compound)=1/1 to 1/100. 1/1 to 1/50 is more preferred and 1/1 to 1/20 is even more preferred.

The cationic group-containing monomer of the present invention can be produced by the processes described above, while a purification step may be incorporated as necessary. This is preferred because the execution of a purification step by extraction or washing can lower the amount of crosslinking component that causes the occurrence of gelation during polymerization.

Among the production processes (1-1) to (1-6) described above, the previously described production processes (1-1) to (1-3), (1-5), and (1-6) are preferred because the starting materials are inexpensive and these processes are also convenient from a production standpoint. In addition, the production process (1-1) is preferred for its ability to inhibit the production of the crosslinking component that causes the occurrence of gelation during polymerization; the production process (1-2) is preferred for the ease of selection of the counteranion in the cationic group-containing monomer; and the production process (1-3) is preferred because little waste is produced by the reactions. The production process (1-1) is more preferred among the preceding.

After the cationic group-containing monomer of the present invention has been obtained by a production process as described above, the counteranion therein can be changed to a desired anionic species by an ion-exchange process, but the introduction of the desired anionic species by a judicious selection of the starting material used in the particular production process is preferred for its convenience. That is, the anion in the tertiary amine salt used in step (B) in production processes (1-1) and (1-5), the counteranion due to the quaternizing agent in step (D) in production processes (1-2) and (1-6), the halogen atom from the epihalohydrin in step (E) in production process (1-3), and the counteranion in the glycidyltrialkylammonium salt in step (G) in production process (1-4) can be introduced as the counteranion in the cationic group-containing monomer.

[Processes for Producing the Amino Group-Containing Monomer of the Present Invention]

The amino group-containing monomer of the present invention can be produced by an applicable production process as normally used and there are no particular limitations thereon, but is preferably produced by a process according to the following production processes (2-1) to (2-4). These processes can produce the amino group-containing monomer of the present invention in high yields.

Thus, a preferred process (2-1) for producing the amino group-containing monomer of the present invention is a process for producing the amino group-containing monomer comprising (i) a step of reacting a polyalkylene glycol chain-containing monomer given by general formula (I) and an epihalohydrin and an alkali compound (step I) and (ii) a step of reacting the reaction product obtained in step I with a secondary amine (step J).

A preferred process (2-2) for producing the amino group-containing monomer of the present invention is a process for producing the amino group-containing monomer comprising (i) a step of reacting a polyalkylene glycol chain-containing monomer with general formula (I) and an epihalohydrin in the presence of a catalyst (step K), (ii) a step of reacting the reaction product obtained in step K with an alkali compound (step L), and (iii) a step of reacting the reaction product obtained in step L with a secondary amine (step J).

A preferred process (2-3) for producing the amino group-containing monomer of the present invention is a process for producing the amino group-containing monomer comprising (i) a step of reacting a polyalkylene glycol chain-containing monomer with general formula (I) and an epihalohydrin in the presence of a catalyst (step K) and (ii) a step of reacting the reaction product obtained in step K with a secondary amine (step M).

A preferred process (2-4) for producing the amino group-containing monomer of the present invention is a process for producing the amino group-containing monomer comprising (i) a step of reacting a polyalkylene glycol chain-containing monomer with general formula (I) with an N-(dialkylaminomethyl)oxirane (step N).

The preferred embodiments of $R^0$, $R^1$, $Y^1$, and n in the polyalkylene glycol chain-containing monomer with general formula (I) in production processes (2-1) to (2-4) are the same as the preferred embodiments of $R^0$, $R^1$, $Y^1$, and n for general formula (14).

The polyalkylene glycol chain-containing monomer with general formula (I), the epihalohydrin, the alkali compound, and the secondary amine used in the preceding processes for producing the amino group-containing monomer are the same as the polyalkylene glycol chain-containing monomer with general formula (I), the epihalohydrin, the alkali compound, and the secondary amine used in the previously described processes for producing the cationic group-containing monomer of the present invention.

The N-(dialkylaminomethyl)oxirane in production process (2-4) preferably has a structure represented by the following general formula (24)

(where, $R^5$ and $R^6$ are the same or different from one another and represent a hydrogen atom or a $C_{1-20}$ organic group and $R^5$ and $R^6$ may be bonded to each other to form a cyclic structure).

The preferred embodiments for $R^5$ and $R^6$ in general formula (24) are the same as the preferred embodiments of $R^5$ and $R^6$ for general formula (14).

The N-(dialkylaminomethyl)oxirane can be specifically exemplified by N-(dimethylaminomethyl)oxirane, N-(diethylaminomethyl)oxirane, N-(di-n-butylaminomethyl)oxirane, and N-(dihydroxyethylaminomethyl)oxirane.

Production processes (2-1) to (2-4) are thus represented by the following reaction formulas.

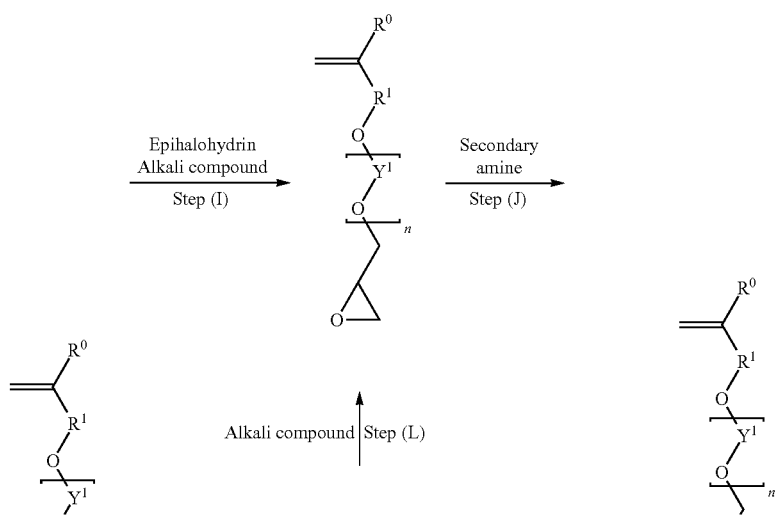

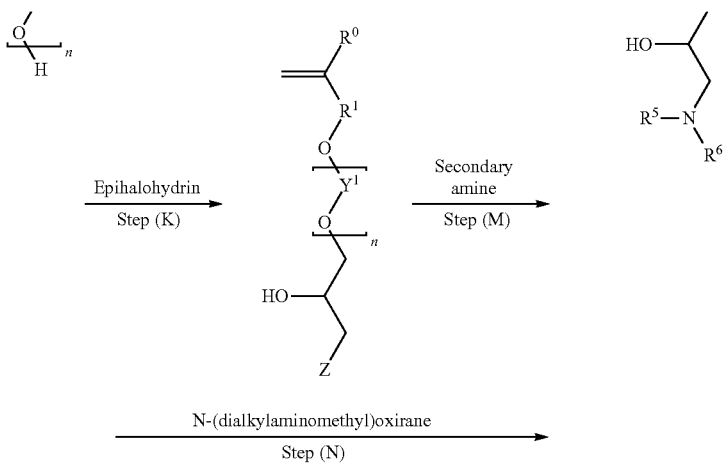

The reaction conditions and embodiments for each of the essential steps I to N in production processes (2-1) to (2-4) are described in detail in the following.

The preferred reaction conditions and embodiments for steps I, J, K, and L are the same as the preferred reaction conditions and embodiments for steps A, C, E, and H, respectively, in the previously described processes of producing the cationic group-containing monomer.

The reactions in steps M and N proceed in good yields when run in the absence of solvent and this is more preferred from the standpoint of the volumetric efficiency; however, they can also be run in the presence of a solvent. A single solvent may be used by itself or two or more solvents may be used in combination. The amount of solvent used is not particularly limited, but is generally in the range from 0.005- to 5-fold on a mass basis and preferably 0.01- to 3-fold on a mass basis, with reference in step M to the reaction product obtained in step K and with reference in step N to the polyalkylene glycol chain-containing monomer with general formula (I).

Except for the requirement that the solvent should not have a negative effect on the reaction, there are no particular limitations on the solvent usable in the reaction in step M, and this solvent can be exemplified by water; alcohols such as methanol, ethanol, and isopropanol; ethers such as diethyl ether, tetrahydrofuran, and dioxane; and ketones such as acetone and methyl ethyl ketone.

Except for the requirement that the solvent should not have a negative effect on the reaction, there are no particular limitations on the solvent usable in the reaction in step N, and this solvent can be exemplified by hydrocarbons such as hexane, octane, decane, cyclohexane, benzene, and toluene; ethers such as diethyl ether, tetrahydrofuran, and dioxane; ketones such as acetone and methyl ethyl ketone; and chlorinated hydrocarbons such as dichloromethane and dichloroethane.

When a catalyst is used in step K, the reaction of step M may be directly run in the presence of the residual catalyst.

The reactions in steps M and N may be run under an air atmosphere or may be run under an inert gas atmosphere. These reactions may be run under reduced pressure, at atmospheric pressure, or under an overpressure. The reaction temperature is generally 0 to 200° C., preferably 15 to 150° C., and more preferably 30 to 100° C. Viewed from the perspective of the fluidity of the reactants, i.e., the polyalkylene glycol chain-containing monomer with general formula (I) and the reaction product obtained in step K, the reactions are preferably run at a temperature that does not produce problems with stirring. The reaction time is generally from 0.1 to 50 hours, preferably from 0.5 to 30 hours, and more preferably from 1 to 15 hours.

The reactions in steps M and N may be run using a batch or continuous regime; for example, these reactions may be run in a tank-type or pipe-type reactor apparatus. The reaction in step M is preferably followed by a step of, for example, desalting. The desalting step can be carried out by, e.g., separation by sedimentation, centrifugal separation, filtration, washing, and so forth, and is not particularly limited. The conditions for running the desalting step should result in a suitable execution that thoroughly removes the salt, and execution at a temperature of 15° C. to 100° C. is preferred from the standpoint of obtaining a satisfactory separation rate.

The amount of use for the secondary amine used in the reaction in step M is preferably (halogen group)/(secondary amine)=2/1 to 1/2, more preferably 1.7/1 to 1/1.7, and even more preferably 1.4/1 to 1/1.4, as the molar ratio with the number of moles of the halogen group in the reaction product obtained in step K.

The reaction in step N is carried out optionally in the presence of a catalyst. The same catalysts as indicated for use in step G can be used as the catalyst for this reaction. Its amount of use is preferably (hydroxyl group)/(catalyst)=1/0.0001 to 1/0.3, more preferably 1/0.001 to 1/0.2, and even more preferably 1/0.005 to 1/0.1, as the molar ratio with the hydroxyl group (as the hydroxyl value) in the polyalkylene glycol chain-containing monomer with general formula (I). A satisfactory catalytic effect is not obtained when too little catalyst is present, while a greater effect is not obtained when the amount of catalyst is overly large, which is thus uneconomical.

The amount of N-(dialkylaminomethyl)oxirane used in the reaction in step N is preferably (hydroxyl group)/(N-(dialkylaminomethyl)oxirane)=5/1 to 1/5, more preferably 3/1 to 1/3, and even more preferably 1.5/1 to 1/1.5, as the molar ratio with the hydroxyl group (as the hydroxyl value) in the polyalkylene glycol chain-containing monomer with general formula (I).

The amino group-containing monomer of the present invention can be produced by the processes described above, while a purification step may be incorporated as necessary. This is preferred because the execution of a purification step by extraction or washing can lower the amount of crosslinking component that causes the occurrence of gelation during polymerization.

Among the production processes (2-1) to (2-4) described above, the previously described production processes (2-1) to (2-3) are preferred because the starting materials and catalysts are inexpensive and these processes are also convenient from a production standpoint. Among these, the production process (2-1) is particularly preferred for its ability to inhibit the production of the crosslinking component that causes the occurrence of gelation during polymerization.

[Processes for Producing the Sulfonic Acid Group-Containing Monomer of the Present Invention]

The previously described sulfonic acid group-containing monomer can be produced by an applicable production process as normally used and there are no particular limitations thereon, but is preferably produced by a process according to the following production processes (3-1) to (3-4). These processes can produce the sulfonic acid group-containing monomer of the present invention in high yields.

Thus, a preferred process (3-1) for producing the sulfonic acid group-containing monomer of the present invention is a process for producing the sulfonic acid group-containing monomer comprising (i) a step of reacting a polyalkylene glycol chain-containing monomer given by general formula (I) and an epihalohydrin and an alkali compound (step O) and (ii) a step of reacting the reaction product obtained in step O with a sulfurous acid compound (step P).

A preferred process (3-2) for producing the sulfonic acid group-containing monomer of the present invention is a process for producing the sulfonic acid group-containing monomer comprising (i) a step of reacting a polyalkylene glycol chain-containing monomer with general formula (I) and an epihalohydrin in the presence of a catalyst (step Q), (ii) a step of reacting the reaction product obtained in step Q with an alkali compound (step R), and (iii) a step of reacting the reaction product obtained in step R with a sulfurous acid compound (step P).

A preferred process (3-3) for producing the sulfonic acid group-containing monomer of the present invention is a process for producing the sulfonic acid group-containing monomer comprising (i) a step of reacting a polyalkylene glycol chain-containing monomer with general formula (I) and an epihalohydrin in the presence of a catalyst (step Q) and (ii) a step of reacting the reaction product obtained in step Q with a sulfurous acid compound (step S).

A preferred process (3-4) for producing the sulfonic acid group-containing monomer of the present invention is a process for producing the sulfonic acid group-containing monomer comprising (i) a step of reacting a polyalkylene glycol chain-containing monomer with general formula (I) with an oxiranemethanesulfonic acid (salt) (step T).

The preferred embodiments of $R^0$, $R^1$, $Y^1$, and n in the polyalkylene glycol chain-containing monomer with general formula (I) in production processes (3-1) to (3-4) are the same as the preferred embodiments of $R^0$, $R^1$, $Y^1$, and n for general formula (16).

The polyalkylene glycol chain-containing monomer with general formula (I), the epihalohydrin, and the alkali compound used in the preceding processes for producing the sulfonic acid group-containing monomer are the same as the polyalkylene glycol chain-containing monomer with general formula (I), the epihalohydrin, and the alkali compound used in the previously, described processes for producing the cationic group-containing monomer of the present invention.

The sulfurous acid compound in production processes (3-1) to (3-3) is preferably sulfurous acid, bisulfite, dithionous acid, metabisulfite, and salts of the preceding. This sulfurous acid compound can be used as the acid (that is, sulfurous acid is used), but is preferably used as the salt from the standpoints of handling and raising the yield. This salt is preferably, for example, the sodium salt, potassium salt, lithium salt, ammonium salt, or quaternary ammonium salt.

This sulfurous acid compound can be exemplified by lower oxides such as sodium bisulfite, potassium bisulfite, sodium dithionite, potassium dithionite, sodium metabisulfite, and potassium metabisulfite and by their salts. Sodium bisulfite and sodium metabisulfite are particularly preferred among the preceding because they are inexpensive at an industrial level.

The oxiranemethanesulfonic acid (salt) in production process (3-4) preferably has a structure represented by the following general formula (25)

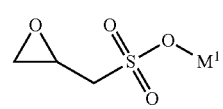

(25)

(where, $M^1$ represents a hydrogen atom or a monovalent cation).

The preferred embodiments for $M^1$ in general formula (25) are the same as the preferred embodiments of $M^1$ for general formula (16).

This oxiranemethanesulfonic acid (salt) can be specifically exemplified by oxiranemethanesulfonic acid, sodium oxiranemethanesulfonate, potassium oxiranemethanesulfonate, ammonium oxiranemethanesulfonate, and tetrabutylammonium oxiranemethanesulfonate.

Production processes (3-1) to (3-4) are thus represented by the following reaction formulas.

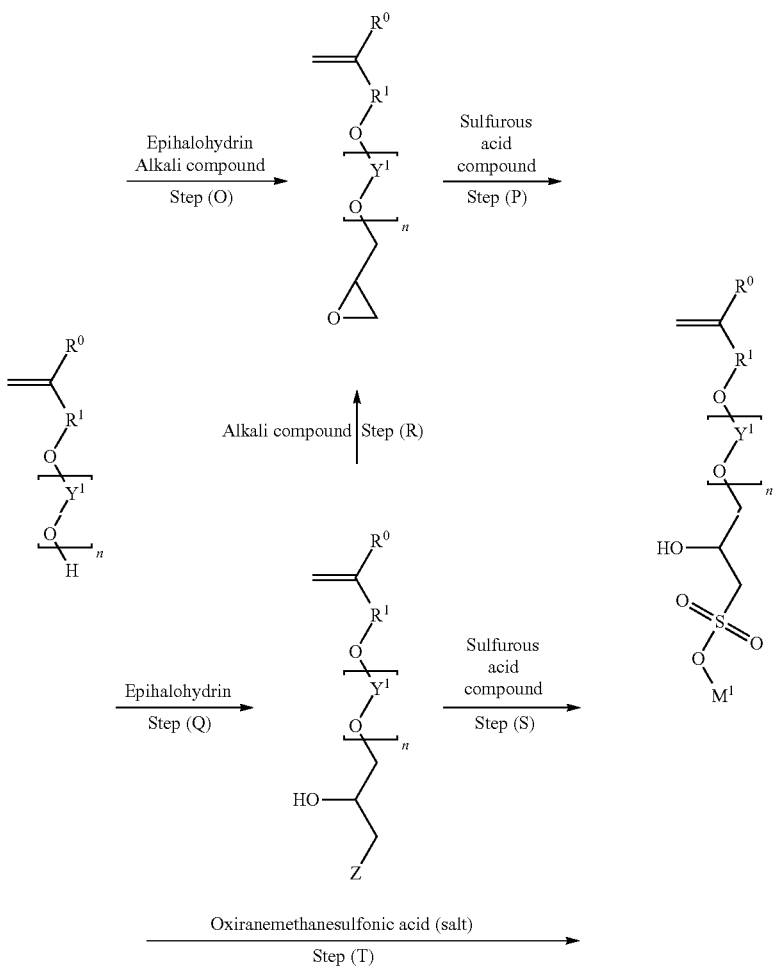

The reaction conditions and embodiments for each of the essential steps O to T in production processes (3-1) to (3-4) are described in detail in the following.

The preferred reaction conditions and embodiments for steps O, Q, and R are the same as the preferred reaction conditions and embodiments for steps A, E, and H, respectively, in the previously described processes of producing the cationic group-containing monomer.

The reactions in steps P, S, and T are run optionally in the presence of a solvent. A single solvent may be used by itself or two or more solvents may be used in combination. The amount of solvent used is not particularly limited, but is generally in the range from 0.005- to 5-fold on a mass basis and preferably 0.01- to 3-fold on a mass basis, with reference insteps P and S to the reaction product obtained in the preceding step and with reference in step T to the polyalkylene glycol chain-containing monomer with general formula (I).

Except for the requirement that the solvent should not have a negative effect on the reaction, there are no particular limitations on the solvent usable in the reaction in steps P and S, and this solvent can be exemplified by water; alcohols such as methanol, ethanol, and isopropanol; ethers such as diethyl ether, tetrahydrofuran, and dioxane; and ketones such as acetone and methyl ethyl ketone.

Except for the requirement that the solvent should not have a negative effect on the reaction, there are no particular limitations on the solvent usable in the reaction in step T, and this solvent can be exemplified by hydrocarbons such as hexane, octane, decane, cyclohexane, benzene, and toluene; ethers such as diethyl ether, tetrahydrofuran, and dioxane; ketones such as acetone and methyl ethyl ketone; and chlorinated hydrocarbons such as dichloromethane and dichloroethane.

When a catalyst is used in the preceding step, the reactions of steps P and S may be directly run in the presence of the residual catalyst.

The reactions in steps P, S, and T may be run under an air atmosphere or may be run under an inert gas atmosphere. These reactions may be run under reduced pressure, at atmospheric pressure, or under an overpressure. The reaction temperature is generally 0 to 200° C., preferably 15 to 150° C., and more preferably 30 to 100° C. Viewed from the perspective of the fluidity of the reactants, i.e., the reaction product obtained in the preceding step and the polyalkylene glycol chain-containing monomer with general formula (I), the reactions are preferably run at a temperature that does not produce problems with stirring. The reaction time is generally from 0.1 to 50 hours, preferably from 0.5 to 30 hours, and more preferably from 1 to 15 hours.

The reactions in steps P, S, and T may be run using a batch or continuous regime; for example, these reactions may be run in a tank-type or pipe-type reactor apparatus.

The reaction in step S is preferably followed by a step of, for example, desalting. The desalting step can be carried out by, e.g., separation by sedimentation, centrifugal separation, filtration, washing, and so forth, and is not particularly limited. The conditions for running the desalting step should result in a suitable execution that thoroughly removes the salt, and execution at a temperature of 15° C. to 100° C. is preferred from the standpoint of obtaining a satisfactory separation rate.

Adjustment of the pH is performed on an optional basis in the reactions of steps P and S. This pH adjustment may be done prior to the reaction or during the reaction and is preferably performed by adding an alkali compound. This alkali compound can be exemplified by alkali metal hydroxides such as sodium hydroxide and potassium hydroxide, by alkaline-earth metal hydroxides such as calcium hydroxide, and by ammonia and amines.

The amount of use for the sulfurous acid compound used in the reactions in steps P and S is preferably (glycidyl group or halogen group)/(sulfurous acid compound)=2/1 to 1/2, more preferably 1.7/1 to 1/1.7, and even more preferably 1.4/1 to 1/1.4, as the molar ratio in the case of step P with the number of moles of the glycidyl group in the reaction product obtained in the preceding step and in the case of step S with the number of moles of the halogen group in the reaction product obtained in the preceding step. The sulfurous acid compound may be used in the form of the aqueous solution.

The reaction in step T is carried out optionally in the presence of a catalyst. The same catalysts as indicated for use in step G can be used as the catalyst for this reaction. Its amount of use is preferably (hydroxyl group)/(catalyst)=1/0.0001 to 1/0.3, more preferably 1/0.001 to 1/0.2, and even more preferably 1/0.005 to 1/0.1, as the molar ratio with the hydroxyl group (as the hydroxyl value) in the polyalkylene glycol chain-containing monomer with general formula (I). A satisfactory catalytic effect is not obtained when too little catalyst is present, while a greater effect is not obtained when the amount of catalyst is overly large, which is thus uneconomical.

The amount of the oxiranemethanesulfonic acid (salt) used in the reaction in step T is preferably (hydroxyl group)/(oxiranemethanesulfonic acid (salt))=5/1 to 1/5, more preferably 3/1 to 1/3, and even more preferably 1.5/1 to 1/1.5, as the molar ratio with the hydroxyl group (as the hydroxyl value) in the polyalkylene glycol chain-containing monomer with general formula (I).

The sulfonic acid group-containing monomer of the present invention can be produced by the processes described above, while a purification step may be incorporated as necessary. This is preferred because the execution of a purification step by extraction or washing can lower the amount of crosslinking component that causes the occurrence of gelation during polymerization.

Among the production processes (3-1) to (3-4) described above, the previously described production processes (3-1) to (3-3) are preferred because the starting materials and catalysts are inexpensive and these processes are also convenient from a production standpoint. Among these, the production process (3-1) is particularly preferred for its ability to inhibit the production of the crosslinking component that causes the occurrence of gelation during polymerization.

[Processes for Producing the Organic Ether Group-Containing Monomer of the Present Invention]

The previously described organic ether group-containing monomer can be produced by an applicable production process as normally used and there are no particular limitations thereon, but is preferably produced by a process according to the following production processes (4-1) and (4-2). These processes can produce the organic ether group-containing monomer in high yields.

Thus, a preferred process (4-1) for producing the organic ether group-containing monomer of the present invention is a process for producing the organic ether group-containing monomer comprising (i) a step of reacting a polyalkylene glycol chain-containing monomer given by general formula (I) and an epihalohydrin and an alkali compound (step U) and (ii) a step of reacting the reaction product obtained in step U (glycidyl group-containing polyalkylene glycol-type monomer) with a hydroxyl group-containing compound (step V).

A preferred process (4-2) for producing the organic ether group-containing monomer of the present invention is a process for producing the organic ether group-containing monomer comprising (i) a step of reacting a polyalkylene glycol chain-containing monomer with general formula (I) and an epihalohydrin in the presence of a catalyst (step W), (ii) a step of reacting the reaction product obtained in step W with an alkali compound (step X), and (iii) a step of reacting the reaction product obtained in step X (glycidyl group-containing polyalkylene glycol-type monomer) with a hydroxyl group-containing compound (step V).

Thus, a process for producing an organic ether group-containing polyalkylene glycol-type monomer with general formula (19), characterized by reacting a hydroxyl group-containing compound with a glycidyl group-containing polyalkylene glycol-type monomer with general formula (1), is also one of the inventions disclosed herein.

The preferred embodiments of $R^0$, $R^1$, $Y^1$, and n in the polyalkylene glycol chain-containing monomer with general formula (I) in production processes (4-1) and (4-2) are the same as the preferred embodiments of $R^0$, $R^1$, $Y^1$, and n for general formula (18).

The polyalkylene glycol chain-containing monomer with general formula (I), the epihalohydrin, and the alkali compound used in the preceding processes for producing the organic ether group-containing monomer are the same as the polyalkylene glycol chain-containing monomer with general formula (I), the epihalohydrin, and the alkali compound used in the previously described processes for producing the cationic group-containing monomer of the present invention.

The hydroxyl group-containing compound in production processes (4-1) and (4-2) is preferably a hydroxyl group-containing compound having the structure represented by the following general formula (26)

$$R^7\text{—OH} \quad (26)$$

($R^7$ in the formula is a $C_{1-20}$ organic group).

The preferred embodiments for $R^7$ in general formula (26) are the same as the preferred embodiments of $R^7$ for general formula (18).

This hydroxyl group-containing compound can be specifically exemplified by alkyl alcohols such as methanol, ethanol, n-propanol, isopropanol, n-butanol, isobutanol, t-butanol, octanol, lauryl alcohol, stearyl alcohol, and 2-ethylhexanol; cycloalkyl alcohols such as cyclopentanol and cyclohexanol; aryl alcohols such as benzyl alcohol; alkylene glycol monoalkyl ethers such as 2-methoxyethanol, 2-ethoxyethanol, polyethylene glycol monomethyl ether, and polypropylene glycol monomethyl ether; phenols such as phenol, p-methoxyphenol, and naphthol; and hydroxycarboxylic acids such as glycolic acid, lactic acid, malic acid, and citric acid. The following are preferred among the preceding because they enable the high-yield production of the organic ether group-containing polyalkylene glycol-type monomer: methanol, ethanol, n-butanol, octanol, lauryl alcohol, 2-ethylhexanol, and glycolic acid.

Production processes (4-1) and (4-2) are thus represented by the following reaction formulas.

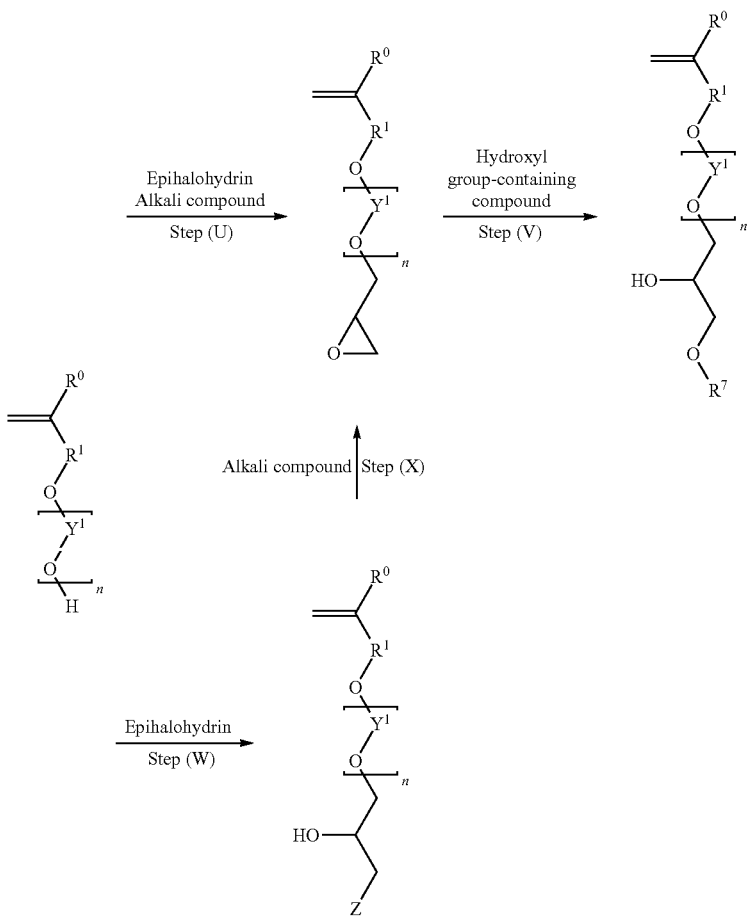

The reaction conditions and embodiments for the essential steps U to X in production processes (4-1) and (4-2) are described in detail in the following.

The preferred reaction conditions and embodiments for steps U, W, and X are the same as the preferred reaction conditions and embodiments for steps A, E, and H, respectively, in the previously described processes of producing the cationic group-containing monomer.

The use amount for the hydroxyl group-containing compound used in step V, expressed as the molar ratio with the glycidyl group in the reaction product obtained in the preceding step (glycidyl group-containing polyalkylene glycol-type monomer), is preferably (glycidyl group)/(hydroxyl group-containing compound)=1/1 to 1/100 and more preferably 1/2 to 1/50 and is particularly preferably 1/3 to 1/20 from the standpoint of being able to produce the organic ether group-containing polyalkylene glycol-type monomer with general formula (18) at higher purities.

The reaction in step V may be run using a catalyst. An acid or an alkali may be used as this catalyst.

This acid may be a Lewis acid or a Brønsted acid wherein a Lewis acid is preferred. The species generally known as Lewis acids can be used as this Lewis acid, for example, boron trifluoride, tin tetrachloride, tin dichloride, zinc chloride, ferric chloride, aluminum chloride, titanium tetrachloride, magnesium chloride, and antimony pentachloride. Its use amount is preferably (glycidyl group)/(acid)=1/0.0001 to 1/0.1, more preferably 1/0.0005 to 1/0.05, and even more preferably 1/0.001 to 1/0.03, as the molar ratio with the glycidyl group of the reaction product obtained in the preceding step (glycidyl group-containing polyalkylene glycol-type monomer). A satisfactory catalytic effect is not obtained when too little catalyst is present, while a greater effect is not obtained when the amount of catalyst is overly large, which is thus uneconomical.

There are no particular limitations on the alkali, but an alkali metal hydroxide such as sodium hydroxide or potassium hydroxide is preferred. The use amount of this alkali compound is preferably (glycidyl group)/(alkali compound)=1/0.001 to 1/1, more preferably 1/0.005 to 1/0.75, and even more preferably 1/0.01 to 1/0.5, as the molar ratio with the glycidyl group in the reaction product obtained in the preceding step (glycidyl group-containing polyalkylene glycol-type monomer). This alkali may also be used in the form of the aqueous solution of the aforementioned alkali metal hydroxides.

The reaction in step V may be run optionally in the presence of a phase-transfer catalyst and/or a solvent.

There are no particular limitations on the type of this phase-transfer catalyst, and it can be exemplified by quaternary ammonium salts such as tetramethylammonium chloride, tetrabutylammonium bromide, and so forth; phosphonium salts such as tetrabutylphosphonium chloride and so forth; and crown ethers such as 15-crown-5 and so forth.

When a phase-transfer catalyst is used, its amount of use is preferably (glycidyl group)/(phase-transfer catalyst)=1/0.0001 to 1/0.3, more preferably 1/0.001 to 1/0.2, and even more preferably 1/0.005 to 1/0.1, as the molar ratio with the glycidyl group in the reaction product obtained in the preceding step (glycidyl group-containing polyalkylene glycol-type monomer). A satisfactory catalytic effect is not obtained when too little catalyst is present, while a greater effect is not obtained when the amount of catalyst is overly large, which is thus uneconomical.

The reaction in step V proceeds in good yields when run in the absence of solvent and this is more preferred from the standpoint of the volumetric efficiency; however, it can also be run in the presence of a solvent. Except for the requirement that the solvent should not have a negative effect on the reaction, there are no particular limitations on the solvents that can be used, and this solvent can be exemplified by hydrocarbons such as hexane, octane, decane, cyclohexane, benzene, and toluene; ethers such as diethyl ether, tetrahydrofuran, and dioxane; ketones such as acetone and methyl ethyl ketone; and chlorinated hydrocarbons such as dichloromethane and dichloroethane. A single solvent may be used by itself or two or more solvents may be used in combination. The amount of solvent used is not particularly limited, but is generally in the range from 0.005- to 5-fold on a mass basis and preferably 0.01- to 3-fold on a mass basis, with reference to the reaction product obtained in the preceding step (glycidyl group-containing polyalkylene glycol-type monomer).

When a catalyst is used in the preceding step, the reaction in step V may be directly run in the presence of the residual catalyst. The reaction in step V may be run under an air atmosphere or may be run under an inert gas atmosphere. This reaction may be run under reduced pressure, at atmospheric pressure, or under an overpressure. The reaction temperature is generally 0 to 200° C., preferably 15 to 160° C., and more preferably 30 to 120° C. The reaction time is generally from 0.1 to 50 hours, preferably from 0.5 to 30 hours, and more preferably from 1 to 15 hours. The reaction in step V may be run using a batch or continuous regime; for example, it may be run in a tank-type or pipe-type reactor apparatus. The reaction is preferably followed by a step of removing the excess hydroxyl group-containing compound. The excess hydroxyl group-containing compound can be easily removed by, for example, washing, distillation, evaporation, and so forth. In addition, the reaction may also be followed by a step of removing the catalyst.

The organic ether group-containing monomer of the present invention can be produced by the processes described above, while a purification step may be incorporated as necessary. This is preferred because the execution of a purification step by extraction or washing can lower the amount of crosslinking component that causes the occurrence of gelation during polymerization.

Between the production processes (4-1) and (4-2) described above, the previously described production process (4-1) is particularly preferred for its ability to inhibit the production of the crosslinking component that causes the occurrence of gelation during polymerization.

The water-soluble polymer yielded by the polymerization of water-soluble monomer of the present invention is described in detail below.

The cationic polymer yielded by the polymerization of the cationic group-containing monomer of the present invention is considered in detail first.

[The Cationic Polymer of the Present Invention]

This cationic polymer, which has the cationic group-containing monomer of the present invention as a precursor, must have (i) a structure (structure A) derived from the cationic group-containing monomer of the present invention with general formula (13) and may on an optional basis have (ii) a structure (structure B) that derives from other monomer.

This structure (structure B) deriving from other monomer is a structure formed by the polymerization of a monomer other than the cationic group-containing monomer of the present invention and is a structure in which the polymerizable carbon-carbon unsaturated double bond of the monomer has been converted into a single bond. For example, taking the case of methyl acrylate ($CH_2$=$CHCOOCH_3$), the structure (structure B) deriving from this other monomer is then —$CH_2$—$CH(COOCH_3)$—.

<Composition of the Cationic Polymer of the Present Invention>

As noted above, the cationic polymer of the present invention must have (i) a structure (A) and optionally has (ii) a structure B. The proportions for each, expressed on the basis of 100 mass % of the structures (structure A and structure B) deriving from all the monomer constituting the cationic polymer of the present invention, is preferably at least 1 to not more than 99 mass % for structure A and at least 0 to not more than 99 mass % for structure B, more preferably at least 5 to not more than 95 mass % for structure A and at least 0 to not more than 95 mass % for structure B, and particularly preferably at least 10 to not more than 95 mass % for structure A and at least 0 to not more than 90 mass % for structure B.

In the present invention, the counteranion is not included in the calculation when calculating the mass proportion (mass %) for structures deriving from all the monomers that are cationic group-containing monomers.

The process of producing the cationic polymer yielded by the polymerization of the cationic group-containing monomer of the present invention is described in detail in the following.

[Process of Producing the Cationic Polymer of the Present Invention]

Unless specifically stated otherwise, a process that operates the same as a generally known polymerization process, or a modification thereof, can be used as the process for producing the cationic polymer of the present invention, and the cationic polymer of the present invention can be produced by polymerizing (i) the cationic group-containing monomer of the present invention (also referred to as monomer a) and optionally (ii) other monomer (also referred to as monomer b). A single monomer a or two or more of it may be used, and a single monomer b or two or more of it may be used.

For example, oil-in-water emulsion polymerization, water-in-oil emulsion polymerization, suspension polymerization, dispersion polymerization, precipitation polymerization, solution polymerization, water-based solution polymerization, and bulk polymerization can be used as the specific polymerization process. Among these polymerization processes, the use of water-based solution polymerization and emulsion polymerization is preferred for the high safety they provide and because they enable a lowering of the production costs (polymerization costs).

<The Polymerization Initiator>

The usual polymerization initiators can be used as the polymerization initiator in the polymerization processes cited above, and suitable in this regard are, for example, hydrogen peroxide; persulfates such as sodium persulfate, potassium persulfate, and ammonium persulfate; azo compounds such as 2,2'-azobis(2-amidinopropane) hydrochloride, 4,4'-azobis-4-cyanovaleric acid, azobisisobutyronitrile, and 2,2'-azobis(4-methoxy-2,4-dimethylvaleronitrile); and organoperoxides such as benzoyl peroxide, lauroyl peroxide, peracetic acid, di-t-butyl peroxide, and cumene hydroperoxide. A single one of these polymerization initiators may be used or the polymerization initiator may be used in the form of a mixture of two or more. For example, a hydrogen peroxide/persulfate combination is a preferred embodiment.

<The Chain-Transfer Agent>

The process for producing the cationic polymer of the present invention may optionally employ, within a range that does not negatively affect the polymerization, a chain-transfer agent as an agent for regulating the molecular weight of the polymer. This chain-transfer agent can be specifically exemplified by thiol-type chain-transfer agents such as mercaptoethanol, thioglycerol, thioglycolic acid, 2-mercaptopropionic acid, 3-mercaptopropionic acid, thiomalic acid, octyl thioglycolate, octyl 3-mercaptopropionate, 2-mercaptoethanesulfonic acid, n-dodecyl mercaptan, octyl mercaptan, and butyl thioglycolate; halides such as carbon tetrachloride, methylene chloride, bromoform, and bromotrichloroethane; secondary alcohols such as isopropanol and glycerol; lower oxides such as phosphorous acid, hypophosphorous acid, and their salts (for example, sodium hypophosphite, potassium hypophosphite), as well as sulfurous acid, bisulfite, dithionous acid, metabisulfite, and their salts (for example, sodium bisulfite, potassium bisulfite, sodium dithionite, potassium dithionite, sodium metabisulfite, and potassium metabisulfite); and salts of the preceding. A single one of these chain-transfer agents may be used, or the chain-transfer agent may be used in the form of a mixture of two or more.

The use of sulfurous acid and/or a sulfurous acid salt (referred to hereafter simply as "sulfurous acid (salt)") as described above as the chain-transfer agent is a preferred embodiment for the production process of the present invention, in which case an initiator is used in addition to the sulfurous acid (salt). In addition, a heavy metal ion may also be used in combination as a reaction promoter.

<The Reaction Promoter>

A reaction promoter may be added in the process of producing the cationic polymer of the present invention with the goal, for example, of lowering the amount of use of the initiator. This reaction promoter can be, for example, a heavy metal ion. In the present invention, this heavy metal ion denotes a metal with a specific gravity of at least 4 g/cm$^3$. For example, iron, cobalt, manganese, chromium, molybdenum, tungsten, copper, silver, gold, lead, platinum, iridium, osmium, palladium, rhodium, ruthenium, and so forth, are preferred for this metal ion. A single one of these heavy metals may be used or two or more may be used. Iron is more preferred among the preceding. There are no particular limitations on the ionic valence of this heavy metal ion, and, taking the use of iron for this heavy metal as an example, the iron ion for the initiator may be $Fe^{2+}$ or $Fe^{3+}$ or a combination of both.

There are no particular limitations on the procedure for adding the heavy metal ion, but it is preferably added up to prior to the completion of the dropwise addition of the monomer, while introduction of the entire amount at the start is particularly preferred. The use amount is preferably not more than 100 ppm with reference to the total amount of the reaction solution.

In addition to the compounds described in the preceding, a reducing compound or catalyst for decomposing the polymerization initiator may be added to the reaction system during polymerization in the process for producing the cationic polymer of the present invention. This catalyst for decomposing the polymerization initiator can be exemplified by metal halides such as lithium chloride and lithium bromide; metal oxides such as titanium oxide and silicon dioxide; the metal salts of inorganic acids such as hydrochloric acid, hydrobromic acid, perchloric acid, sulfuric acid, and nitric acid; carboxylic acids such as formic acid, acetic acid, propionic acid, butyric acid, isobutyric acid, and benzoic acid and their esters and metal salts; and heterocyclic amines such as pyridine, indole, imidazole, and carbazole and their derivatives. A single one of these decomposition catalysts may be used by itself or two or more may be used in combination.

<The Polymerization Solvent>

With regard to the copolymerization of monomers a and b, the polymerization is preferably carried out in the present invention using a solvent that can dissolve monomers a and b, and water is preferably used for at least 50 mass % of the solvent used. Depending on the particular application, the admixture of an organic solvent may be strictly limited, and the use of water for at least 50 mass % of the solvent used—since this can restrain the amount of organic solvent used for the polymerization—offers the advantage of facilitating distillative removal of the organic solvent after completion of the polymerization.

Solvents usable in mixture with water can be exemplified by lower alcohols such as methanol, ethanol, and isopropyl alcohol; lower ketones such as acetone, methyl ethyl ketone, and diethyl ketone; ethers such as dimethyl ether and dioxane; and amides such as dimethylformaldehyde. A single one of these solvents may be used or the solvent may be used in the form of a mixture of two or more. Viewed from the perspective given above, the amount of water, expressed with reference to the total amount of solvent used, is preferably at least 80 mass % with pure water (i.e., 100 mass %) being most preferred.

The amount of use for the solvent, e.g., water, expressed on the basis of the monomer component of 100 mass %, is preferably 40 to 200 mass %. At least 45 mass % is more preferred and at least 50 mass % is even more preferred. In addition, not more than 180 mass % is more preferred and not more than 150 mass % is even more preferred. The obtained copolymer may have an elevated molecular weight when the amount of solvent use is less than 40 mass %, while at more than 200 mass % the resulting lower concentration of the obtained copolymer may necessitate solvent removal. All or a portion of the solvent may be introduced into the reactor at the start of polymerization, or a portion of the solvent may be added (dropwise) to the reaction system during the polymerization reaction, or, for example, monomer component or initiator may be dissolved in the solvent in advance and the solvent may then be added (dropwise) to the reaction system during the polymerization reaction along with these components.

The following methods, inter alia, are suitable methods for adding, e.g., the monomer component, polymerization initiator, and so forth, to the reactor in the polymerization processes cited above: methods in which all of the monomer component is charged to the reactor and copolymerization is carried out by adding the polymerization initiator to the reactor; methods in which a portion of the monomer component is charged to the reactor and copolymerization is carried out by adding the polymerization initiator and the remaining monomer component to the reactor either continuously or stagewise (continuously is preferred); methods in which the polymerization solvent is introduced into the reactor and all of the monomer component and all of the polymerization initiator are added to the reactor; and methods in which a portion of one selection from monomer a and b is introduced into the reactor and the polymerization is run by adding the polymerization initiator and the remaining monomer component to the reactor (preferably continuously).

The polymerization processes described above may be carried out using a batch or continuous regime.

With regard to the polymerization conditions, e.g., the polymerization temperature and so forth, in the polymerization processes described above, these should be established as appropriate in view of the polymerization procedure, solvent, and polymerization initiator used; however, the polymerization temperature is generally preferably at least 0° C. and preferably not more than 150° C. At least 40° C. is more preferred, at least 60° C. is even more preferred, and at least 80° C. is particularly preferred. In addition, not more than 120° C. is more preferred and not more than 110° C. is even more preferred.

<The Polymerization Time, Polymerization Pressure, and Polymerization pH>

There are no particular limitations on the polymerization time, but 30 to 420 minutes is preferred.

The pressure in the reaction system in the polymerization processes cited above may be normal pressure (atmospheric pressure), reduced pressure, or an overpressure, but, viewed from the perspective of the molecular weight of the obtained copolymer, the polymerization is preferably run under normal pressure or the reactor is sealed and the polymerization is then run under an overpressure. The atmosphere in the reaction system may be an air atmosphere, but is preferably an inert atmosphere and, for example, substitution of the interior of the system with an inert gas, e.g., nitrogen, prior to the initiation of polymerization is preferred.

There are no particular limitations on the pH during polymerization in the polymerizations cited above.

[The Amino Group-Containing Polymer, Sulfonic Acid Group-Containing Polymer, and Organic Ether Group-Containing Polymer of the Present Invention]

For the polymer (or polymer composition) obtained from the amino group-containing monomer of the present invention, the polymer (or polymer composition) obtained from the sulfonic acid group-containing monomer of the present invention, and the polymer (or polymer composition) obtained from the organic ether group-containing monomer of the present invention, their constitution, composition, and production process are also the same as for the cationic polymer (or polymer composition) already described above and can be established as appropriate.

[Applications of the Polymer and Polymer Composition]

The water-soluble polymers (or polymer compositions) obtained from the various water-soluble monomers that have been described in the preceding can be used as, for example, coagulants, flocculants, printing inks, adhesives, soil conditioners (improvers), flame retardants, skin care agents, hair care agents, shampoos and hair sprays, additives for soaps and cosmetics, anion-exchange resins, dye mordants and auxiliaries for fibers and photographic films, pigment spreading agents in paper manufacturing, paper-reinforcing agents, anticorrosion agents, softeners for textiles and paper, additives for lubricating oils, water-treatment agents, fiber-treatment agents, dispersing agents, additives for detergents and cleansers, anti-scaling agents (scale-preventing agents), metal ion sequestrants, thickeners, various types of binders, and emulsifying agents. They can be added and used as a detergent builder in various types of detergents and cleansers for, e.g., clothing, foodware, household applications, hair care applications, body care applications, toothpastes, and automotive applications.

The composition of the present invention containing an intermediate for a water-soluble monomer, having the structure described in the preceding, can as a consequence produce a water-soluble polymer in good yields and can impart to the thusly produced water-soluble polymer the ability to adsorb to dirt or fabric. It is therefore well adapted for use for the production of a water-soluble polyalkylene glycol-type monomer having a polymerizable terminal double bond, that is itself well adapted for use for the production of water-soluble polymers.

Moreover, the water-soluble monomer of the present invention, having the structure described in the preceding, exhibits an excellent copolymerizability with various nonionic monomers, cationic monomers, and anionic monomers. In addition, due to a structure deriving from the water-soluble monomer of the present invention, polymer obtained from the water-soluble monomer of the present invention exhibits, for example, an excellent ability to sequester metal ions and resist gelation during laundering and, when used as a detergent additive, exhibits the properties of an excellent anti-soil redeposition performance, an excellent anti-dye transfer performance, and an excellent compatibility with surfactants.

The process of the present invention for producing water-soluble monomer, having the structure described in the preceding, can as a consequence inhibit the production of secondary products and can produce water-soluble monomers at high yields and in high selectivities.

BEST MODE FOR CARRYING OUT THE INVENTION

Figure 1:
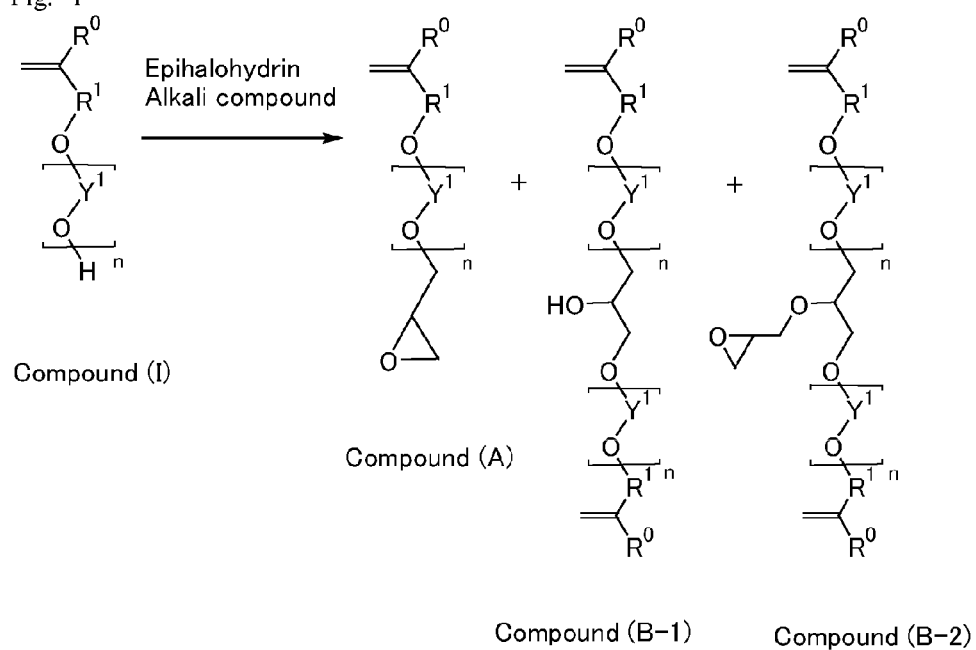
FIG. 1 is a reaction formula that shows an outline of the reaction in reaction step (i-a)
Figure 2:
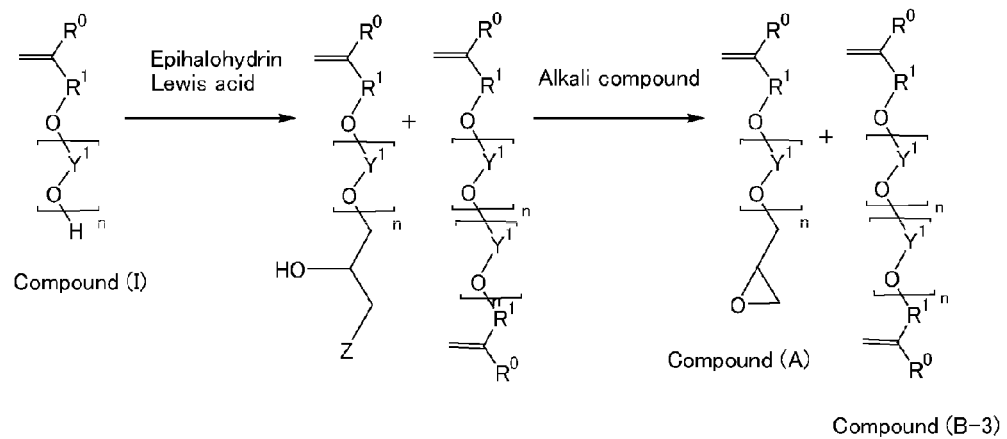
FIG. 2 is a reaction formula that shows an outline of the reactions in reaction step (i-b)

Examples are provided below in order to describe the present invention in greater detail, but the present invention is not limited to only these examples. Unless specifically indicated otherwise, "parts" indicates "weight parts" and "%" indicates "mass %".

The following compounds were used in the examples below as the polyalkylene glycol chain-containing monomer with general formula (I):

an isoprenol/ethylene oxide adduct (average addition=10 moles, also referred to as "IPN10" below) with a hydroxyl value of 106.5 (mg KOH/g);

an isoprenol/ethylene oxide adduct (average addition=25 moles, also referred to as "IPN25" below) with a hydroxyl value of 47.3 (mg KOH/g); and an isoprenol/ethylene oxide adduct (average addition=50 moles, also referred to as "IPN50" below) with a hydroxyl value of 25.5 (mg KOH/g).

Analyses and evaluations were carried out as follows in the examples and comparative examples below.

<Quantitation of the Intermediate Composition>

The IPN10 and terminal glycidylation product from IPN10 (IPEG10) were determined by high-performance liquid chromatography using the conditions given below. The cationic group-containing monomer (IPEC10) was determined by quantitation of the corresponding IPEG10 and from its conversion rate.
measurement instrumentation: from Hitachi High Technologies Corporation
column: Capcell Pak C18 MGII (internal diameter: 4.6 mm× length: 250 mm, particle diameter: 5 μm) from Shiseido Co., Ltd.
eluent: 0.1 mass % formic acid/acetonitrile=6/4 (volumetric ratio)
flow rate: 1.0 mL/min
column temperature: 40° C.
detector: RI, UV (210 nm)
calibration curve: constructed using IPN10, which was the starting alcohol for the reaction. The amount was calculated by making the detected intensity for IPEG10 the same as for IPN10.
<Quantitation of the Secondary Product>
The secondary product in the composition containing an intermediate for a water-soluble monomer was determined by high-performance liquid chromatography using the conditions given below.
measurement instrumentation: 2695 from Waters Corporation
column: Capcell Pak C18 MGII (internal diameter: 1.5 mm× length: 150 mm, particle diameter: 5 μm) from Shiseido Co., Ltd.
eluent: 0.1 mass % formic acid/acetonitrile=6/4 (volumetric ratio)
flow rate: 0.2 mL/min
column temperature: 30° C.
UV detector: 210 nm
calibration curve: constructed using IPN10, which was the starting alcohol for the reaction. The amount was calculated by making the detected intensity for the secondary product 2-fold that of the IPN10.
<The Polymerization Test>
Trimethylamine hydrochloride was reacted with the intermediate-containing composition containing IPEG10 to synthesize a water-soluble monomer-containing composition containing the corresponding IPEC10 and polymerization testing was carried out. In this polymerization test, IPEC10 and hydroxyethyl acrylate were charged at a component ratio of 1/2 as the molar ratio and a static polymerization was carried out. Sodium persulfate was used as the reaction initiator and polymerization was carried out at a reaction temperature of 80° C. The obtained polymer was subjected to a test of its adsorbability to dirt.
<Test of the Adsorbability to Dirt>
An aqueous solution containing 0.3% polymer as the solids fraction was prepared. The Class 11 (Kanto loam) JIS Z 8901 Test Powder 1 was introduced at 5% into the polymer-containing solution; stirring was performed for 20 minutes at room temperature; the clay was filtered using a filter; and the absorbance was measured at 210 nm using a UV-Visible spectrophotometer (measurement instrumentation: UV-1650PC from Shimadzu). For the blank, the same test was performed using pure water instead of the polymer-containing aqueous solution. The adsorbability to dirt was determined from the measurement results using the following equation.

adsorbability to dirt(%)=[{(absorbance of the polymer-containing aqueous solution after testing)−(absorbance of the blank)}/(absorbance of the polymer-containing aqueous solution prior to testing)]×100

It was confirmed beforehand that the absorbance and the polymer concentration in the aqueous solution resided in a proportional relationship at the measurement wavelength of 210 nm.
<Measurement of the Solids Fraction>
The polymer of the present invention (1.0 g water added to 1.0 g polymer composition of the present invention) was dried by standing for 1 hour under a nitrogen atmosphere in an oven heated to 130° C. The solids fraction (%) and the volatile component (%) were calculated from the weight change pre- versus post-drying.

Example 1

200.2 g IPN10 with the following chemical formula (27)

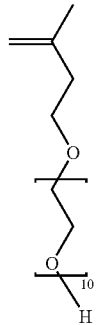

(27)

and 351.6 g epichlorohydrin (ECH) were charged all at once to a one-liter four-neck flask equipped with a stirring paddle, thermometer, and condenser and were heated to an internal temperature of 50° C. while stirring and mixing. To this was gradually added 15.2 g sodium hydroxide flake over 2 hours, and, while maintaining an internal temperature of 50° C., stirring was carried out for an additional 6 hours (regimen B). After the resulting solution had been cooled to room temperature, the precipitated salt was removed by filtration, and the admixed epichlorohydrin and water were removed by reduced-pressure distillation to obtain 199.4 g of an intermediate-containing composition (1-1) that contained IPEG10 having the following chemical formula (28),

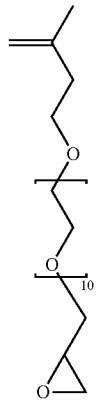

(28)

unreacted IPN10, a secondary product 1 corresponding to the compound (B-1) represented by the following chemical formula (29),

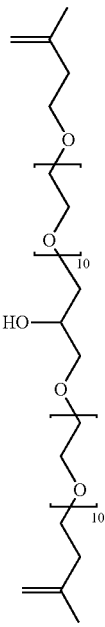

(29)

and a secondary product 2 corresponding to the compound (B-2) represented by the following chemical formula (30).

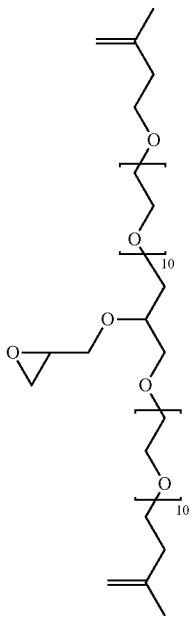

(30)

30.1 g of the intermediate-containing composition (1-1) and 14.5 g of a 30% aqueous trimethylamine hydrochloride solution were introduced all at once into a 100-mL four-neck flask equipped with a stirring paddle, thermometer, and condenser and were stirred for 6 hours at an internal temperature of 50° C. to obtain 44.6 g of a water-soluble monomer-containing composition (1-2) that contained IPEC10. 1.95 g of the water-soluble monomer-containing composition (1-2) that contained IPEC10, 0.49 g hydroxyethyl acrylate, and 9.40 g pure water were then introduced into a 100-mL sample tube equipped with a stirrer and were heated to an internal temperature of 80° C. while stirring and mixing. To this was added 0.42 g of a 15% aqueous sodium persulfate solution and stirring was performed for 1 hour while holding the internal temperature at 80° C. to obtain 12.26 g of a polymer (1-3). Using NMR and gas chromatography, it was confirmed for the obtained polymer that the monomer had been consumed. The adsorbability-to-dirt test was run using the obtained polymer.

Table 1 gives the charged molar ratio for the reactants charged to obtain the intermediate-containing composition (1-1) and the regimen, while Table 2 gives the amounts of IPN10, IPEG10, secondary product 1, and secondary product 2 in the obtained intermediate-containing composition (1-1) and also gives the results of the polymerization test carried out using the water-soluble monomer-containing composition (1-2) and the adsorbability-to-dirt test carried out using the polymer (1-3).

Example 2

1679.8 g IPN10 and 1406.0 g epichlorohydrin (ECH) were charged all at once to a five-liter four-neck flask equipped with a stirring paddle, thermometer, and condenser and were heated to an internal temperature of 50° C. while stirring and mixing. 374.3 g of a 48% aqueous sodium hydroxide solution was added to this by dropwise addition over 2 hours, and, while maintaining an internal temperature of 50° C., stirring was carried out for an additional 4 hours. During the reaction, the pressure in the system was reduced and the reaction was run while distilling out water (regimen A). After the resulting solution had been cooled to room temperature, the precipitated salt was removed by washing with water, and the admixed epichlorohydrin and water were removed by reduced-pressure distillation to obtain 1732.0 g of an intermediate-containing composition (2-1) that contained IPEG10, unreacted IPN10, secondary product 1, and secondary product 2.

1100.0 g of the intermediate-containing composition (2-1) and 532.6 g of a 30% aqueous trimethylamine hydrochloride solution were introduced all at once into a two-liter four-neck flask equipped with a stirring paddle, thermometer, and condenser and were stirred and mixed for 6 hours at an internal temperature of 50° C. to obtain 1632.6 g of a water-soluble monomer-containing composition (2-2) that contained IPEC10. 2.03 g of the water-soluble monomer-containing composition (2-2) that contained IPEC10, 0.51 g hydroxyethyl acrylate, and 9.66 g pure water were then introduced into a 100-mL sample tube equipped with a stirrer and were heated to an internal temperature of 80° C. while stirring and mixing. To this was added 0.44 g of a 15% aqueous sodium persulfate solution and stirring was performed for 1 hour while holding the internal temperature at 80° C. to obtain 12.64 g of a polymer (2-3). Using NMR and gas chromatography, it was confirmed for the obtained polymer that the monomer had been consumed. The adsorbability-to-dirt test was run using the obtained polymer.

Table 1 gives the charged molar ratio for the reactants charged to obtain the intermediate-containing composition (2-1) and the regimen, while Table 2 gives the amounts of IPN10, IPEG10, secondary product 1, and secondary product 2 in the obtained intermediate-containing composition (2-1) and also gives the results of the polymerization test carried out using the water-soluble monomer-containing composition (2-2) and the adsorbability-to-dirt test carried out using the polymer (2-3).

Example 3

802.0 g IPN10 and 422.1 g epichlorohydrin (ECH) were charged all at once to a two-liter four-neck flask equipped with a stirring paddle, thermometer, and condenser and were heated to an internal temperature of 50° C. while stirring and mixing. To this was gradually added 91.2 g sodium hydroxide flake over 2 hours, and, while maintaining an internal temperature of 50° C., stirring was carried out for an additional 5 hours (regimen B). After the resulting solution had been cooled to room temperature, the precipitated salt was removed by filtration, and the admixed epichlorohydrin and water were removed by reduced-pressure distillation to obtain 833.3 g of an intermediate-containing composition (3-1) that contained IPEG10, unreacted IPN10, secondary product 1, and secondary product 2.

30.0 g of the intermediate-containing composition (3-1) and 16.5 g of a 30% aqueous trimethylamine hydrochloride solution were introduced all at once into a 100-mL four-neck flask equipped with a stirring paddle, thermometer, and condenser and were stirred for 6 hours at an internal temperature of 50° C. to obtain 46.5 g of a water-soluble monomer-containing composition (3-2) that contained IPEC10. 2.36 g of the water-soluble monomer-containing composition (3-2) that contained IPEC10, 0.53 g hydroxyethyl acrylate, and 10.25 g pure water were then introduced into a 100-mL sample tube equipped with a stirrer and were heated to an internal temperature of 80° C. while stirring and mixing. To this was added 0.46 g of a 15% aqueous sodium persulfate solution and stirring was performed for 1 hour while holding the internal temperature at 80° C. to obtain 13.60 g of a polymer (3-3). Using NMR and gas chromatography, it was confirmed for the obtained polymer that the monomer had been consumed. The adsorbability-to-dirt test was run using the obtained polymer.

Table 1 gives the charged molar ratio for the reactants charged to obtain the intermediate-containing composition (3-1) and the regimen, while Table 2 gives the amounts of IPN10, IPEG10, secondary product 1, and secondary product 2 in the obtained intermediate-containing composition (3-1) and also gives the results of the polymerization test carried out using the water-soluble monomer-containing composition (3-2) and the adsorbability-to-dirt test carried out using the polymer (3-3).

Comparative Example 1

300.3 g IPN10 and 79.2 g epichlorohydrin (ECH) were charged all at once to a 500-mL four-neck flask equipped with a stirring paddle, thermometer, and condenser and were heated to an internal temperature of 50° C. while stirring and mixing. To this was gradually added 22.8 g sodium hydroxide flake over 2 hours, and, while maintaining an internal temperature of 50° C., stirring was carried out for an additional 4 hours (regimen B). After the resulting solution had been cooled to room temperature, the precipitated salt was removed by filtration, and the admixed epichlorohydrin and water were removed by reduced-pressure distillation to obtain 274.8 g of an intermediate-containing composition (4-1) that contained IPEG10, unreacted IPN10, secondary product 1, and secondary product 2.

30.0 g of the intermediate-containing composition (4-1) and 13.3 g of a 30% aqueous trimethylamine hydrochloride solution were introduced all at once into a 100-mL four-neck flask equipped with a stirring paddle, thermometer, and condenser and were stirred for 6 hours at an internal temperature of 50° C. to obtain 43.3 g of a water-soluble monomer-containing composition (4-2) that contained IPEC10. 1.97 g of the water-soluble monomer-containing composition (4-2) that contained IPEC10, 0.48 g hydroxyethyl acrylate, and 9.04 g pure water were then introduced into a 100-mL sample tube equipped with a stirrer and were heated to an internal temperature of 80° C. while stirring and mixing. To this was added 0.41 g of a 15% aqueous sodium persulfate solution and stirring was performed for 1 hour while holding the internal temperature at 80° C. to obtain 11.90 g of a polymer (4-3). Using NMR and gas chromatography, it was confirmed for the obtained polymer that the monomer had been consumed. The adsorbability-to-dirt test was run using the obtained polymer.

Table 1 gives the charged molar ratio for the reactants charged to obtain the intermediate-containing composition (4-1) and the regimen, while Table 2 gives the amounts of IPN10, IPEG10, secondary product 1, and secondary product 2 in the obtained intermediate-containing composition (4-1) and also gives the results of the polymerization test carried out using the water-soluble monomer-containing composition (4-2) and the adsorbability-to-dirt test carried out using the polymer (4-3).

The following abbreviations are used in Tables 1 and 2.

IPN10: isoprenol/ethylene oxide adduct (average addition=10 moles)

ECH: epichlorohydrin

NaOH: sodium hydroxide

IPEG10: terminal glycidylation product from IPN10

IPEG10 content: mass % of IPEG10 in the intermediate-containing composition

IPN10 content: mass % of IPN10 in the intermediate-containing composition secondary product 1: mol % of secondary product 1, which corresponds to compound (B-1), with reference to IPEG10 and mol % of secondary product 1 with reference to the total for IPEG10 and IPN10 secondary product 2: mol % of secondary product 2, which corresponds to compound (B-2), with reference to IPEG10 and mol % of secondary product 2 with reference to the total for IPEG10 and IPN10 total: mol % of the total of secondary product 1 and secondary product 2 in the intermediate-containing composition with reference to IPEG10 and mol % of the total of secondary product 1 and secondary product 2 in the intermediate-containing composition with reference to the total for IPEG10 and IPN10

TABLE 1

|  | Charged molar ratio | | | |
|---|---|---|---|---|
|  | IPN10 | ECH | NaOH | Regimen |
| Example 1 | 1 | 10 | 1 | B |
| Example 2 | 1 | 5 | 1.5 | A |
| Example 3 | 1 | 3 | 1.5 | B |
| Comparative Example 1 | 1 | 1.5 | 1 | B |

TABLE 2

| | IPEG10 content (mass %) | IPN10 content (mass %) | Secondary product with reference to IPEG10 | | | Secondary product with reference to the total for IPEG10 and IPN10 | | | Polymerization test | Adsorbability to dirt (%) |
| --- | --- | --- | --- | --- | --- | --- | --- | --- | --- | --- |
| | | | Secondary product 1 (mol %) | Secondary product 2 (mol %) | Total (mol %) | Secondary product 1 (mol %) | Secondary product 2 (mol %) | Total (mol %) | | |
| Example 1 | 73 | 21 | 0.4 | 0.2 | 0.6 | 0.3 | 0.2 | 0.4 | ++ (Polymerized) | 49 |
| Example 2 | 71 | 11 | 1.0 | 0.4 | 1.4 | 0.8 | 0.3 | 1.1 | ++ (Polymerized) | 63 |
| Example 3 | 81 | 5 | 1.0 | 1.9 | 2.9 | 0.9 | 1.8 | 2.7 | ++ (Polymerized) | 56 |
| Comparative Example 1 | 67 | 15 | 5.1 | 2.4 | 7.5 | 4.1 | 1.9 | 6.0 | − (Gelled) | — |

The following may be understood from the results in Tables 1 and 2.

It was shown that gelation could be significantly prevented when a polymer was produced using the monomer-containing composition derived from a compound (A)-containing composition containing an intermediate for a water-soluble monomer wherein the compound (B) content in this latter composition was 0.1 to 6.0 mol % with reference to the compound (A) content. It was also shown that polymer produced using the monomer-containing composition derived from such a composition had an excellent capacity to adsorb to dirt.

In the preceding examples, IPN10 was used as the compound (I) in the synthesis of compound (A), epichlorohydrin was used as the epihalohydrin, and sodium hydroxide was used as the alkali compound, and the corresponding secondary products encompassed by compound (B) were produced. However, the mechanism whereby gelation during the polymerization reaction can be stopped by setting a prescribed range for the content of the compound (B) that is secondarily produced during compound (A) synthesis, is entirely the same as in the case in which the polymerization reaction is run using a monomer-containing composition derived from a composition containing an intermediate for a water-soluble monomer that contains a prescribed amount of compound (B). Moreover, the mechanism whereby an excellent adsorbability to dirt is exhibited by a polymer produced using a monomer-containing composition derived from a composition for which the compound (B) content is in a prescribed range, is entirely the same as for a polymer produced using a monomer-containing composition derived from a composition containing an intermediate for a water-soluble monomer that contains a prescribed amount of compound (B). Accordingly, it can be concluded that, based on the results in the preceding examples, the present invention can be applied and its advantageous functional effects can be manifested throughout the entire technical range of the present invention and in the various embodiments disclosed in this Specification.

The isoprenol/ethylene oxide adduct, cationic group-containing monomer, and reaction intermediate were quantitated by liquid chromatography using the conditions described above in <Quantitation of the intermediate composition>. The solids fraction was measured for the polymer as described in <Measurement of the solids fraction>. The weight-average molecular weight of the polymer and the anti-dye transfer performance of the polymer were measured using the following methods.

<Quantitation of the N-vinylpyrrolidone>

The N-vinylpyrrolidone was measured using liquid chromatography under the following conditions.
column: Capcell Pak C18 Type UG120 5 μm, 1.5 mmϕ×250 mm, from Shiseido Co., Ltd.
eluent: methanol/water=1/24 (contained 0.4 mass % sodium 1-heptanesulfonate)
flow rate: 100 μL/min
column oven: 20° C.
injection amount: 10 μL
UV detector: 235 nm <Conditions for Measuring the Weight-Average Molecular Weight>
instrumentation: L-7000 series from Hitachi, Ltd.
detector: RI
column: SHODEX Asahipak GF-310-HQ, GF-710-HQ, GF-1G 7B, from Showa Denko Kabushiki Kaisha
column temperature: 40° C.
flow rate: 0.5 mL/minute
calibration curve: POLYETHYLENE GLYCOL STANDARD from GL Sciences Inc.
eluent: 0.1 N sodium acetate/acetonitrile=3/1 (mass ratio)

<Method for Measuring the Anti-Dye Transfer Performance>

(i) Using an SE2000 Colormeter from Nippon Denshoku Industries Co., Ltd., the whiteness (referred to as the pre-test whiteness of the test fabric) was preliminarily measured by reflectance on JIS cotton fabric (5 cm×5 cm, obtained from the Japanese Standards Association).

(ii) Hard water (150 ppm calcium ion (as calcium carbonate) and 50 ppm magnesium ion (as magnesium carbonate)) was prepared by adding pure water to calcium chloride dihydrate and magnesium chloride hexahydrate.

(iii) A tergotometer was set to 40° C. and the following were introduced into the pot: 500 mL of the hard water, 0.7 g zeolite, 7.7 g of a 5 mass % aqueous sodium carbonate solution, 3.5 g of a 5 mass % aqueous LAS (obtained from Kao Corporation) solution, 3.5 g of the 1% (as the solids fraction) aqueous polymer solution, and, as the dye, 2 g of a 0.25 mass % aqueous solution of Chlorazol Black LF (reagent, obtained from Tokyo Chemical Industry Co., Ltd.). Stirring was carried out for 1 minute at 100 rpm. This was followed by the introduction of 10 sheets of the white fabric and stirring for 30 minutes at 100 rpm.

(iv) The water was drained from the white fabric by hand; 500 mL tap water brought to 40° C. was introduced into the pot; and stirring was performed for 2 minutes at 100 rpm. This was done twice.

(v) A damp cloth was set on the white fabric and drying was done with an iron while stretching out the wrinkles. This was followed by another reflectance measurement of the whiteness of the white fabric using the colormeter indicated above (referred to as the post-test whiteness of the test fabric).

(vi) Using the preceding measurement results, the anti-dye transfer performance was determined with the following formula.

(vii) anti-dye transfer performance (%)=[(post-test whiteness of the test fabric)/(pre-test whiteness of the test fabric)]× 100.

<Method for Evaluating the Compatibility with Surfactant>

A detergent composition containing the test sample (polymer or polymer composition) was produced by blending the following: 40 g SFT-70H (polyoxyethylene alkyl ether from Nippon Shokubai Co., Ltd.), 7.7 g (effective component=5 g) Neopelex F-65 (sodium dodecylbenzenesulfonate, from Kao Corporation), 17.9 g (effective component=5 g) Quartamin 86W (stearyltrimethylammonium chloride, from Kao Corporation), 5 g diethanolamine, 5 g ethanol, 5 g propylene glycol, 1.5 g of the test sample (as the solids fraction), and ion-exchanged water for the balance (the amount of ion-exchanged water was adjusted as appropriate to bring the total of all of the preceding to 100 g, on the basis of the amount of the test sample of the actual amount used).

The components were thoroughly stirred to achieve uniformity; the turbidity value at 25° C. was measured as the turbidity (kaolin turbidity: mg/L) using a turbidimeter (NDH2000 from Nippon Denshoku Industries Co., Ltd.); and an evaluation was performed in accordance with the following evaluation criteria.

Evaluation Criteria

++: kaolin turbidity of at least 0 to less than 50 (mg/L), no visible separation, sedimentation, or turbidity +: kaolin turbidity of at least 50 to less than 200 (mg/L), slight turbidity is visible −: kaolin turbidity of at least 200 (mg/L), turbidity is visible Example 4

Figure 3:
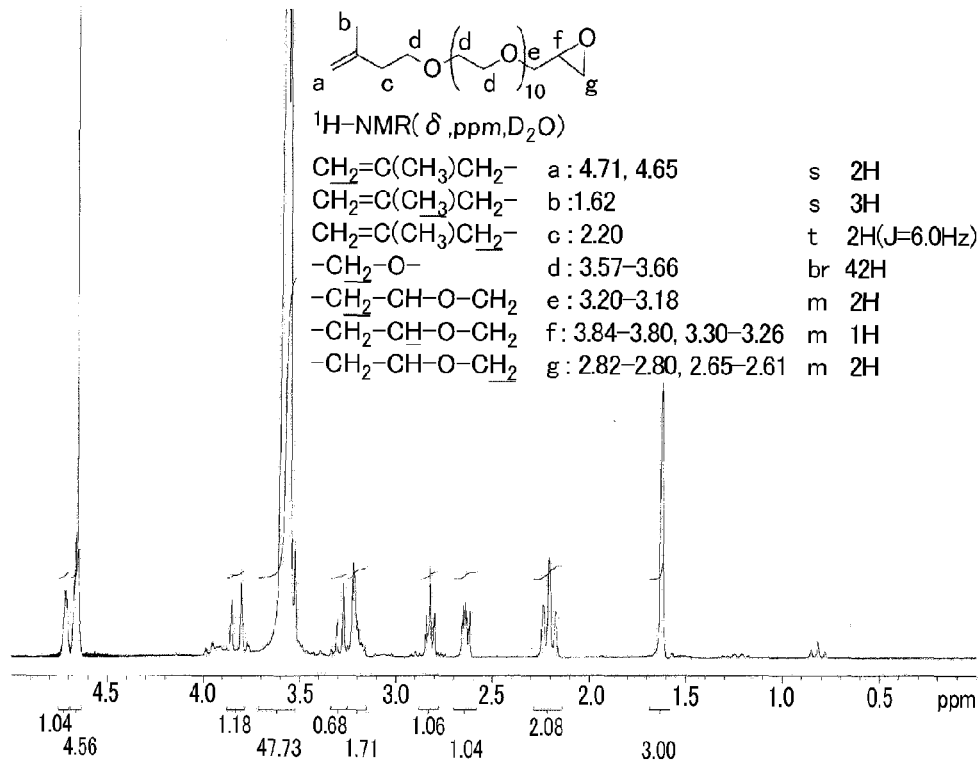
FIG. 3 is a $^1$H-NMR chart of the intermediate [A] for the monomer (1) obtained in Example 4.

100 g IPN10, 52.7 g (0.57 mol) epichlorohydrin, and 3.1 g (0.01 mol) tetrabutylammonium bromide were charged all at once to a 200-mL four-neck flask equipped with a stirring paddle, thermometer, and condenser and were heated to an internal temperature of 40 to 50° C. while stirring and mixing. To was slowly added over 30 minutes 7.6 g (0.19 mol) sodium hydroxide (also referred to below as "NaOH") pellets, and stirring was performed for an additional 5.5 hours while maintaining an internal temperature of 45 to 50° C. After the resulting solution had been cooled to room temperature, the precipitated salt was removed by filtration and the admixed epichlorohydrin and water were removed by reduced-pressure distillation to obtain 102 g of a reaction solution containing 78.5 g intermediate [A], for a yield of 70 mol %. In addition, the production of the intermediate [A], shown in FIG. 3, for the monomer (1) was also confirmed from the $^{1}$H-NMR (that is, a compound with the structure in general formula (31) below in which n is an average of 10).

Figure 4:
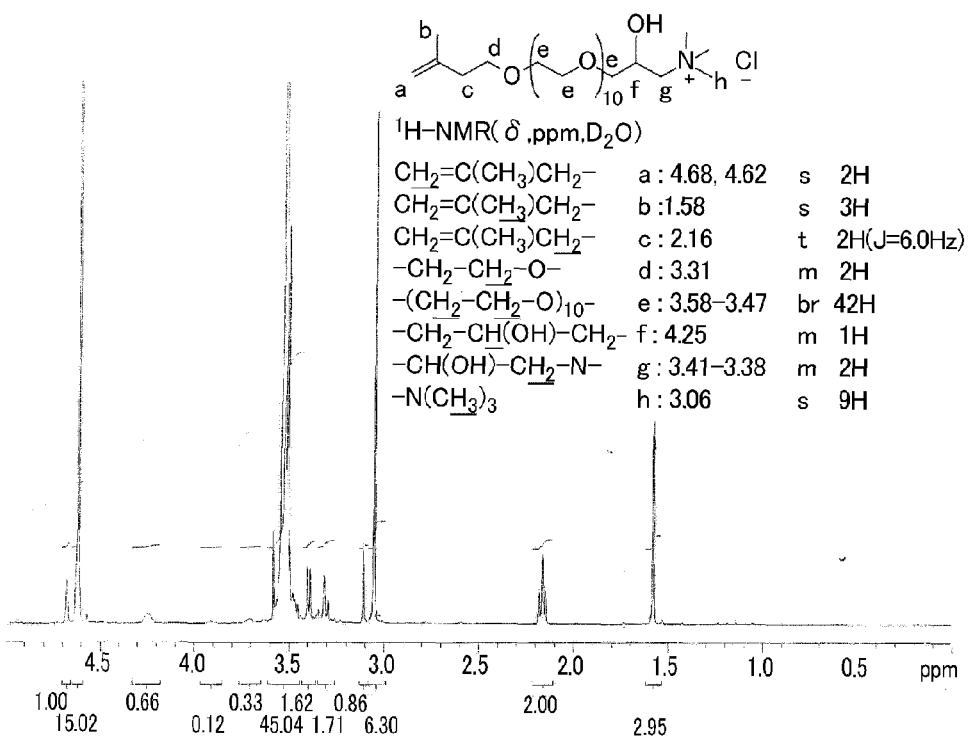
FIG. 4 is a $^1$H-NMR chart of the monomer (1) obtained in Example 4.

13.0 g (0.14 mol) trimethylamine hydrochloride and 7.0 g (0.39 mol) pure water were introduced into a 200-mL four-neck flask equipped with a magnetic stirrer, thermometer, condenser, and dropping funnel and were heated to an internal temperature of 50° C. while stirring and mixing. To this was slowly added dropwise over 3 hours 85.0 g of the reaction solution containing 65.0 g intermediate [A] while maintaining an internal temperature of 50° C. Stirring was then performed for an additional 3 hours. An aqueous solution of monomer (1) was thus obtained. The result of analysis by high-performance liquid chromatography was a yield of 95 mol %. In addition, the production of the monomer (1) shown in FIG. 4 was also confirmed from the $^{1}$H-NMR (that is, a compound with the structure in general formula (32) below in which n is an average of 10).

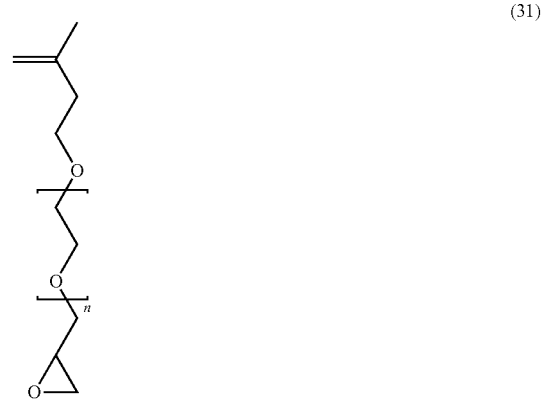

(31)

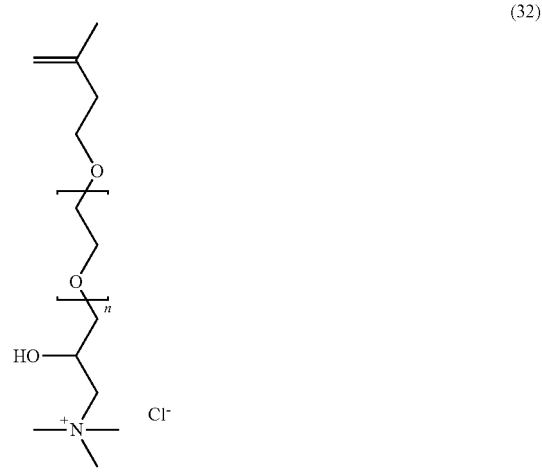

(32)

Example 5

100 g IPN25, 23.3 g (0.25 mol) epichlorohydrin, and 1.4 g (4.4 mmol) tetrabutylammonium bromide were charged all at once to a 200-mL four-neck flask equipped with a stirring paddle, thermometer, and condenser and were heated to an internal temperature of 45 to 50° C. while stirring and mixing. To was slowly added over 30 minutes 3.4 g (0.084 mol) NaOH pellets, and stirring was performed for an additional 5.5 hours while maintaining an internal temperature of 40 to 50° C. After the resulting solution had been cooled to room temperature, the precipitated salt was removed by filtration and the admixed epichlorohydrin and water were removed by reduced-pressure distillation to obtain 95.3 g of a reaction solution containing 73.4 g intermediate [B], for a yield of 70 mol %. In addition, its production was also confirmed from $^{1}$H-NMR is in Example 1 (that is, a compound with the structure in general formula (31) above in which n is an average of 25).

5.6 g (0.060 mol) trimethylamine hydrochloride and 3.1 g (0.17 mol) pure water were introduced into a 200-mL four-neck flask equipped with a magnetic stirrer, thermometer, condenser, and dropping funnel and were heated to an internal temperature of 50° C. while stirring and mixing. To this was slowly added dropwise over 3 hours 85.0 g of the reaction solution containing 66 g intermediate [B] while maintaining an internal temperature of 50° C. Stirring was then performed for an additional 3 hours. An aqueous solution of monomer (2) was thus obtained. The result of analysis by high-performance liquid chromatography was that the reaction had proceeded quantitatively with a yield of 95 mol %. In addition, its production was also confirmed from $^1$H-NMR as in Example 4 (that is, a compound with the structure in general formula (32) above in which n is an average of 25).

Example 6

100 g IPN50, 12.3 g (0.13 mol) epichlorohydrin, and 0.72 g (2.3 mmol) tetrabutylammonium bromide were charged all at once to a 200-mL four-neck flask equipped with a stirring paddle, thermometer, and condenser and were heated to an internal temperature of 40 to 50° C. while stirring and mixing. To was slowly added over 30 minutes 1.8 g (0.044 mol) NaOH pellets, and stirring was performed for an additional 5.5 hours while maintaining an internal temperature of 40 to 50° C. After the resulting solution had been cooled to room temperature, the precipitated salt was removed by filtration and the admixed epichlorohydrin and water were removed by reduced-pressure distillation to obtain 94.1 g of a reaction solution containing 72.5 g intermediate [C], for a yield of 70 mol %. In addition, its production was also confirmed from $^1$H-NMR is in Example 1 (that is, a compound with the structure in general formula (31) above in which n is an average of 50).

3.0 g (0.032 mol) trimethylamine hydrochloride and 1.6 g (0.089 mol) pure water were introduced into a 200-mL four-neck flask equipped with a magnetic stirrer, thermometer, condenser, and dropping funnel and were heated to an internal temperature of 50° C. while stirring and mixing. To this was slowly added dropwise over 3 hours 85.0 g of the reaction solution containing 65.9 g intermediate [C] while maintaining an internal temperature of 50° C. Stirring was then performed for an additional 3 hours. An aqueous solution of monomer (3) was thus obtained. The result of analysis by high-performance liquid chromatography was that the reaction had proceeded quantitatively with a yield of 95 mol %. In addition, its production was also confirmed from $^1$H-NMR as in Example 4 (that is, a compound with the structure in general formula (32) above in which n is an average of 50).

Example 7

100 g IPN10 and 0.306 g (0.002 mol) of a 46% boron trifluoride.diethyl ether complex were introduced into a 200-mL four-neck flask equipped with a magnetic stirrer, thermometer, condenser, and dropping funnel and 18.2 g (0.19 mol) epichlorohydrin was added dropwise over 2 hours under a nitrogen atmosphere while stirring at an internal temperature of 80° C. Stirring was then performed for an additional 4 hours. An intermediate [D] for monomer (1) was thus obtained. The result of high-performance liquid chromatography was a yield of 60 mol %.

108.0 g intermediate [D] for monomer (1) was then introduced into a 200-mL four-neck flask equipped with a magnetic stirrer, thermometer, condenser, and dropping funnel and 35.5 g (0.18 mol) of a 30% aqueous trimethylamine solution was added dropwise over 1 hour while stirring at an internal temperature of 70° C., and then further stirred for 6 hours. An aqueous solution of monomer (1) was thus obtained. The result of analysis by high-performance liquid chromatography was a yield of 62%. In addition, its production was also confirmed from as in Example 1 (that is, a compound with the structure in general formula (32) above in which n is an average of 10).

Polymerization Example 1

A polymerization reaction system was prepared by introducing 1040.5 g pure water, 158.8 g monomer (1), and 15.9 g IPN10 into a 2000-mL separable glass flask equipped with a reflux condenser and a stirrer (paddle blade) and heating to 90° C. while stirring. Then, 333.4 g N-vinylpyrrolidone (also referred to below as NVP) and 112.9 g of a 15% aqueous solution of 2,2'-azobis(2-methylpropionamidine)dihydrochloride (also referred to below as 15% V50) were each added dropwise from separate nozzles to the stirred polymerization reaction system held at 90° C. The addition times for the individual solutions were 180 minutes for the NVP and 190 minutes for the 15% V50. The addition rate for each solution was held constant and each solution was added continuously. The polymerization was completed by holding (maturing) the reaction solution at 90° C. for an additional 30 minutes after the completion of NVP addition. After the completion of polymerization, the polymerization reaction solution was stirred and allowed to cool. An aqueous solution of polymer (1) was thus obtained.

The weight-average molecular weight of polymer (1) was 18,500 and its number-average molecular weight was 8,800.

Polymerization Example 2

A polymerization reaction system was prepared by introducing 972.3 g pure water, 111.1 g monomer (1), and 22.2 g IPN10 into a 2000-mL separable glass flask equipped with a reflux condenser and a stirrer (paddle blade) and heating to 90° C. while stirring. Then, 333.4 g NVP and 109.7 g 15% V50 were each added dropwise from separate nozzles to the stirred polymerization reaction system held at 90° C. The addition times for the individual solutions were 180 minutes for the NVP and 190 minutes for the 15% V50. The addition rate for each solution was held constant and each solution was added continuously. The polymerization was completed by holding (maturing) the reaction solution at 90° C. for an additional 30 minutes after the completion of NVP addition. After the completion of polymerization, the polymerization reaction solution was stirred and allowed to cool. An aqueous solution of polymer (2) was thus obtained.

The weight-average molecular weight of polymer (2) was 19,800 and its number-average molecular weight was 7,400.

Polymerization Example 3

A polymerization reaction system was prepared by introducing 906.9 g pure water, 69.5 g monomer (2), and 27.8 g IPN25 into a 2000-mL separable glass flask equipped with a reflux condenser and a stirrer (paddle blade) and heating to 90° C. while stirring. Then, 333.4 g NVP and 103.3 g 15% V50 were each added dropwise from separate nozzles to the stirred polymerization reaction system held at 90° C. The addition times for the individual solutions were 180 minutes for the NVP and 190 minutes for the 15% V50. The addition rate for each solution was held constant and each solution was added continuously. The polymerization was completed by holding (maturing) the reaction solution at 90° C. for an additional 30 minutes after the completion of NVP addition. After the completion of polymerization, the polymerization reaction solution was stirred and allowed to cool. An aqueous solution of polymer (3) was thus obtained.

The weight-average molecular weight of polymer (3) was 16,400 and its number-average molecular weight was 6,800.

Polymerization Example 4

A polymerization reaction system was prepared by introducing 909.7 g pure water, 69.5 g monomer (3), and 27.8 g IPN50 into a 2000-mL separable glass flask equipped with a reflux condenser and a stirrer (paddle blade) and heating to 90° C. while stirring. Then, 333.4 g NVP and 101.8 g 15% V50 were each added dropwise from separate nozzles to the stirred polymerization reaction system held at 90° C. The addition times for the individual solutions were 180 minutes for the NVP and 190 minutes for the 15% V50. The addition rate for each solution was held constant and each solution was added continuously. The polymerization was completed by holding (maturing) the reaction solution at 90° C. for an additional 30 minutes after the completion of NVP addition. After the completion of polymerization, the polymerization reaction solution was stirred and allowed to cool. An aqueous solution of polymer (4) was thus obtained.

The weight-average molecular weight of polymer (4) was 15,100 and its number-average molecular weight was 6,200.

Polymerization Example 5

A polymerization reaction system was prepared by introducing 1081.6 g pure water, 555.7 g monomer (3), and 55.6 g IPN50 into a 3000-mL separable glass flask equipped with a reflux condenser and a stirrer (paddle blade) and heating to 90° C. while stirring. Then, 333.4 g NVP and 111.7 g 15% V50 were each added dropwise from separate nozzles to the stirred polymerization reaction system held at 90° C. The addition times for the individual solutions were 180 minutes for the NVP and 190 minutes for the 15% V50. The addition rate for each solution was held constant and each solution was added continuously. The polymerization was completed by holding (maturing) the reaction solution at 90° C. for an additional 30 minutes after the completion of NVP addition. After the completion of polymerization, the polymerization reaction solution was stirred and allowed to cool. An aqueous solution of polymer (5) was thus obtained.

The weight-average molecular weight of polymer (5) was 8,300 and its number-average molecular weight was 3,500.

Polymerization Example 6

448.5 g pure water was introduced into a 2000-mL separable glass flask equipped with a reflux condenser and a stirrer and was heated to 90° C. while stirring. The following were then each added dropwise from separate nozzles to the polymerization reaction system while the system was held at 90° C. and stirred: 258.0 g methyl acrylate (also referred to below as AM), 143.3 g monomer (1), 57.3 g IPN10, 68.6 g 15% sodium persulfate (also referred to below as NaPS), and 58.8 g 35% sodium bisulfite (also referred to below as SBS). The respective addition times were 180 minutes for the AM, 120 minutes for monomer (1), 120 minutes for the IPN10, 190 minutes for the 15% NaPS, and 190 minutes for the 35% SBS. The addition rate for each solution was held constant and each solution was added continuously. The polymerization was completed by holding (maturing) the reaction solution at 90° C. for an additional 30 minutes after the completion of AM addition. After the completion of polymerization, the polymerization reaction solution was stirred and allowed to cool. An aqueous solution of polymer (6) was thus obtained.

Polymerization Example 7

219.6 g pure water was introduced into a 2000-mL separable glass flask equipped with a reflux condenser and a stirrer and was heated to 90° C. while stirring. The following were then each added dropwise from separate nozzles to the polymerization reaction system while the system was held at 90° C. and stirred: 355.3 g of a 60% aqueous acrylamide solution (also referred to below as 60% AAm), 118.5 g monomer (1), 47.4 g IPN10, 67.1 g 15% NaPS, and 57.5 g 35% SBS. The respective addition times were 180 minutes for the 60% AAm, 120 minutes for monomer (1), 120 minutes for the IPN10, 190 minutes for the 15% NaPS, and 190 minutes for the 35% SBS. The addition rate for each solution was held constant and each solution was added continuously. The polymerization was completed by holding (maturing) the reaction solution at 90° C. for an additional 30 minutes after the completion of the 60% AAm addition. After the completion of polymerization, the polymerization reaction solution was stirred and allowed to cool. An aqueous solution of polymer (7) was thus obtained.

Polymerization Example 8

900.9 g pure water was introduced into a 3000-mL separable glass flask equipped with a reflux condenser and a stirrer and was heated to 90° C. while stirring. The following were then each added dropwise from separate nozzles to the polymerization reaction system while the system was held at 90° C. and stirred: 348.0 g hydroxyethyl acrylate (also referred to below as HEA), 580.0 g monomer (3), 58.0 g IPN50, 67.3 g 15% NaPS, and 57.7 g 35% SBS. The respective addition times were 180 minutes for the HEA, 150 minutes for monomer (3), 150 minutes for the IPN50, 190 minutes for the 15% NaPS, and 190 minutes for the 35% SBS. The addition rate for each solution was held constant and each solution was added continuously. The polymerization was completed by holding (maturing) the reaction solution at 90° C. for an additional 30 minutes after the completion of the HEA addition. After the completion of polymerization, the polymerization reaction solution was stirred and allowed to cool. An aqueous solution of polymer (8) was thus obtained.

Polymerization Example 9

623.6 g pure water was introduced into a 2000-mL separable glass flask equipped with a reflux condenser and a stirrer and was heated to 65° C. while stirring. The following were then each added dropwise from separate nozzles to the polymerization reaction system while the system was held at 65° C. and stirred: 333.4 g vinyl acetate (also referred to below as VAc), 55.6 g monomer (2), 22.2 g IPN25, and 102.6 g 15% V50. The respective addition times were 180 minutes for the VAc, 150 minutes for monomer (2), 150 minutes for the IPN25, and 190 minutes for the 15% V50. The addition rate for each solution was held constant and each solution was added continuously. The polymerization was completed by holding (maturing) the reaction solution at 65° C. for an additional 30 minutes after the completion of the VAc addition. After the completion of polymerization, the polymerization reaction solution was stirred and allowed to cool. An aqueous solution of polymer (9) was thus obtained.

Comparative Polymerization Example 1

A polymerization reaction system was prepared by introducing 10.0 g pure water, 475.0 g of a 60% aqueous diallyldimethylammonium chloride solution (also referred to below as 60% DADMAC), and 15.0 g methyl methacrylate (also referred to below as MMA) into a 1000-mL separable glass flask equipped with a reflux condenser and a stirrer (paddle blade) and heating to the boiling point while stirring. Then, 38.3 g 15% NaPS and 16.4 g of a 35% aqueous disodium metabisulfite solution (also referred to below as 35% MBS) were each added dropwise from separate nozzles to the stirred polymerization reaction system being held at the boiling point. The addition times for the individual solutions were 190 minutes for the 15% NaPS and, for the 35% MBS, 30 minutes after adjustment to 95° C. after the completion of the addition of the 15% NaPS. The addition rate for each solution was held constant and each solution was added continuously. The polymerization was completed by holding (maturing) the reaction solution at 95° C. for an additional 30 minutes after the completion of the 35% MBS addition. After the completion of polymerization, the polymerization reaction solution was diluted by the addition of 335.3 g pure water while being stirred and allowed to cool. An aqueous solution of comparative polymer (1) was thus obtained.

Example 8

The compatibility with surfactant and the anti-dye transfer performance were evaluated by the previously described methods on polymers (1) to (5) and comparative polymer (1) and on, as a comparative polymer (2), Polyvinylpyrrolidone K30 (Wako Pure Chemical Industries, Ltd.), which is a homopolymer of N-vinylpyrrolidone (NVP). The results are given in Table 3.

The following abbreviations are used in Table 3.
IPN10: isoprenol/ethylene oxide adduct (average addition=10 moles)
IPN25: isoprenol/ethylene oxide adduct (average addition=25 moles)
IPN50: isoprenol/ethylene oxide adduct (average addition=50 moles)
NVP: N-vinylpyrrolidone
DADMAC: diallyldimethylammonium chloride
MMA: methyl methacrylate

TABLE 3

|  | Composition (mass %) | Compatibility | Anti-dye transfer performance (%) |
|---|---|---|---|
| Polymer (1) | Monomer (1)/IPN10/NVP = 20/10/70 | ++ | 39.6 |
| Polymer (2) | Monomer (1)/IPN10/NVP = 15/10/75 | ++ | 40.2 |
| Polymer (3) | Monomer (2)/IPN25/NVP = 10/10/80 | ++ | 41.1 |
| Polymer (4) | Monomer (3)/IPN50/NVP = 10/10/80 | ++ | 41.0 |
| Polymer (5) | Monomer (3)/IPN50/NVP = 40/20/40 | ++ | 38.8 |
| Comparative polymer (1) | DADMAC/MMA = 95/5 | − | 36.8 |
| Comparative polymer (2) | NVP = 100 | − | 38.1 |

As is clear from Table 3, the polymers according to the present invention have a significantly better anti-dye transfer performance and compatibility with surfactant than the conventional comparative polymers. It was shown that the cationic group-containing monomer of the present invention can be favorably used as a starting material for these polymers.

In the preceding examples, polymer synthesis was carried out using a cationic group-containing monomer having a particular structure as one type of monomer component. However, the mechanism whereby polymer synthesized using a cationic group-containing monomer with general formula (12) as a monomer component exhibits an excellent anti-dye transfer performance and an excellent compatibility with surfactant, is entirely the same in polymers synthesized using a cationic group-containing monomer with general formula (12) as a monomer component. Accordingly, it can be concluded that, based on the results in the preceding examples, the present invention can be applied and its advantageous functional effects can be manifested throughout the entire technical range of the present invention and in the various embodiments disclosed in this Specification.

The isoprenol/ethylene oxide adduct, amino group-containing monomer, and reaction intermediate were quantitated by liquid chromatography using the conditions described above in <Quantitation of the intermediate composition>. The compatibility of the polymer with surfactant and the solids fraction in the polymer were measured as described above in <Method for evaluating the compatibility with surfactant> and <Measurement of the solids fraction>. The weight-average molecular weight of the polymer and the anti-soil redeposition performance of the polymer were measured and evaluated according to the following methods.
<Conditions for Measuring the Weight-Average Molecular Weight>
instrumentation: L-7000 series from Hitachi, Ltd.
detector: RI
column: TSK-guard column+TSK-GEL α-3000+TSK-GEL α-2500, from Tosoh Corporation
column temperature: 40° C.
flow rate: 0.4 mL/minute
calibration curve: POLYETHYLENE GLYCOL STANDARD from GL Sciences Inc.
eluent: 100 mM boric acid (pH 9.2)/acetonitrile=4/1 (mass ratio)
<The Anti-Soil Redeposition Performance Test>
The anti-soil redeposition performance test was run using carbon black and the following procedure.
(1) A white fabric was prepared by cutting a polyester fabric obtained from Testfabrics, Inc., to 5 cm×5 cm. The whiteness of this white fabric was preliminarily measured by reflectance using an SE2000 Colormeter from Nippon Denshoku Industries Co., Ltd.
(2) Hard water was prepared by adding pure water to 1.1 g calcium chloride dihydrate to make 15 kg.
(3) An aqueous surfactant solution was prepared by adding pure water to 4.0 g polyoxyethylene (20) lauryl ether to bring to 100.0 g. The pH was adjusted to 8.5 using sodium hydroxide.
(4) A tergotometer was set to 25° C. and the following were introduced into the pot: 1 L of the hard water, 5 g of the aqueous surfactant solution, 1 g of the 5% (as the solids fraction) aqueous polymer solution, and 1.0 g carbon black. Stirring was carried out for 1 minute at 150 rpm. This was followed by the introduction of 5 sheets of the white fabric and stirring for 10 minutes at 100 rpm.
(5) The water was drained from the white fabric by hand; 1 L tap water brought to 25° C. was introduced into the pot; and stirring was performed for 2 minutes at 100 rpm.
(6) A damp cloth was set on the white fabric and drying was done with an iron while stretching out the wrinkles. This was followed by another reflectance measurement of the whiteness of the white fabric using the colormeter indicated above.

(7) Using the preceding measurement results, the anti-soil redeposition percentage was determined using the following formula.

anti-soil redeposition percentage(%)=(post-test whiteness)/(original whiteness of the white fabric)×100

Example 9

400 g IPN10, 351.7 g epichlorohydrin, and 94.9 g of a 48% aqueous sodium hydroxide solution (also referred to below as 48% NaCH) were introduced into a one-liter four-neck flask equipped with a stirring paddle, thermometer, and condenser and a reaction was run by stirring for 6 hours while holding at 50° C. After the reaction, the produced salt was removed and the epichlorohydrin and water were thereafter removed from the residual organic layer to yield 451.2 g of a reaction solution containing intermediate [A] (compound with the structure in general formula (31) above in which n is an average of 10). According to the results of analysis by liquid chromatography, 324.9 g intermediate [A] and 64.1 g IPN10 were present.

Figure 5:
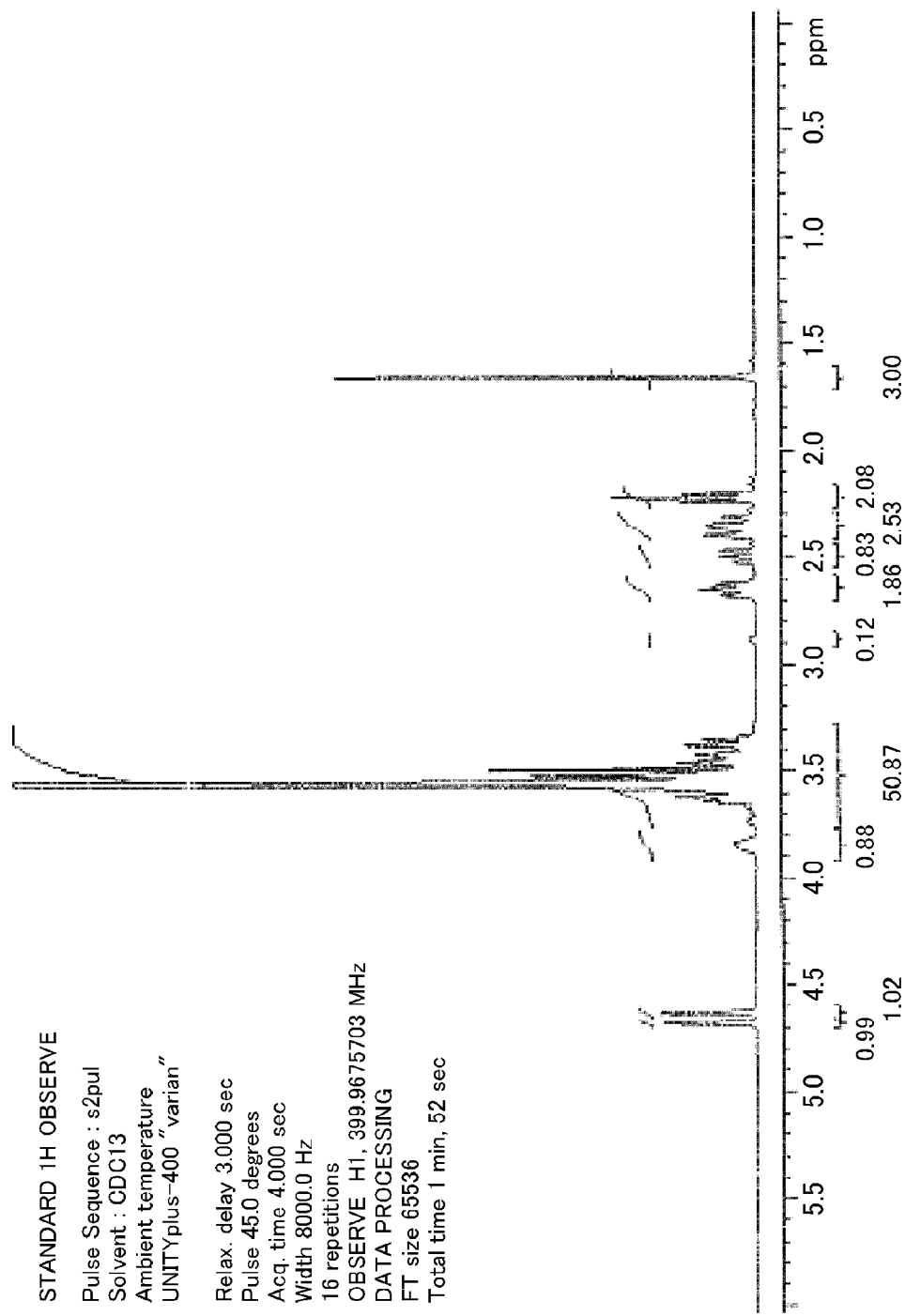
FIG. 5 is a $^1$H-NMR chart of the monomer (5) obtained in Example 9.

100.0 g of the aforementioned reaction solution containing intermediate [A] and 17.4 g diethanolamine were then introduced into a 200-mL four-neck flask equipped with a stirring paddle, thermometer, and condenser and were stirred for 8 hours while holding at 80° C. This yielded 117.4 g of a solution of monomer (5) (compound with the structure in general formula (33) below in which n is an average of 10). According to the results of analysis by liquid chromatography, 80.8 g monomer (5) and 10.2 g IPN10 were present. The production of monomer (5) was also confirmed from the $^1$H-NMR as shown in FIG. 5.

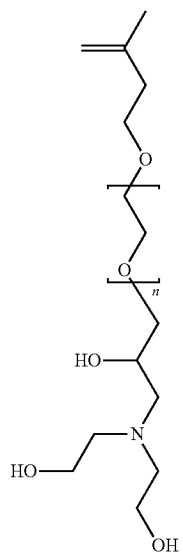

(33)

Example 10

Figure 6:
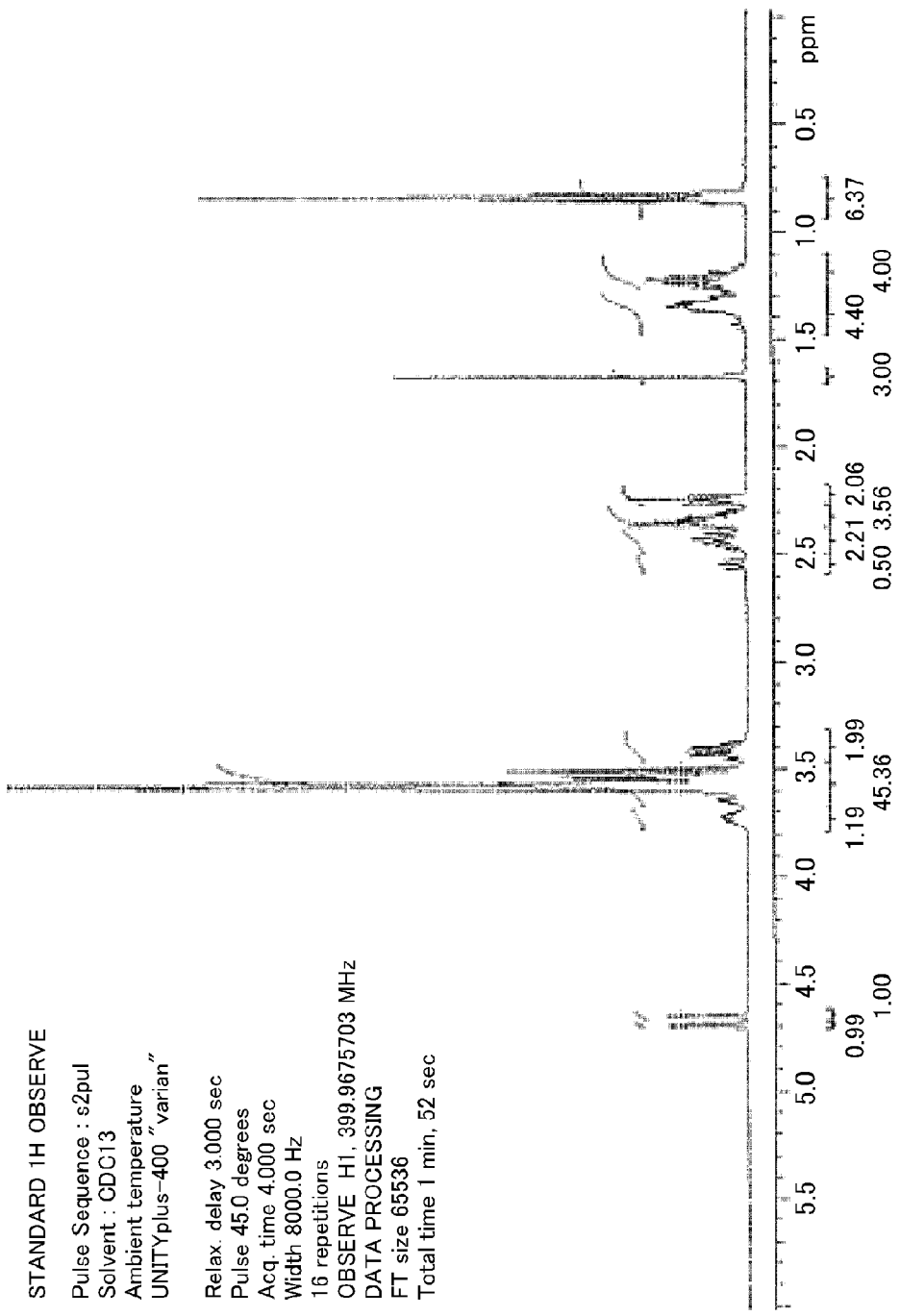
FIG. 6 is a $^1$H-NMR chart of the monomer (6) obtained in Example 10.

100.0 g of the intermediate [A]-containing reaction solution synthesized in Example 9 and 23.2 g dibutylamine were introduced into a 200-mL four-neck flask equipped with a stirring paddle, thermometer, and condenser and stirring was performed for 8 hours while holding at 100° C. This yielded 123.2 g of a solution of monomer (6) (compound with the structure in general formula (34) below in which n is an average of 10). According to the results of analysis by liquid chromatography, 83.6 g monomer (6) and 10.2 g IPN10 were present. The production of monomer (6) was also confirmed from the $^1$H-NMR as shown in FIG. 6.

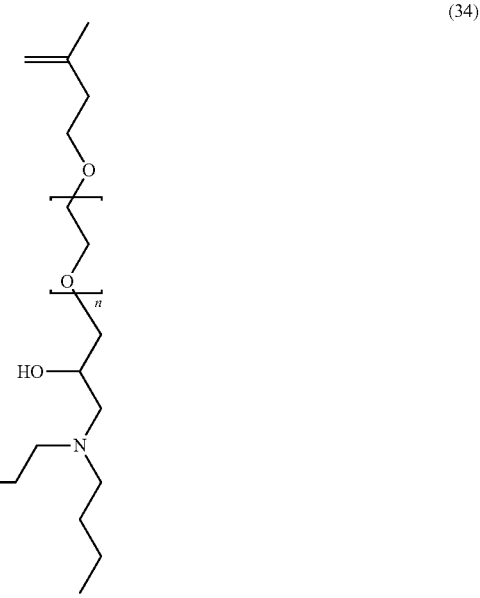

(34)

Example 11

500 g IPN25, 233.7 g epichlorohydrin, and 25.3 g NaOH pellets were introduced into a one-liter four-neck flask equipped with a stirring paddle, thermometer, and condenser and a reaction was run by stirring for 16 hours while holding at 50° C. After the reaction, the produced salt was removed and the epichlorohydrin and water were thereafter removed from the residual organic layer to yield 499.4 g of a reaction solution containing intermediate [B] (compound with the structure in general formula (31) above in which n is an average of 25). According to the results of analysis by liquid chromatography, 389.1 g intermediate [B] and 43.5 g IPN25 were present.

100.0 g of the aforementioned reaction solution containing intermediate [B] and 8.6 g diethanolamine were then introduced into a 200-mL four-neck flask equipped with a stirring paddle, thermometer, and condenser and were stirred for 8 hours while holding at 80° C. This yielded 108.6 g of a solution of monomer (7) (compound with the structure in general formula (33) above in which n is an average of 25). According to the results of analysis by liquid chromatography, 80.3 g monomer (7) and 6.8 g IPN25 were present. Its production was also confirmed from $^1$H-NMR as in Example 9.

Example 12

100.0 g of the intermediate [B]-containing reaction solution synthesized in Example 11 and 11.3 g dibutylamine were introduced into a 200-mL four-neck flask equipped with a stirring paddle, thermometer, and condenser and stirring was performed for 8 hours while holding at 100° C. This yielded 111.3 g of a solution of monomer (8) (compound with the structure in general formula (34) above in which n is an average of 25). According to the results of analysis by liquid chromatography, 81.7 g monomer (8) and 6.8 g IPN25 were present. Its production was also confirmed from the $^1$H-NMR as in Example 10.

Example 13

100 g IPN50, 25.0 g epichlorohydrin, and 2.6 g NaOH pellets were introduced into a 200-mL four-neck flask equipped with a stirring paddle, thermometer, and condenser and a reaction was run by stirring for 16 hours while holding at 50° C. After the reaction, the produced salt was removed and the epichlorohydrin and water were thereafter removed from the residual organic layer to yield 102.3 g of a reaction solution containing intermediate [C] (compound with the structure in general formula (31) above in which n is an average of 50). According to the results of analysis by liquid chromatography, 71.7 g intermediate [C] and 10.0 g IPN50 were present.

100.0 g of the aforementioned reaction solution containing intermediate [C] and 4.1 g diethanolamine were then introduced into a 200-mL four-neck flask equipped with a stirring paddle, thermometer, and condenser and were stirred for 8 hours while holding at 80° C. This yielded 104.1 g of a solution of monomer (9) (compound with the structure in general formula (33) above in which n is an average of 50). According to the results of analysis by liquid chromatography, 69.6 g monomer (9) and 6.9 g IPN50 were present. Its production was also confirmed from the $^1$H-NMR as in Example 9.

Example 14

100.0 g of the intermediate [C]-containing reaction solution synthesized in Example 13 and 5.4 g dibutylamine were introduced into a 200-mL four-neck flask equipped with a stirring paddle, thermometer, and condenser and stirring was performed for 8 hours while holding at 100° C. This yielded 105.4 g of a solution of monomer (10) (compound with the structure in general formula (34) above in which n is an average of 50). According to the results of analysis by liquid chromatography, 70.3 g monomer (10) and 9.8 g IPN50 were present. Its production was also confirmed from the $^1$H-NMR as in Example 10.

Polymerization Example 10

A polymerization reaction system was prepared by introducing 150.0 g pure water and 0.0060 g Mohr's salt into a 2000-mL separable glass flask equipped with a reflux condenser and a stirrer (paddle blade) and heating to 70° C. while stirring. The following were then each added dropwise from separate nozzles to the polymerization reaction system while the system was held at 70° C. and stirred: 144.8 g HEA, 144.8 g monomer (5), 17.3 g 80% IPN10, 94.2 g 15% NaPS, 17.3 g 35% SBS, and 227.4 g pure water.

The dropwise addition of all of the solutions was started at the same time, and the addition times for the individual solutions were 180 minutes for the HEA, 120 minutes for monomer (5), 120 minutes for the 80% IPN10, 190 minutes for the 15% NaPS, 180 minutes for the 35% SBS, and 180 minutes for the pure water. The addition rate for each solution was held constant and each solution was added continuously. The polymerization was completed by holding (maturing) the reaction solution at 70° C. for an additional 30 minutes after the completion of the 15% NaPS addition. An aqueous solution containing copolymer (10) in a solids fraction concentration of 45% (copolymer composition (10)) was thus obtained.

Polymerization Example 11

A polymerization reaction system was prepared by introducing 150.0 g pure water and 0.0074 g Mohr's salt into a 2000-mL separable glass flask equipped with a reflux condenser and a stirrer (paddle blade) and heating to 70° C. while stirring. The following were then each added dropwise from separate nozzles to the polymerization reaction system while the system was held at 70° C. and stirred: 257.4 g dimethylaminoethyl acrylate (also referred to below as DAA), 178.5 g monomer (5), 21.3 g 80% IPN10, 96.5 g 15% NaPS, 17.7 g 35% SBS, and 328.6 g pure water.

The dropwise addition of all of the solutions was started at the same time, and the addition times for the individual solutions were 180 minutes for the DAA, 120 minutes for monomer (5), 120 minutes for the 80% IPN10, 190 minutes for the 15% NaPS, 180 minutes for the 35% SBS, and 180 minutes for the pure water. The addition rate for each solution was held constant and each solution was added continuously. The polymerization was completed by holding (maturing) the reaction solution at 70° C. for an additional 30 minutes after the completion of the 15% NaPS addition. An aqueous solution containing copolymer (11) in a solids fraction concentration of 45% (copolymer composition (11)) was thus obtained.

Comparative Polymerization Example 2

40 g of a polyethyleneimine (weight-average molecular weight (Mw)=9,500, number-average molecular weight (Mn)=6,500, also referred to below as PEI) was introduced into a 100-mL separable glass flask equipped with a reflux condenser, a stirrer, and a thermometer and 10 g Denacol EX-121 (2-ethylhexyl glycidyl ether (also referred to below as 2EHGE), from Nagase ChemteX Corporation) was added. This polymer mixture was heated to 60° C. with stirring and a reaction was carried out for 4 hours to obtain comparative copolymer (3). Comparative copolymer (3) dissolved completely in water in any proportion. In addition, its production was confirmed by the detection in the $^1$H-NMR spectrum measured in $D_2O$ of the signal in the vicinity of 3.5 ppm originating from the methine proton produced by the opening of the epoxy ring.

When the aqueous solutions of copolymers (10) and (11) were dried and the $^1$H-NMR was then measured, peaks attributable to residual monomer were not detected, which confirmed that polymers with compositions conforming to the charged quantities had been produced (refer to Table 4).

Example 15

The compatibility with surfactant and the anti-soil redeposition performance were evaluated using the previously described methods on the copolymers (10) and (11) and comparative copolymer (3) obtained in Polymerization Examples 10 and 11 and Comparative Polymerization Example 2. The results are given in Table 4.

The following abbreviations are used in Table 4.
IPN10: isoprenol/ethylene oxide adduct (average addition=10 moles)
HEA: hydroxyethyl acrylate
DAA: dimethylaminoethyl acrylate
PEI: polyethyleneimine
2EHGE: 2-ethylhexyl glycidyl ether

TABLE 4

| | Composition (mass %) | Weight-average molecular weight | Compatibility | Anti-soil redeposition percentage (%) |
|---|---|---|---|---|
| Copolymer (10) | Monomer (5)/IPN10/HEA = 30/10/60 | 27,000 | ++ | 80 |
| Copolymer (11) | Monomer (5)/IPN10/DAA = 30/10/60 | 58,000 | ++ | — |
| Comparative polymer (3) | PEI/2EHGE = 80/20 | 10,000 | − | 65 |

As is clear from Table 4, the amino group-containing polymers according to the present invention have a significantly better anti-soil redeposition performance and compatibility with surfactant than the conventional comparative polymer. It was shown that the amino group-containing monomer of the present invention can be favorably used as a starting material for these polymers.

In the preceding examples, polymer synthesis was carried out using an amino group-containing monomer having a particular structure as one type of monomer component. However, the mechanism whereby polymer synthesized using an amino group-containing monomer with general formula (14) as a monomer component exhibits an excellent anti-soil redeposition performance and an excellent compatibility with surfactant, is entirely the same in polymers synthesized using an amino group-containing monomer with general formula (14) as a monomer component. Accordingly, it can be concluded that, based on the results in the preceding examples, the present invention can be applied and its advantageous functional effects can be manifested throughout the entire technical range of the present invention and in the various embodiments disclosed in this Specification.

The sulfonic acid group-containing monomer, reaction intermediate, and isoprenol/ethylene oxide adduct were quantitated by liquid chromatography using the conditions described above in <Quantitation of the intermediate composition>. The solids fraction in the polymer was measured as described above in <Measurement of the solids fraction>. The weight-average molecular weight of the polymer, its anti-gelation performance, and its calcium ion sequestration capacity were measured and evaluated according to the following methods.

<Conditions for Measuring the Weight-Average Molecular Weight>
instrumentation: HLC-8320GPC from Tosoh Corporation
detector: RI
column: SHODEX Asahipak GF-310-HQ, GF-710-HQ, GF-1G 7B, from Showa Denko Kabushiki Kaisha
column temperature: 40° C.
flow rate: 0.5 mL/minute
calibration curve: standard polyacrylic acid from Sowa Science Corporation
eluent: 0.1 N aqueous sodium acetate solution <Method for Measuring the Anti-Gelation Performance>

Deionized water, a boric acid-sodium borate pH buffer, an aqueous 1% solution of the copolymer, and a calcium chloride solution were added in sequence to a 500-mL tall beaker to produce 500 mL of a test solution that had a pH of 8.5, 100 mg solids fraction/L of the copolymer, and a calcium hardness of 120 mg $CaCO_3$/L. The tall beaker was sealed with a polyethylene film and held at quiescence for 1 hour in a thermostatted water tank at 90° C. The turbidity in the test solution produced by the gel produced by bonding between the copolymer and calcium ion was detected by measuring the absorbance in a 50-mm quartz cell at a UV wavelength of 380 nm, and the anti-gelation performance was evaluated based on the obtained absorbance value. Here, smaller values indicate a better anti-gelation performance.

<The Calcium Ion Sequestration Capacity>

For the calcium ion calibration curve standard solutions, calibration curve sample solutions were prepared by preparing 50 g of a 0.01 mol/L aqueous solution, 50 g of a 0.001 mol/L aqueous solution, and 50 g of a 0.0001 mol/L aqueous solution using calcium chloride dihydrate; adjusting into the pH 9.9 to 10.2 range with 1.0% aqueous NaOH solution; adding 1 mL of a 4 mol/L aqueous potassium chloride solution (abbreviated below as 4M-KCl aqueous solution); and thoroughly stirring using a magnetic stirrer. In addition, for the calcium ion test standard solution, the required amount (50 g per 1 sample) of the 0.001 mol/L aqueous solution was similarly prepared using calcium chloride dihydrate.

Then, 10 mg as the solids fraction of the test sample (the (co)polymer) was weighed into a 100-mL beaker; 50 g of the aforementioned calcium ion test standard solution was added; and thorough stirring was performed using a magnetic stirrer. The (co)polymer used as the test sample was the (co)polymer that had been neutralized with an aqueous 48% sodium hydroxide solution (also referred to below as 48% NaOH) so as to give pH=7.5 at a solids fractions of 40 weight %. Then, as for the calibration curve sample, the test sample solution was prepared by adjusting into the pH 9.9 to 10.2 range with 1.0% aqueous NaOH solution and adding 1 mL 4M-KCl aqueous solution.

The thusly prepared calibration curve sample solutions and test sample solution were submitted to measurement using an Orion 9720BNWP Sure-Flow calcium combination electrode from Thermo Fisher Scientific Inc., and a COM-1700 titrator from Hiranuma Sangyo Corporation.

Example 16

400 g IPN10, 351.7 g epichlorohydrin, and 94.9 g 48% NaOH were introduced into a one-liter four-neck flask equipped with a stirring paddle, thermometer, and condenser and a reaction was run by stirring for 6 hours while holding at 50° C. After the reaction, the produced salt was removed and the epichlorohydrin and water were thereafter removed from the residual organic layer to yield 451.2 g of a reaction solution containing intermediate [A] (compound with the structure in general formula (31) above in which n is an average of 10). According to the results of analysis by liquid chromatography, 324.9 g intermediate [A] and 64.1 g IPN10 were present.

Figure 7:
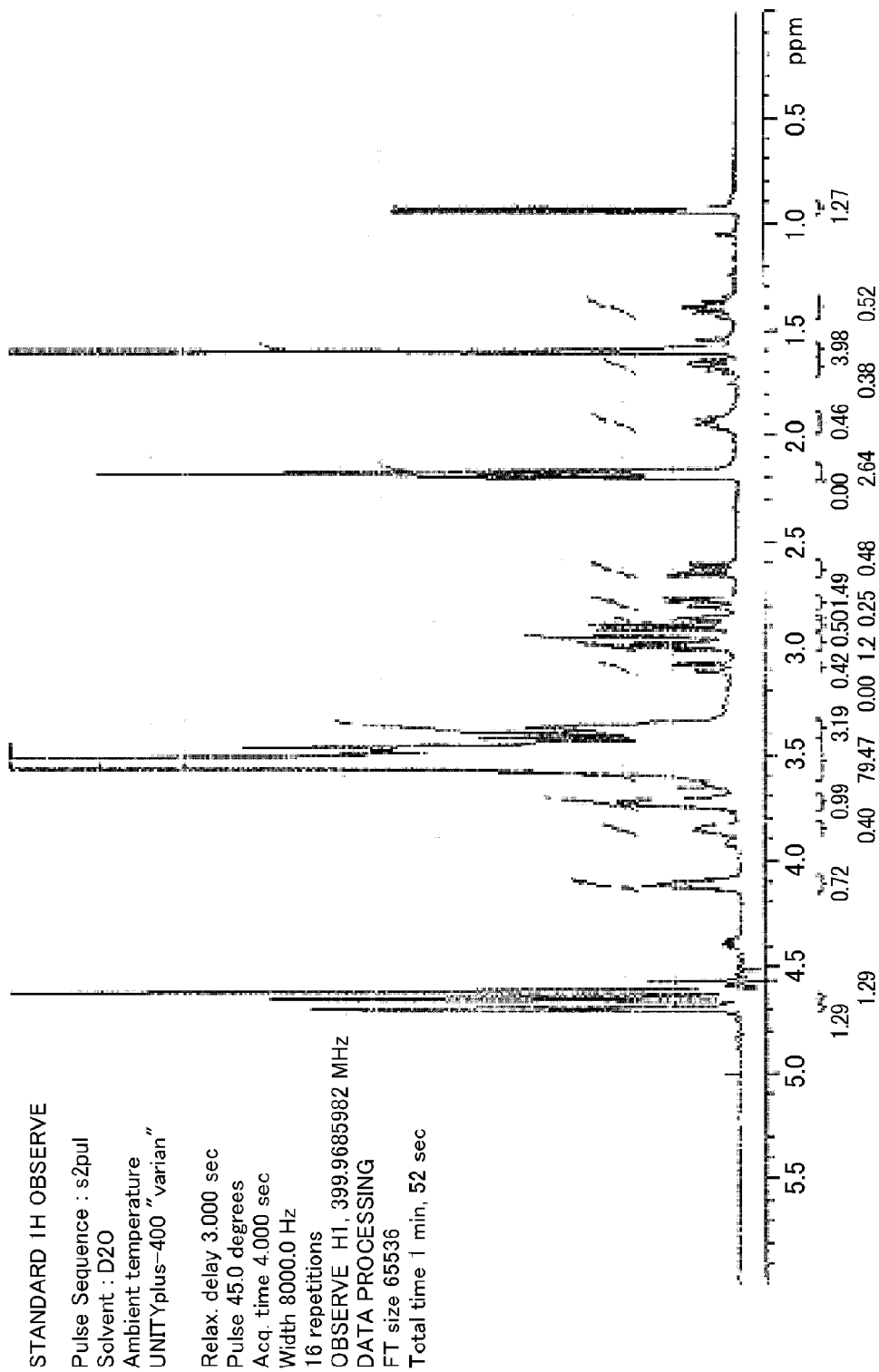
FIG. 7 is a chart of the monomer (11) obtained in Example 16.

While injecting nitrogen, a reaction system was prepared by introducing 129.5 g pure water, 6.0 g 48% NaOH, and 50.0 g 40% SBS into a one-liter SUS separable flask equipped with a stirrer, thermometer, nitrogen inlet tube, and a cold trap at the nitrogen outlet port and heating to 63° C. while stirring. Then, 140.0 g of the aforementioned intermediate [A]-containing reaction solution was continuously added dropwise at a constant rate with stirring over 120 minutes to the reaction system held at 63° C. This yielded 325.5 g of a solution of monomer (11) (compound with the structure in general formula (35) below in which n is an average of 10). The production of monomer (11) was confirmed as a result of analysis by ¹H-NMR as shown in FIG. 7. The complete consumption of intermediate [A] was also confirmed by analysis by liquid chromatography.

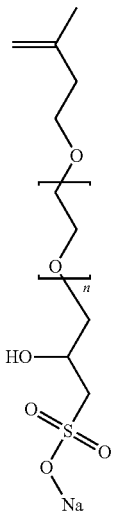

(35)

Polymerization Example 12

A polymerization reaction system was prepared by introducing 25.0 g pure water, 45.1 g maleic anhydride (also abbreviated below as MA), and 60.5 g 48% NaOH into a one-liter SUS separable flask equipped with a reflux condenser and a stirrer (paddle blade) and heating to the boiling point while stirring. The following were then each added dropwise from separate nozzles to the polymerization reaction system while the system was held under reflux at the boiling point and stirred: 222.3 g of the monomer (11) solution, 41.4 g of an 80% aqueous acrylic acid solution (also referred to below as 80% AA), 16.3 g 15% NaPS, and 2.9 g 35% aqueous hydrogen peroxide (also referred to below as 35% $H_2O_2$). The dropwise addition of all of the solutions was started at the same time. The addition times of the individual solutions were 120 minutes for the monomer (11) solution, the 80% AA, and the 15% NaPS and 75 minutes for the 35% $H_2O_2$. The addition rate for each solution was held constant and each solution was added continuously. The polymerization was completed by holding (maturing) the polymerization reaction solution under reflux at the boiling point for an additional 30 minutes after the completion of addition of the 80% AA solution. After the completion of polymerization, the polymerization reaction solution was stirred and allowed to cool and was neutralized by the gradual dropwise addition of 8.1 g 48% NaOH to the polymerization reaction solution while stirring. An aqueous solution of polymer (12) was thus obtained. The weight-average molecular weight of polymer (12) was 48,000.

Polymerization Example 13

A polymerization reaction system was prepared by introducing 25.0 g pure water, 45.1 g MA, 222.3 g of the monomer (11) solution, and 60.5 g 48% NaOH into a one-liter SUS separable flask equipped with a reflux condenser and a stirrer (paddle blade) and heating to the boiling point while stirring. The following were then each added dropwise from separate nozzles to the polymerization reaction system while the system was held under reflux at the boiling point and stirred: 41.4 g 80% AA, 16.3 g 15% NaPS, and 2.9 g 35% $H_2O_2$. The dropwise addition of all of the solutions was started at the same time. The addition times of the individual solutions were 120 minutes for the 80% AA and the 15% NaPS and 75 minutes for the 35% $H_2O_2$. The addition rate for each solution was held constant and each solution was added continuously. The polymerization was completed by holding (maturing) the polymerization reaction solution under reflux at the boiling point for an additional 30 minutes after the completion of addition of the 80% AA solution. After the completion of polymerization, the polymerization reaction solution was stirred and allowed to cool and was neutralized by the gradual dropwise addition of 8.1 g 48% NaOH to the polymerization reaction solution while stirring. An aqueous solution of polymer (13) was thus obtained.

Polymerization Example 14

A polymerization reaction system was prepared by introducing 100.0 g pure water into a 2.5-L SUS separable flask equipped with a reflux condenser and a stirrer (paddle blade) and heating to 90° C. while stirring. The following were then each added dropwise from separate nozzles to the polymerization reaction system while the system was held at 90° C. and stirred: 653.7 g of the monomer (11) solution, 513.0 g 80% AA, 23.8 g 48% NaOH, 160.0 g 15% NaPS, and 60.0 g 40% SBS. The addition times of the individual solutions were 180 minutes for the monomer (11) solution, the 80% AA, and the 48% NaOH, 210 minutes for the 15% NaPS, and 170 minutes for the 40% SBS. The addition rate for each solution was held constant and each solution was added continuously. The polymerization was completed by holding (maturing) the polymerization reaction solution at 90° C. for an additional 30 minutes after the completion of addition of the 15% NaPS. After the completion of polymerization, the polymerization reaction solution was stirred and allowed to cool and was neutralized by the gradual dropwise addition of 427.5 g 48% NaOH to the polymerization reaction solution while stirring. An aqueous solution of polymer (14) was thus obtained.

Comparative Polymerization Example 3

A polymerization reaction system was prepared by introducing 25.0 g pure water, 45.1 g MA, and 60.5 g 48% NaOH into a one-liter SUS separable flask equipped with a reflux condenser and a stirrer (paddle blade) and heating to the boiling point while stirring. The following were then each added dropwise from separate nozzles to the polymerization reaction system while the system was held under reflux at the boiling point and stirred: 222.3 g of a 30% aqueous IPN10 solution, 41.4 g 80% AA, 16.3 g 15% NaPS, and 2.9 g 35% $H_2O_2$. The dropwise addition of all of the solutions was started at the same time. The addition times of the individual solutions were 120 minutes for the 30% IPN10, 80% AA, and 15% NaPS and 75 minutes for the 35% $H_2O_2$. The addition rate for each solution was held constant and each solution was added continuously. The polymerization was completed by holding (maturing) the polymerization reaction solution under reflux at the boiling point for an additional 30 minutes after the completion of addition of the 80% AA solution. After the completion of polymerization, the polymerization reaction solution was stirred and allowed to cool and was neutralized by the gradual dropwise addition of 8.1 g 48% NaOH to the polymerization reaction solution while stirring. An aqueous solution of comparative polymer (4) was thus obtained.

Example 17

The anti-gelation performance and calcium ion sequestration capacity were evaluated using the previously described methods on the polymer (12) and comparative polymer (4) that were prepared in Polymerization Example 12 and Comparative Polymerization Example 3. The results are given in Table 5.

TABLE 5

|  | Anti-gelation performance | Calcium ion sequestration capacity (mg · CaCO$_3$/1 g) |
| --- | --- | --- |
| Polymer (12) | 0.061 | 190 |
| Comparative polymer (4) | 0.085 | 189 |

As is clear from Table 5, the sulfonic acid group-containing polymer according to the present invention has a significantly better anti-gelation performance than the conventional comparative polymer while having the same calcium sequestration capacity. It was shown that the sulfonic acid group-containing monomer of the present invention can be favorably used as a starting material for this polymer.

In the preceding examples, polymer synthesis was carried out using a sulfonic acid group-containing monomer having a particular structure as one type of monomer component. However, the mechanism whereby polymer synthesized using a sulfonic acid group-containing monomer with general formula (16) as a monomer component exhibits an excellent anti-gelation performance and an excellent metal ion sequestration capacity, is entirely the same in polymers synthesized using a sulfonic acid group-containing monomer with general formula (16) as a monomer component. Accordingly, it can be concluded that, based on the results in the preceding examples, the present invention can be applied and its advantageous functional effects can be manifested throughout the entire technical range of the present invention and in the various embodiments disclosed in this Specification.

The organic ether group-containing monomer, reaction intermediate, and isoprenol/ethylene oxide adduct were quantitated by liquid chromatography using the following conditions and the reaction yield and starting material conversion were calculated.
instrumentation: HPLC8020 system from the Tosoh Corporation column: Capcell Pak C1 UG120 from Shiseido Co., Ltd.
temperature: 40.0° C.
eluent: acetonitrile/10 mmol aqueous sodium hydrogen phosphate solution (adjusted to pH 7 with phosphoric acid)=55/45 (volumetric ratio)
flow rate: 1.0 mL/minute
detector: RI, UV (detection wavelength=210 nm)

Intermediate Synthesis Example 1

400 g IPN10, 351.7 g epichlorohydrin, and 94.9 g 48% NaOH were introduced into a one-liter four-neck flask equipped with a stirring paddle, thermometer, and condenser and a reaction was run by stirring for 6 hours while holding at 50° C. After the reaction, the produced salt was removed and the epichlorohydrin and water were thereafter removed from the residual organic layer to yield 451.2 g of a reaction solution containing intermediate [A] (compound with the structure in general formula (31) above in which n is an average of 10). According to the results of analysis by liquid chromatography, 324.9 g intermediate [A] and 64.1 g IPN10 were present.

Example 18

150.0 g of the aforementioned intermediate [A]-containing reaction solution, 159.9 g n-butanol, and 2.4 g granular potassium hydroxide were then introduced into a 200-mL four-neck flask equipped with a stirring paddle, thermometer, and condenser and were stirred for 2 hours while holding at 80° C. After the reaction, the undissolved potassium hydroxide was removed and the n-butanol was subsequently removed from the residual organic layer to yield 154.1 g of a solution of monomer (12) (compound with the structure in general formula (36) below in which n is an average of 10). According to the results of analysis by liquid chromatography, 95.4 g monomer (12) and 11.1 g IPN10 were present. The monomer (12) yield was 74 mol % with reference to the intermediate [A] starting material. The production of secondary product A (compound with the structure in general formula (37) below in which n is an average of 10) was not observed.

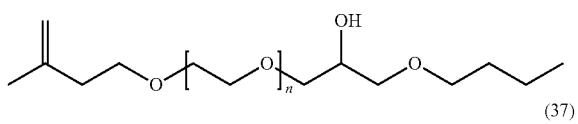

(36)

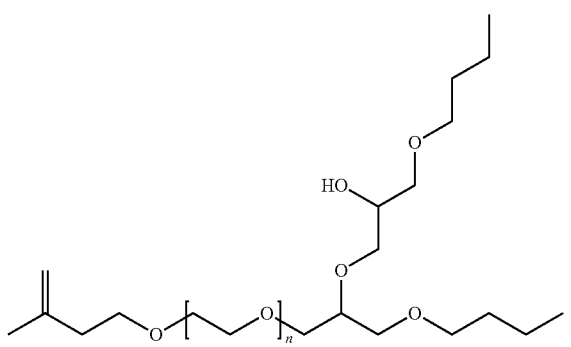

(37)

Comparative Example 2

84.3 g IPN10, 20.8 g butyl glycidyl ether, and 1.1 g granular potassium hydroxide were introduced into a 200-mL four-neck flask equipped with a magnetic stirrer, thermometer, condenser, and dropping funnel and were stirred for 4 hours while holding at 90° C. 106.2 g of a monomer (12) solution was thus obtained. According to the results of analysis by high-performance liquid chromatography, 55.6 g monomer (12), 24.6 g IPN10, and 19.3 g secondary product A were present. The monomer (12) yield was 53 mol % with reference to the starting IPN10.

The examples described above show examples in which reactions were run using particular compounds for the starting materials, catalysts, and hydroxyl group-containing compounds; however, because the reaction mechanisms are entirely the same, it can be concluded that, based on the results in the preceding examples, the present invention can be applied and its advantageous functional effects can be manifested throughout the entire technical range of the present invention and in the various embodiments disclosed in this Specification.

The invention claimed is:

1. A composition containing an intermediate for a water-soluble monomer, that contains a compound (A) represented by the following general formula (1):

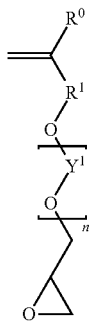

(1)

where, $R^0$ represents a methyl group; $R^1$ represents a methylene group, or an ethylene group; each $Y^1$ is the same or different from one another and represents a $C_{2\text{-}20}$ alkylene group; and n is the average number of moles of addition of the oxyalkylene group ($-Y^1-O-$) and represents a number from 5 to 300, wherein
the composition further contains a compound (B) represented by the following general formula (2):

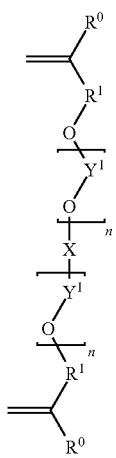

(2)

where, each $R^0$ a methyl group; each $R^1$ is the same or different from one another and represents a methylene group, or an ethylene group; X represents $-CH_2-CH(OR')-CH_2-O-$ or a direct bond; R' represents a hydrogen atom or a glycidyl group; each $Y^1$ is the same or different from one another and represents a $C_{2\text{-}20}$ alkylene group; and n is the average number of moles of addition of the oxyalkylene group ($-Y^1-O-$) and each n is the same or different from one another and represents a number from 5 to 300,
the compound (B) content is 0.1 to 6.0 mol % with reference to the compound (A) content, and
the compound (A) content is 50 to 100 mass % on the basis of 100 mass % of the nonvolatile fraction of the composition containing an intermediate for a water-soluble monomer.

2. The composition containing an intermediate for a water-soluble monomer according to claim 1, wherein
the compound (A) is obtained by reacting an epihalohydrin with a compound (I) represented by the following general formula (I):

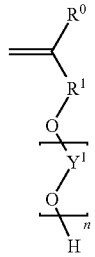

(I)

where, $R^0$ represents a methyl group; $R^1$ represents a methylene group, or an ethylene group; each $Y^1$ is the same or different from one another and represents a $C_{2\text{-}20}$ alkylene group; and n is the average number of moles of addition of the oxyalkylene group ($-Y^1-O-$) and represents a number from 5 to 300
the compound (B) content in the composition containing an intermediate for a water-soluble monomer is 0.1 to 5.0 mol % with reference to the total content of compound (A) and compound (I), and
the total content of compound (A) and compound (I) is 50 to 100 mass % on the basis of 100 mass % be the nonvolatile fraction of the composition containing an intermediate for a water-soluble monomer.

3. The composition containing an intermediate for a water-soluble monomer according to claim 1, wherein each n in formula (1) and formula (2) is the same or different from one another and represents a number from 5 to 200.

4. The composition containing an intermediate for a water-soluble monomer according to claim 2, wherein each n in formula (I) is the same or different from one another and represents a number from 5 to 200.

5. The composition containing an intermediate for a water-soluble monomer according to claim 1, wherein each n in formula (1) and formula (2) is the same or different from one another and represents a number from 10 to 100.

6. The composition containing an intermediate for a water-soluble monomer according to claim 2, wherein each n in formula (I) is the same or different from one another and represents a number from 10 to 100.

7. The composition according to claim 1, wherein the compound (A) is prepared by the production process comprising:
a step of reacting a compound (I) represented by the following general formula (I):

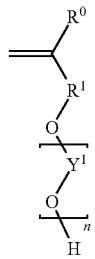

(I)

wherein, $R^0$ represents a methyl group; $R^1$ represents a methylene group, or an ethylene group; each $Y^1$ is the same or different from one another and represents a $C_{2-20}$ alkylene group; and n is the average number of moles of addition of the oxyalkylene group ($-Y^1-O-$) and represents a number from 5 to 300; with an epihalohydrin at a molar ratio of 1/2 to 1/15 (hydroxyl group present in compound (I)/epihalohydrin).

8. The composition containing an intermediate for a water-soluble monomer according to claim 7, wherein the reaction step comprises a step of reacting the compound (I) and the epihalohydrin in the presence of an alkali compound.

9. The composition containing an intermediate for a water-soluble monomer according to claim 7, wherein the reaction step comprises a step of adding an epihalohydrin and a Lewis acid catalyst to the compound (I) and then adding an alkali compound and reacting.

* * * * *